United States Patent
Wang et al.

(10) Patent No.: US 10,479,977 B2
(45) Date of Patent: Nov. 19, 2019

(54) OSTEOCHONDRORETICULAR STEM CELLS FOR BONE AND CARTILAGE REGENERATION

(71) Applicant: THE TRUSTEES OF COLUMBIA UNIVERSITY IN THE CITY OF NEW YORK, New York, NY (US)

(72) Inventors: Timothy Wang, New York, NY (US); Daniel Worthley, Hawthorn (AU); Siddhartha Mukherjee, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/525,208

(22) PCT Filed: Nov. 9, 2015

(86) PCT No.: PCT/US2015/059772
§ 371 (c)(1),
(2) Date: May 8, 2017

(87) PCT Pub. No.: WO2016/073989
PCT Pub. Date: May 12, 2016

(65) Prior Publication Data
US 2017/0335283 A1 Nov. 23, 2017

Related U.S. Application Data

(60) Provisional application No. 62/077,162, filed on Nov. 7, 2014.

(51) Int. Cl.
| | |
|---|---|
| *C12N 5/077* | (2010.01) |
| *C12N 5/0775* | (2010.01) |
| *A61K 35/28* | (2015.01) |
| *A61K 39/00* | (2006.01) |

(52) U.S. Cl.
CPC ............ *C12N 5/0654* (2013.01); *A61K 39/00* (2013.01); *C12N 5/0663* (2013.01); *C12N 5/0669* (2013.01); *A61K 35/28* (2013.01); *A61K 2039/515* (2013.01)

(58) Field of Classification Search
CPC .. C12N 5/0654; C12N 5/0663; C12N 5/0669; A61K 39/00; A61K 35/28; A61K 2039/515
See application file for complete search history.

(56) References Cited

U.S. PATENT DOCUMENTS

2010/0015102 A1* 1/2010 Iwasaki ............... A61L 27/20
424/93.7
2013/0039896 A1 2/2013 Smith et al.

FOREIGN PATENT DOCUMENTS

WO 2007122233 A1 11/2007

OTHER PUBLICATIONS

Niehage et al. The Cell Surface Proteome of Human Mesenchymal Stromal Cells. PLoS ONE 6(5): e20399. p. 1-10 (Year: 2011).*
Giannotti et al. Use of Autologous Human mesenchymal Stromal Cell/Fibrin Clot Constructs in Upper Limb Non-Unions: Long-Term Assessment. PLoS ONE 8(8): e73893. p. 1-9 (Year: 2013).*
Worthley et al. Gremlin 1 Defines a Mesenchymal Stem Cell in the Gastrointestinal Tract, Bone and Tumor Microenvironment. Gastroenterology. vol. 144, Issue 5, Supplement 1, p. S-70 (Year: 2013).*
Canalis, E., et al., "Gremlin1 is required for skeletal development and postnatal skeletal homeostasis", "J Cell Physiol", Jan. 2012, pp. 269-277, vol. 227, No. 1, Published in: doi:10.1002/jcp.22730.
Delorme, B., et al., "Specific lineage-priming of bone marrow mesenchymal stem cells provides the molecular framework for their plasticity", "Stem Cells", Feb. 12, 2009, pp. 1142-1151, vol. 27, Publisher: AlphaMed Press, Published in: doi:10.1002/stem.34.
ISA/US, "International Search Report and Written Opinion in International Application No. PCT/US15/59772 dated Apr. 22, 2016", pp. 1-12.
Jaeger, E, et al., "Hereditary mixed polyposis syndrome is caused by a 40-kb upstream duplication that leads to increased and ectopic expression of the BMP antagonist GREM1", "Nat Genet", May 6, 2012, pp. 699-703, vol. 44, No. 6, Published in: doi:10.1038/ng.2263.
Jo, C., et al., "Intra-Articular Injection of Mesenchymal Stem Cells for the Treatment of Osteoarthritis of the Knee: A Proof-of-Concept Clinical Trial", "Stem Cells", Jan. 21, 2014, pp. 1254-1266, vol. 32, No. 5, Publisher: AlphaMed Press, Published in: doi:101002/stem.1634.
Liu, Y., et al., "Osterix-Cre Labeled Progenitor Cells Contribute to the Formation and Maintenance of the Bone Marrow Stroma", "PLOS One", Aug. 8, 2013, pp. 1-15, vol. 8, No. 8, Published in: doi:10.137/journal. pone.0071318.
Maes, C., et al., "Osteoblast precursors, but not mature osteoblasts, move into developing and fractured bones along with invading blood vessels", "Developmental Cell", Aug. 17, 2010, pp. 329-344, vol. 19, No. 2, Publisher: Cel Pres, Published in: doi:10.1016/j.devcel.2010.07.010.
Mareschi, K, et al., "Multipoint mesenchymal stromal stem cell expansion by plating whole bone marrow at a low cellular density: a more advantageous method for clinical use", "Stem Cells International", Aug. 1, 2011, pp. 1-11, vol. 2012, Publisher: Hindawi Publishing Corporation, Published in: doi:10.1155/2012/920581.
Mendez-Ferrer, S., et al., "Mesenchymal and haematopoietic stem cells form a unique bone marrow niche", "Nature", Aug. 12, 2010, pp. 829-834, vol. 466, Publisher: Macmillan Publishers Limited, Published in: doi:10.1038/nature09262.

(Continued)

*Primary Examiner* — Taeyoon Kim
(74) *Attorney, Agent, or Firm* — Beusse Wolter Sanks & Maire; Timothy H. Van Dyke

(57) ABSTRACT

The invention is directed to osteochondroreticular stem cells and methods of using osteochondroreticular stem cells. In another aspect the invention is directed to a method of treating osteoarthritis or skeletal fractures using osteochondroreticular stem cells.

4 Claims, 40 Drawing Sheets
Specification includes a Sequence Listing.

(56) References Cited

OTHER PUBLICATIONS

Michos, O., et al., "Gremlin-mediated BMP antagonism induces the epithelial-mesenchymal feedback signaling controlling metanephric kidney and limb organogenesis", "Development", May 5, 2004, pp. 3401-3410, vol. 131, Publisher: The Company of Biologists, Published in: doi:10.1242/dev.01251.

Mitola, S., et al., "Gremlin is a novel agonist of the major proangiogenic receptor VEGFR2", "Blood", Jul. 11, 2010, PP. 3677-3680, vol. 116, No. 18, Published in: doi:10.1182/blood-2010-06-291930.

Ono, N., et al., "Vasculature-Associated Cells Expressing Nestin in Developing Bones Encompass Early Cells in the Osteoblast and Endothelial Lineage", "Developmental Cell", May 12, 2014, pp. 330-339, vol. 29, No. 3, Published in: doi:10.1016/j.devcel.2014.03.014.

Park, D., et al., "Endogenous bone marrow MSCs are dynamic, fate-restricted participants in bone maintenance and regeneration", "Cell Stem Cell", Mar. 2, 2012, pp. 259-272, vol. 10, No. 3, Published in: doi:10.1016/j.stem.2012.02.003.

Shibata, W., et al., "Stromal cell-derived factor-1 overexpression induces gastric dysplasia through expansion of stromal myofibroblasts and epithelial progenitors", "Gut", Feb. 23, 2012, pp. 192-200, vol. 62, No. 2, Published in: doi:10.1136/gutjnl-2011-301824.

Sneddon, J., et al., "Bone morphogenetic protein antagonist gremlin 1 is widely expressed by cancer-associated stromal cells and can promote tumor cell proliferation", "PNAS", Oct. 3, 2006, pp. 14842-14847, vol. 103, No. 40, Published in: doi:10.1073/pnas.0606857103.

Thomas, P., et al., "Human mesenchymal stem cells isolated from bone marrow and lymphoid organs support tumor B-cell growth: role of stromal cells in follicular lymphoma pathogenesis", "blood", Sep. 19, 2006, pp. 693-702, vol. 109, No. 2, Published in: doi:10.1182/blood-2006-05-020800.

Worthley, D., et al., "Gremlin 1 Identifies a Skeletal Stem Cell with Bone, Cartilage, and Reticular Stomal Potential", "Cell", Jan. 15, 2015, pp. 269-284, vol. 160, No. 1, Published in: doi:10.1016/j.cell.2014.11.042.

Zhou, B., et al., "Leptin-Receptor-Expressing Mesenchymal Stromal Cells Represent the Main Source of Bone Formed by Adult Bone Marrow", "Cell Stem Cell", Aug. 7, 2014, pp. 154-168, vol. 15, No. 2, Published in: doi:10.1016/j.stem.2014.06.008.

\* cited by examiner

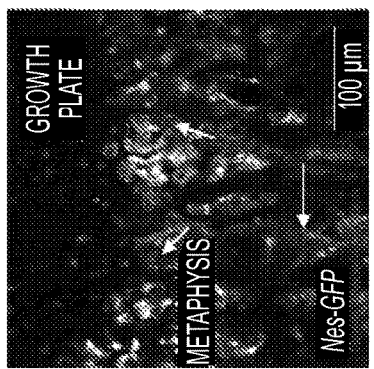
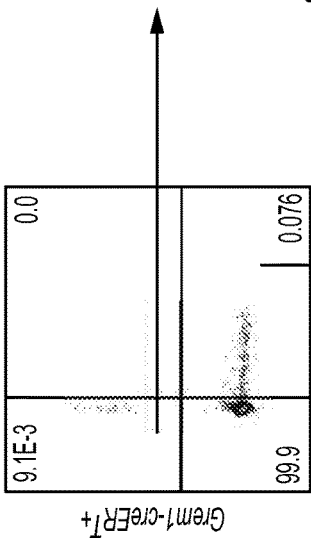
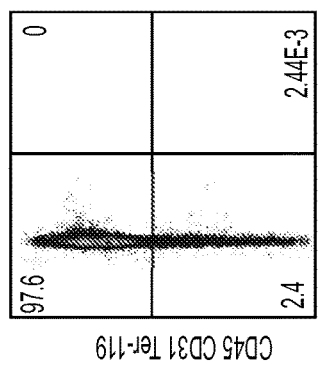
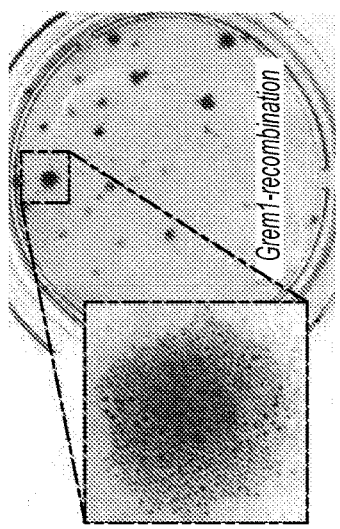
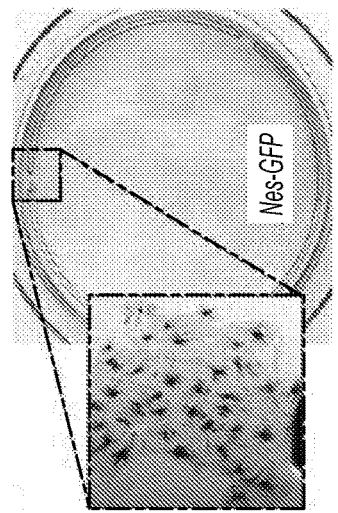

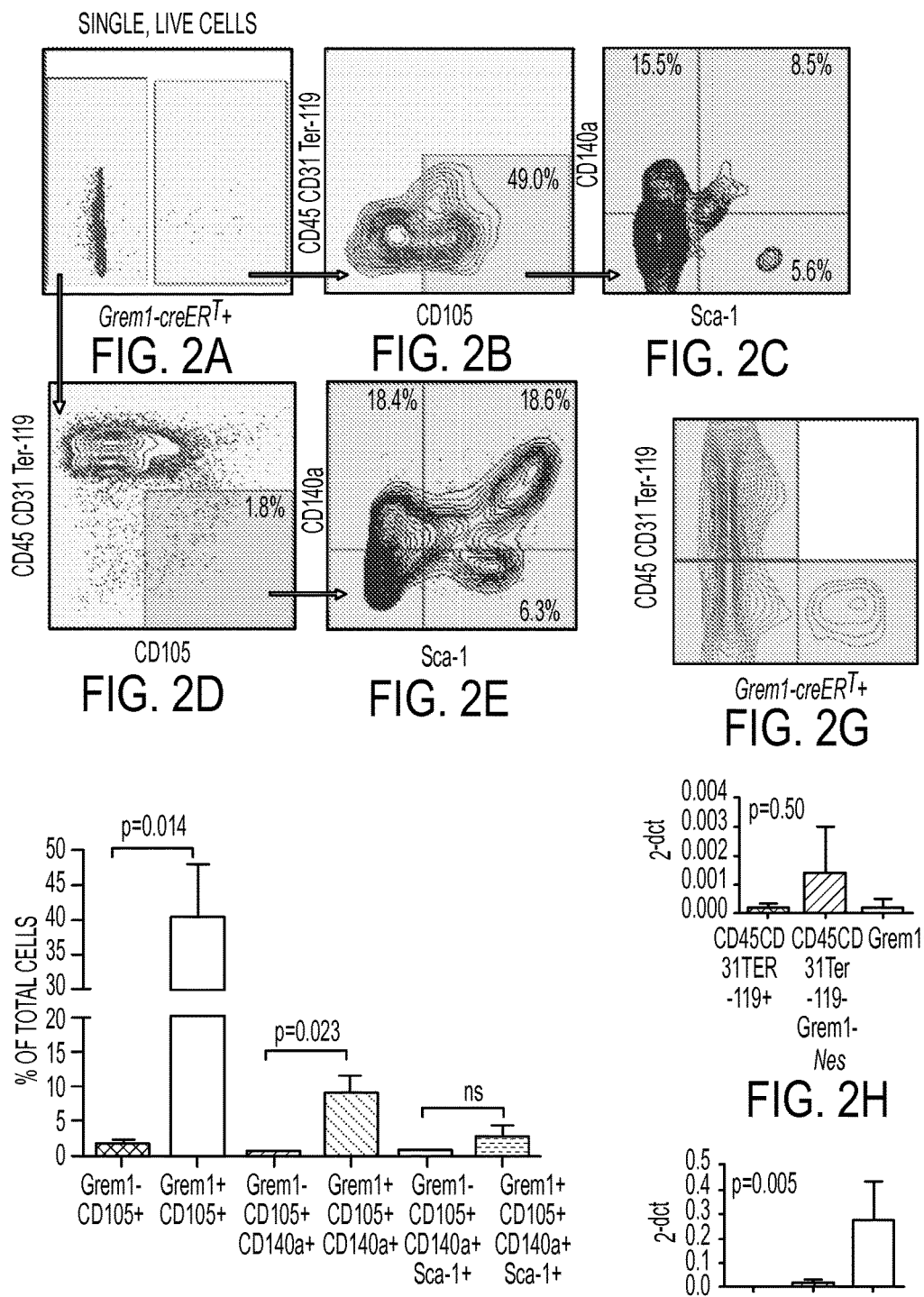

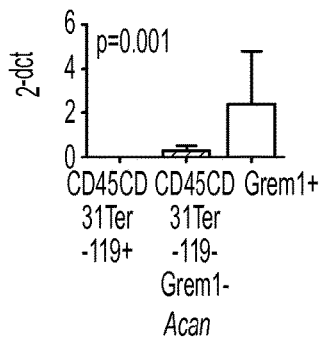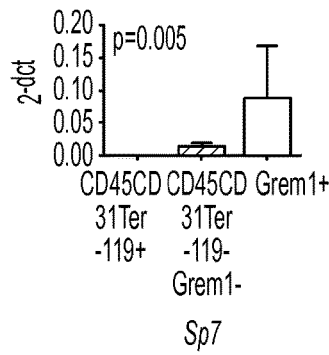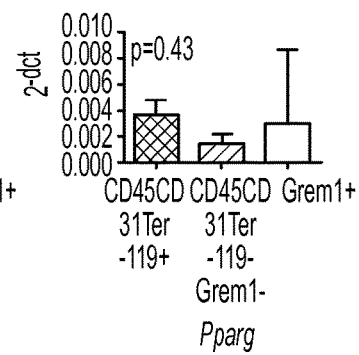
FIG. 2J  FIG. 2K  FIG. 2L
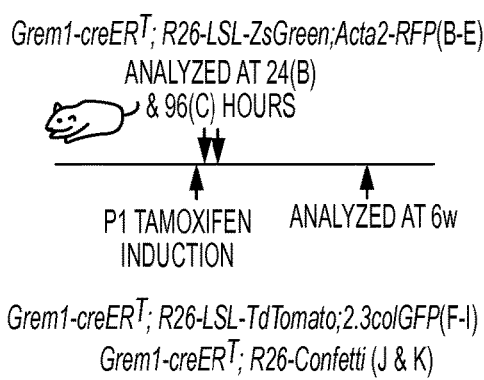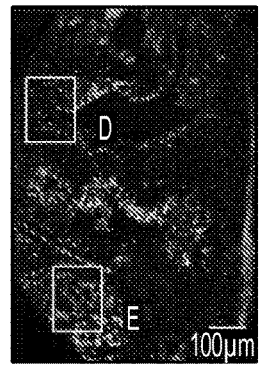
FIG. 3A  FIG. 3B  FIG. 3C
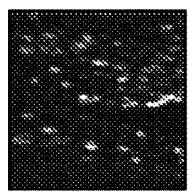
FIG. 3D
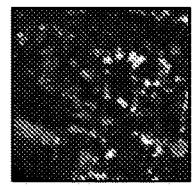
FIG. 3E
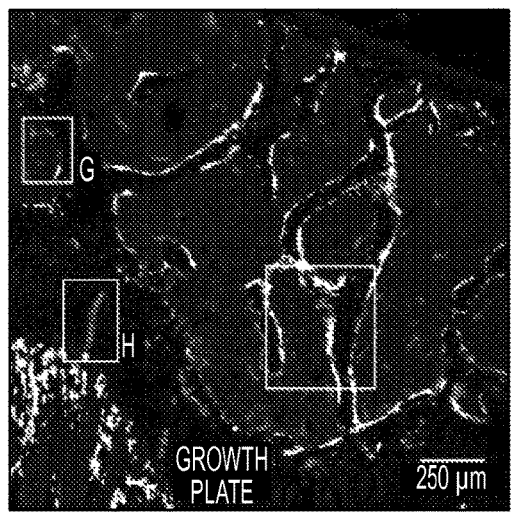
FIG. 3F

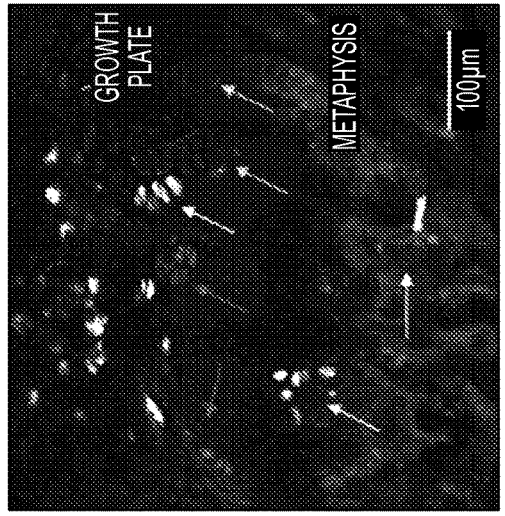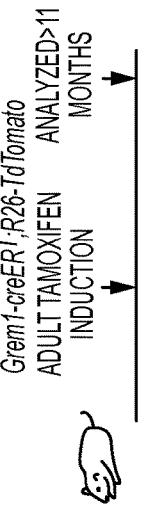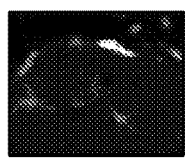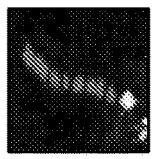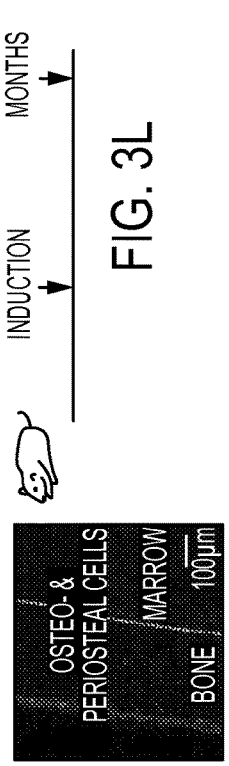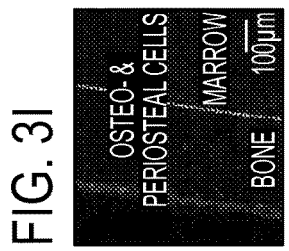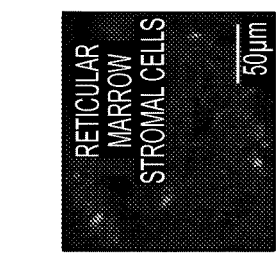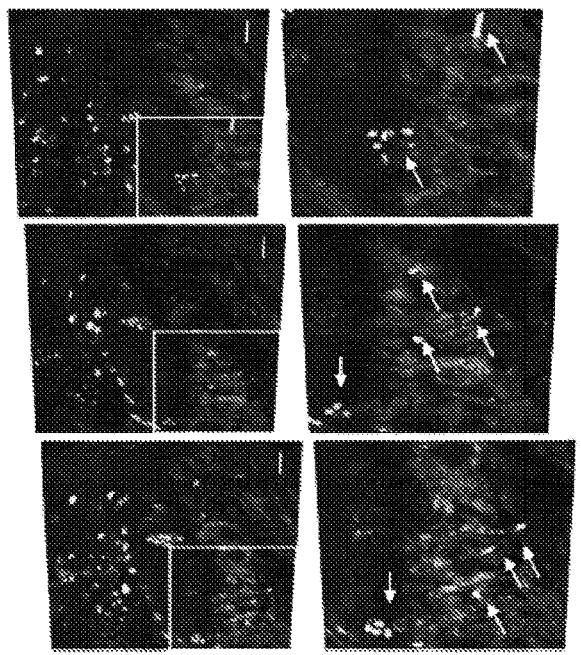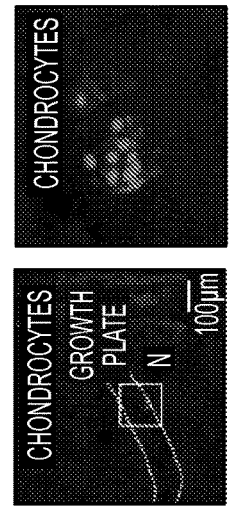

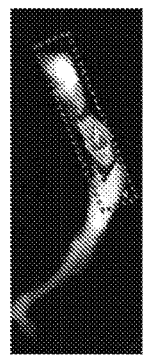
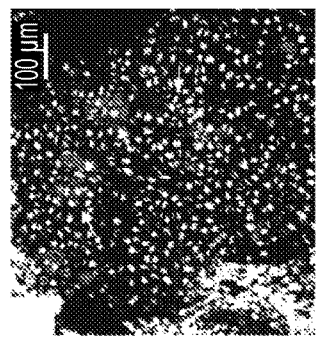
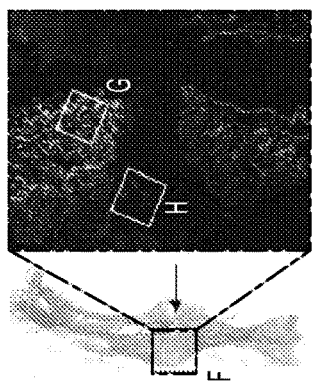
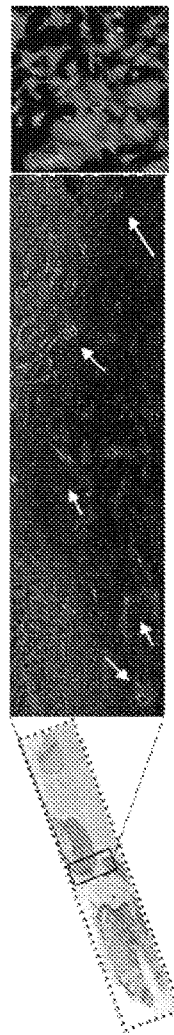
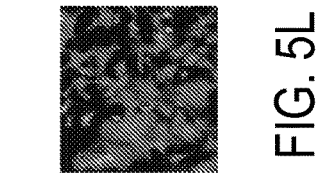
FIG. 5E  FIG. 5F  FIG. 5G  FIG. 5H  FIG. 5J  FIG. 5I  FIG. 5K  FIG. 5L

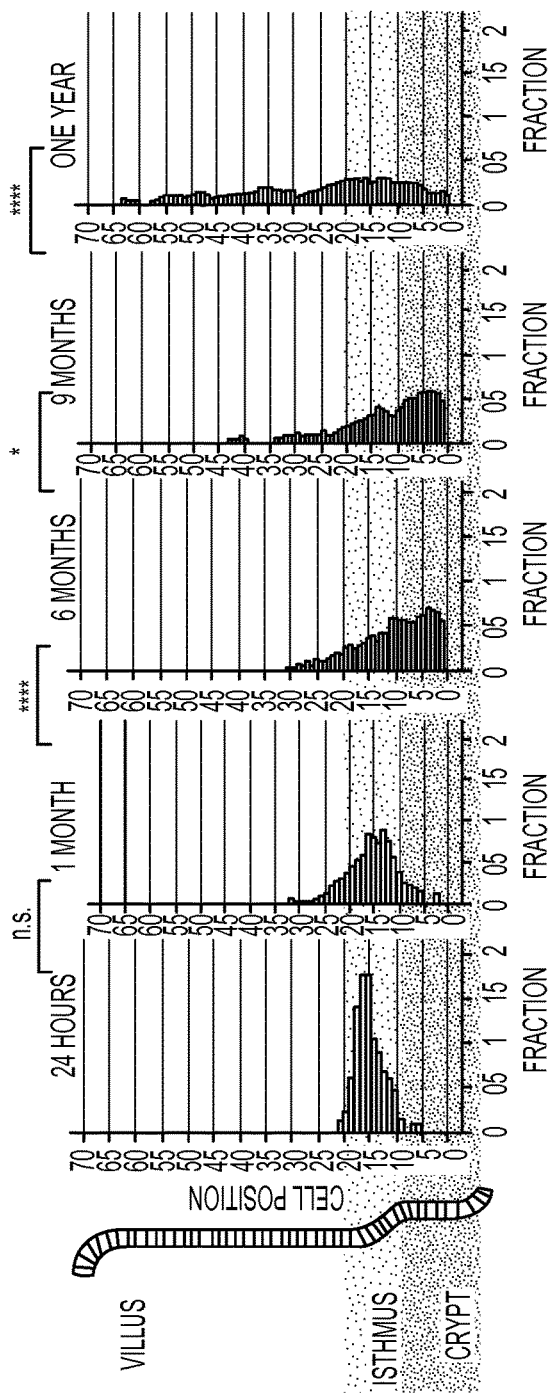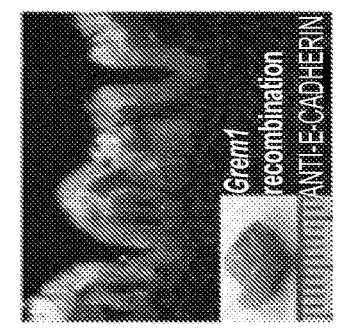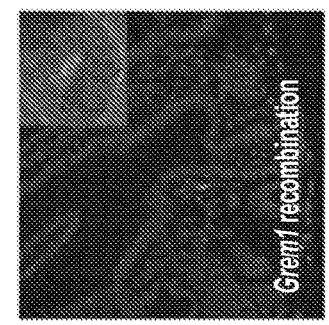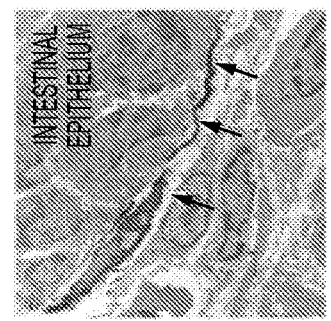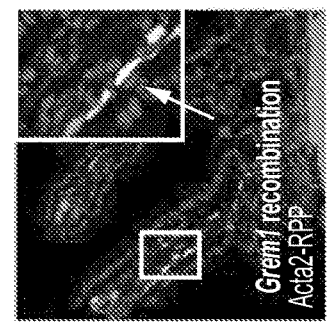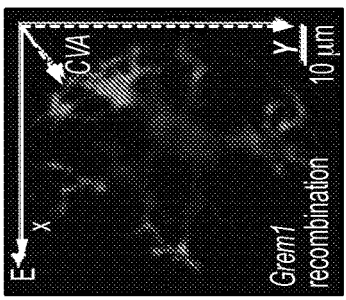

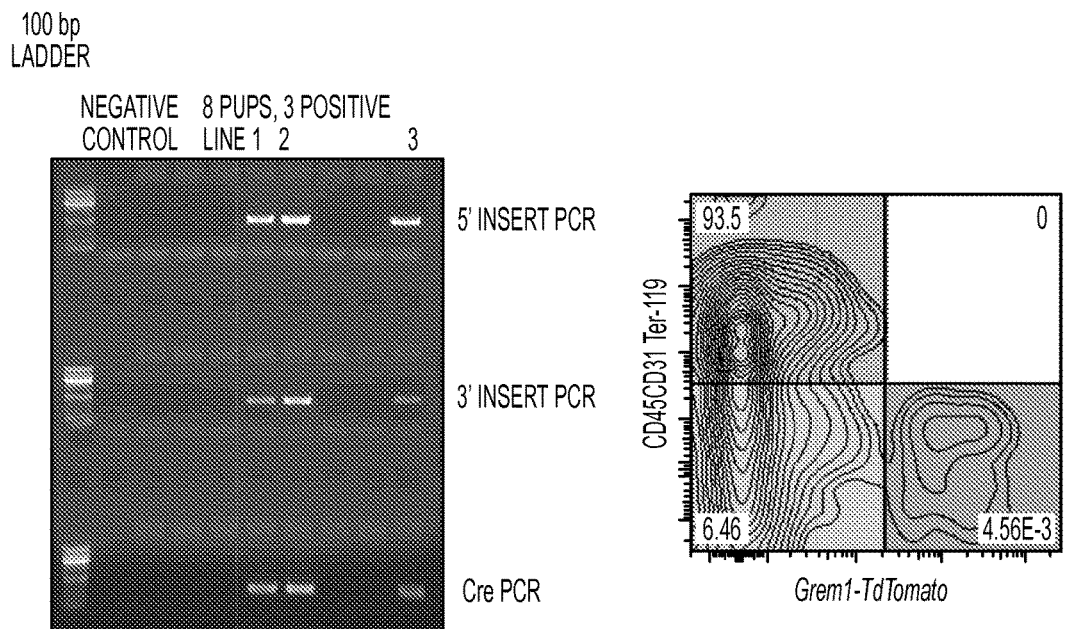
FIG. 8D
FIG. 8E
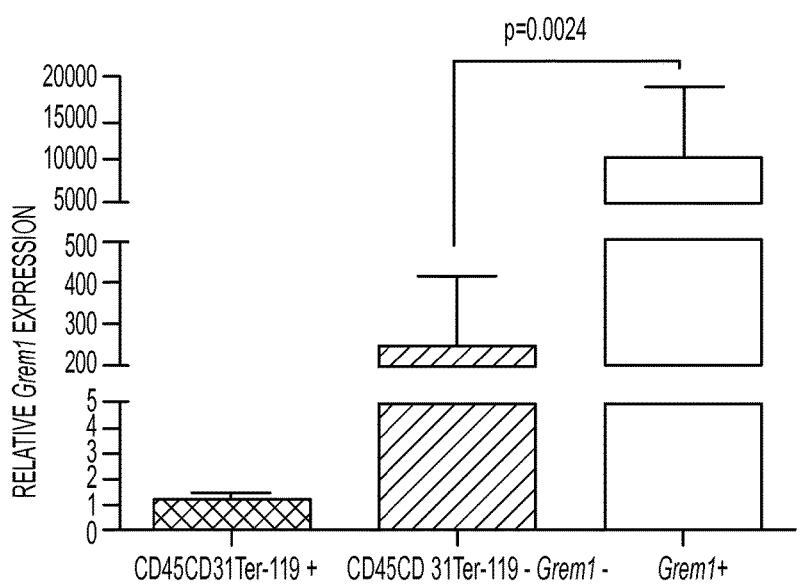
FIG. 8F

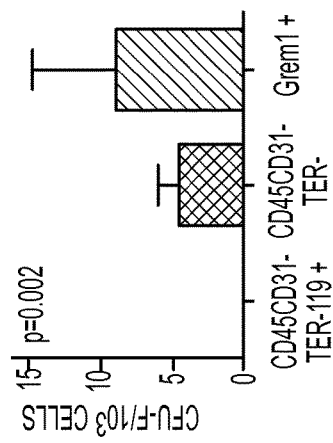
FIG. 10A
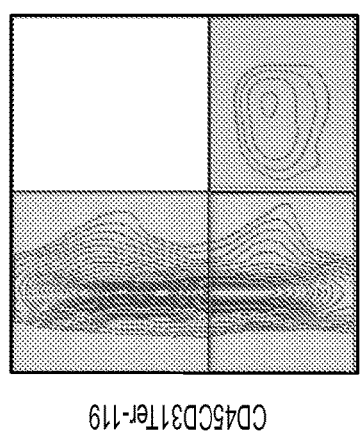
FIG. 10B
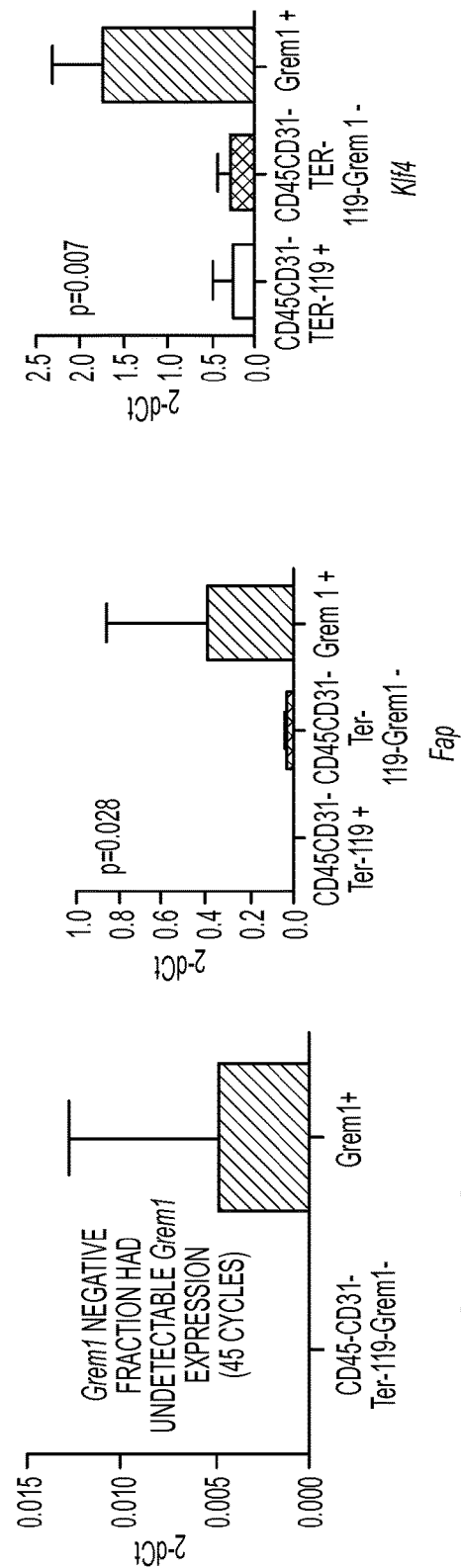
FIG. 10C
FIG. 10D
FIG. 10E

OSTEOCHONDRORETICULAR STEM CELLS FOR BONE AND CARTILAGE REGENERATION

CROSS REFERENCE TO RELATED APPLICATIONS

This application is a 371 national stage application of PCT Application No. PCT/US15/59772, filed Nov. 9, 2015, and claims priority to U.S. Provisional Application Ser. No. 62/077,162, entitled, "Osteochondroreticular stem cells for bone and cartilage regeneration" filed on Nov. 7, 2014, the contents of which are incorporated herein.

STATEMENT OF GOVERNMENT INTEREST

This invention was made with government support under RHL115145A and NIH5U54CA126513 awarded by the National Institutes of Health. The government has certain rights in the invention.

BACKGROUND

Arthritis sufferers include men and women, children and adults. Approximately 350 million people worldwide have arthritis. Nearly 40 million persons in the United States are affected by arthritis, including over a quarter million children. More than 21 million Americans have osteoarthritis. Cartilage and bone deterioration are a common consequence of aging, but poor diet, sedentary lifestyle, excess weight or injury can also result in damaged tissue. Mature cartilage is avascular and doesn't heal well after injury. Surgery is one option for repairing or replacing a damaged joint, but the costs are high and there are also several risks involved in the procedure, such as rejection in the event of joint replacement and infection.

Osteoarthritis describes a disease involving the degeneration in the protective cartilage around bones and occurs to millions of patients worldwide. Osteoarthritis is just one example of cartilage and bone deterioration and is a debilitating disease that affects millions of people. With the aging population, it is expected to continue to be a major disease worldwide. When the protective cartilage wears down, bones can rub together under joint movement, causing pain and stiffness, which may lead to decreased movement and morbidity. Current treatments include non-steroidal anti-inflammatories that can pose cardiovascular and gastrointestinal side effects, narcotics, and physical therapy to alleviate the symptoms. More invasive joint replacement surgeries are needed for severe cases. No cure exists at the moment other than replacement of the joint.

The present invention provides an alternative approach to treatment.

SUMMARY

Inventive embodiments herein are based on the discovery of a newly identified stem cell, the osteochondroreticular (OCR) stem cell that is shown to be the chief origin of cartilage and bone during development. Certain conventional therapies to address bone and cartilage degeneration and injury have utilized pooled mesenchymal stem cells. The novel OCR stem cell population described herein provides significantly improved therapeutic methods and/or implantable products, compared to conventional pooled mesenchymal stem cell populations, particularly for the repair of cartilage due to their superior chondrogenic properties.

Certain embodiments provide improved stem cell therapy methods of treating diseases, degeneration or injury of the bone and cartilage as described herein including but not limited to osteoarthritis, osteoporosis, and bone fractures using OCR stem cells.

It has been determined that OCR stem cells contribute temporally and make lineage-specific contributions to skeletal development and maintenance. These stem cells are isolated from mesenchymal stromal cells found typically in the bone and bone marrow and can be distinguished by expression of Gremlin 1 (Grem1) and/or cell surface markers such as CD200, CD109 and CD105, markers identified through microarray screens. In addition, OCR stem cells are more clonogenic than other mesenchymal stem cells. OCR stem cells are lineage restricted skeletal stem cells that are determined in their skeletal fate and do not give rise to muscle and fat.

Embodiments of the invention also include a method for isolating OCR stem cells. Isolated OCR stem cells are useful in regenerating cartilage or bone tissue. Particularly, OCR stem cells are useful for treatment of diseases, degeneration or injury of the bone and cartilage resulting from age, gender, genes, excess weight, poor diet, sedentary lifestyle, injury or trauma, abnormal metabolism (such as gout and pseudogout), osteoarthritis, infections (such as in the arthritis of Lyme disease), and an overactive immune system (such as rheumatoid arthritis and systemic lupus erythematosus).

A significant percentage but not all of the OCR stem cells express CD105, a well-established marker of bone marrow, (Grem1+CD105 OCR stem cells) and have skeletal tissue fates. Therefore, in certain embodiments, the method comprises the steps of: (a) obtaining multipotent mesenchymal stromal cells from a subject that comprise OCR stem cells and then isolating from the multipotent mesenchymal stromal cells a population of cells that express Gremlin 1 (Grem1) and/or by particular cell surface markers selected from the group consisting of CD200, CD109, and CD105; and (c) isolating OCR stem cells from the bone and/or bone marrow, wherein the isolated OCR stem cells promote regeneration of cartilage tissue and/or bone. In an alternative embodiment, the OCR stem cells may be isolated without necessarily utilizing cell markers, but can be identified retrospectively by their capacity to generate bone and cartilage in vitro (in culture), but poor efficiency for developing into fat cells.

In some embodiments, the isolated Grem1+CD105 OCR stem cells are subjected to conditions that promote differentiation into osteoblasts, chondrocytes, and reticular marrow stromal cells that are useful for regeneration of cartilage tissue for treatment of diseases described herein. The conditions that promote differentiation comprise culturing the OCR stem cells in the presence of medium that comprises certain factors such as one or more bone morphogenic proteins (BMPs).

In addition, certain embodiments of the invention comprise a composition comprising an acceptable carrier and the isolated Grem1+CD105 OCR stem cells described above in this paragraph and throughout the specification. Optionally, the composition may comprise other therapeutic agents. Certain embodiments of the invention also include substantially pure isolated Grem1+CD105 OCR stem cells from tissue such as bone and bone marrow, which express the cell marker Grem1+ and CD105. In other specific embodiments, methods are provided for treating osteoarthritis and bone fracture by administering a therapeutically effective amount of the composition. The composition may be administered to tissue surround the fracture.

These and other features, aspects, and advantages of the present invention will become better understood with regard to the following description, appended claims, and accompanying figures.

DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1A-1K illustrates that Grem1 identifies rare adult multipotent mesenchymal stromal cells. (A) Protocol and (B) Grem1-creER$^T$; R26-LSL-TdTomato; Nes-GFP mouse femur, showing that metaphyseal Nes-GFP+ (green) and Grem1$^+$ cells (red, white arrows) are distinct. (C) Adult Grem1-creER$^T$; R26-LSL-TdTomato bone marrow cells are rare and mesenchymal (CD45$^-$CD31$^-$Ter-119$^-$). (D-G) Adult Grem1-creER$^T$; R26-LSL-TdTomato; Nes-GFP mice: Grem1 and mesenchymal Nes-GFP cells do not overlap, and clonogenicity is greater in the Grem1+ versus the mesenchymal Nes-GFP+ cells (CD45$^-$CD31$^-$Ter-119$^-$). (E and F) 10 cm cell culture dish; (G) n=5, data shown with mean±SD, p=0.013. (H-K) Grem1$^+$ cells from Grem1-creER$^T$; R26-LSL-ZsGreen; Acta2-RFP mice could be clonally expanded in vitro and differentiated into bone (H) (alizarin red), cartilage (I) (toluidine blue), and myofibroblasts (J) (Grem1$^+$ green-derived cells with coexpression of Acta2 [red]), but very limited adipogenesis (oil red) (K). Lower right insets show equivalent stain in a control marrow culture. In all graphs, the data are shown with the mean±SD.

FIG. 2A-2L illustrates that Grem1$^+$ cells are enriched for CD105 bone marrow cells with upregulated osteochondral versus adipogenic gene expression (A-F) n=3, Grem1$^+$ cells from adult, collagenase-digested whole bone and bone marrow were compared to the Grem1-negative population. On average, 40% (95% CI 20%-60%) of all Grem1 cells were CD45$^-$CD31$^-$Ter-119$^-$CD105$^+$ compared to only 1.8% of Grem1-negative cells (F, p =0.014). (C) Grem1$^+$ cells, however, were not further enriched for other MSC markers CD140a and Sca-1. Grem1$^+$ and Grem1-negative cells were compared across the increasingly specific immunophenotypes; data shown with mean±SD. (G) Microarray was performed to compare the Grem1$^+$ (red) to the nonrecombined stromal (CD45$^-$CD31$^-$Ter-119$^-$) population (green); in qPCR, we also sorted and evaluated the CD45CD31Ter-119$^+$ population (blue) that did not contain any recombined cells. (H) Grem1$^+$ cells were not enriched for Nes expression. (I-L) qPCR confirmation of microarray revealed that Grem1$^+$ cells had increased expression of pericytic (Cpsg4; I) and osteochondral genes (Acan and Sp7; J and K) but no association with the adipogenic differentiation gene Pparg (L). In all graphs, the data are shown with the mean±SD.

FIG. 3A-3P illustrates that endogenous Grem1 cells self-renew and lineage trace bone, cartilage, and stroma. (A) Protocol. (B-E) P1 induction in Grem1-creER$^T$; R26-LSL-ZsGreen; Acta2-RFP mice. (B) At 24 hr after tamoxifen, Grem1 recombined (green) only within the primary spongiosa of long bones distinct from the Acta2-RFP (red) cells in the marrow. But, over the following 96 hr (C), the Grem1 cells began organizing into chondrocytic columns (D) and differentiated into stromal cells that invade the bone marrow (E) intertwined with Acta2-positive (red) cells. (F-I) Grem1-creER$^T$;R26-LSL-TdTomato;2.3colGFP mice induced at P1, examined at 6 weeks, show that the Grem1$^+$ cells generate reticular marrow stromal cells (G), chondrocytes in the epiphyseal plate (H), osteoblasts (2.3colGFP$^+$, thus yellow) in the trabecular bone (I). Grem1-creER$^T$;R26-Confetti P1 induction, examined at 6 weeks, revealed clonal populations of chondrocytes, and (K) serial sections confirm mixed clones, yellow clone shown, of chondrocytes and marrow stromal cells, low- and higher-power (inset) images. (L-P) Adult induction in Grem1-creER$^T$; R26-LSL-TdTomato analyzed 11 months after adult induction (L). Grem1$^+$ cells had generated chondrocytes (M and N), reticular marrow stromal cells (O), and bone and periosteal cells (red) (P).

FIG. 5A-5L illustrates that adult Grem1 cells, both endogenous and transplanted, differentiate into osteochondral fracture callus. (A) Protocol. (B and C) Grem1-creER$^T$; R26-LSL-TdTomato; 2.3colGFP mice adult induction: Grem1+ (red) cells were not osteoblasts (green) but were adjacent to each other in situ (B) and during the first week of adherent bone marrow stromal culture (C). (D) is an X-ray of the femoral osteotomy and internal fixation of the bone. (E) and (F) show the serial histology and fluorescent microscopy sections from the resulting fracture callus after the osteotomy. (G) and (H) are magnified from areas shown in (F). Grem1$^+$ cells (red) stream into the fracture site and differentiate into either osteoblasts (G, yellow cells, white arrows) or Sox9+ (white, nuclear stain) chondrocytes (yellow arrows) (H). (I) A Grem1$^+$ clone, after adult induction, was expanded in vitro. An osteotomy with internal fixation was performed in wild-type mice, at which point 500 3 10$^6$ clonal cells (red) were irrigated into the surgical field. Seven days later, the Grem1 clone had engrafted (J), the site of injury was identified by TdTomato fluorescence imaging, and recombined cells (fluorescent red) differentiated into osteoblastic cells (K) (alkaline phosphatase positive cells, red-brown, white arrows) in the callus (sequential fluorescence microscopy and ALP staining performed on the same slide). (L) Callus culture was performed, and the recombined Grem1 cells were easily recovered in vitro and serially transplanted into a secondary fracture (FIG. 12E).

FIG. 6A-6I illustrates that Grem1 expression identifies iRSCs. (A) Protocol. (B and C) Grem1-creER$^T$;R26-mT/mG adult induction identifies rare, single cells at the junction of the crypt and villus in the small intestine (green=Grem1-creERT+, red=Grem1-creER$^T$-negative). Over 1 year, Grem1$^+$ cells expand to renew the entire periepithelial mesenchymal sheath. By 6 months, they are immediately beneath the intestinal stem cells at the crypt base (B and C). Axes are provided to indicate the longitudinal and circumferential axes (x and y), and "CVA" to designate the crypt-villus, or radial, axis. (D) The mesenchymal expansion was plotted relative to the adjacent epithelial position; 20 well-orientated crypt-villus columns were quantified per mouse. n=3-5 mice at each time point; Kruskal-Wallis analysis (p<0.0001) and post-hoc pairwise Mann-Whitney tests, corrected for multiple comparisons, revealed significant differences (****p<0.0001, *p <0.05). (E) The sheath was comprised of a reticulated population of stellate cells with long processes that encircled the entire intestinal gland. This cell encapsulated the very base of the intestinal crypt, similar to the position of the cell identified in (C). (F) The Grem1$^+$ population self-renewed and was multipotent, generating both Acta2 positive (yellow cell, white arrow) and negative fibroblastic lineages. (G) Transmission electron microscopy: the Grem1 lineage (yellow arrows) is immediately beneath the epithelial cells. (H) Tissue engineering: representative images from n=8 small-intestinal organoid unit transplants. Small intestines were harvested from 3-week-old, tamoxifen- induced donor mice. In the donor intestines, prior to harvest, there were single Grem1$^+$ cells (red) near the isthmus of the intestinal gland. After digestion of the donor intestines into organoid units, rare Grem1$^+$ mesenchymal cells (red) were found within individual organoid units (inset). (I) Four weeks after transplantation, TESIs develop, with the periepithelial mesenchymal sheath recapitulated from the donor Grem1$^+$ cells (red). E-cadherin staining (green) was used to identify the epithelium.

FIG. 8A-8F illustrates (A) a candidate panel of genes based on perisinusoidal, niche and important mesenchymal lineage genes. qPCR for each gene was first performed on 100,000 freshly sorted CD45-CD31-Ter119- and then repeated on the same population of cells after 14 days of adherent culture in aMEM plus 10% MSC defined FBS and 1% antibiotics. Represented as fold-change in expression relative to pre-culture levels B, Grem1 was increased 70× in sorted CD45-CD31-Ter119- cells after 14 days of adherent culture, n=7, Wilcoxon rank-sum test, p=0.016*, consistent with a marker of undifferentiated mesenchyme C, Other MSC genes Nes and Cxcl12 were also slightly elevated after culture when compared to their freshly sorted parent population (Mann-Whitney test). All graphs represent mean+/−SD. The increase in post-culture Grem1 expression was significantly greater than the increase found for Cxcl12 expression. The increase in Grem1 expression relative to Nes expression after culture did not reach statistical significance. D, Grem1-creERT: from 8 potential founders we generated 3 founder lines, confirmed by PCR genotyping for the regions of insertion of the creERT into the Grem1 BAC transgene and also primers specific for Cre cDNA. The 5' insertion site PCR was used subsequently for genotyping (Table 2). These founders were generated on a B6CBA/F2 background, which was then backcrossed 6 generations to C57BL/6J. Only one line (line 3) displayed significant recombination following adult tamoxifen induction. Line 3 was confirmed to be specific for endogenous Grem1 function by qPCR (E & F) of sorted bone marrow populations based on mesenchymal markers and Grem1-recombination, represented as fold change relative to the CD45CD31Ter-119 (+) population. Line 3 was used for all experiments and is available at JAX.

FIG. 10A-10L represents (A) color-coded FACS strategy reflected in the color of subsequent graphs, all of which represent mean+/−SD. B, Grem1$^+$ cells, as a single criterion, significantly enriched for bone marrow CFU-Fs in adherent culture (represented as number of CFU-Fs per 1000 cells for each population, p=0.002). C, prior to microarray analysis the RNA from FACS cells had to be amplified. We confirmed that amplification was successful and had not distorted the population we repeated Grem1 qPCR, confirming results from FIG. 8G. Grem1 recombined cells had higher Grem1 expression compared to their Grem1 negative but mesenchymal (CD45-CD31-Ter.-119-) counterparts, in which Grem1 expression was undetectable. D, Support of microarray findings, Grem1-recombination cells had higher expression of Fap and Klf4. F-H. To determine which signaling pathways (Bmp, Tgfb, Pdgf, Fgf) were active within Grem1 cells all differentially expressed genes (fdr<0.05) were assigned to KEGG pathways. These figures show the F, Bmp, and H, Pdgfr/Fgf/Mapk and Vegf I, pathways for which Grem1+ vs. Grem1 negative (mesenchyme) was significantly different with fdr←0.05. F. The genes in the Bmp pathway (Bmp2, Bmp5, Bmp6, Acvr1, and Id2 are all upregulated (red) so that the pathway is activated. On the other hand, in the pathway also F., although all of the genes (Tgfb1, Dcn, and Ltbp1) are also upregulated, Dcn, and Ltbp1 inhibit Tgfb1, so that there is little, if any net upregulation of the pathway. In the Pdgf/Fgf/Mapk pathway (H), Fgf2, Pdgfa, and Fgr1-3 are all upregulated, but their effect is cancelled all or in part, and perhaps even reversed by the down regulation (blue) of their downstream effectors Sos2, and Mapk1/Erk, so that there is little if any activation of this pathway. There is cross-talk between the Pdgf/Fgf/Mapk and Bmp pathways through the downregulation of Mapk1/Erk, but since Mapk1 inhibits this pathway, its downregulation will either activate or leave the Bmp pathway unaffected. I. The Vegf pathways shows a mix of downregulated (blue) and slightly upregulated genes, that fail to generate a coherent signal constituting pathway activation G. Grem1-creER$^T$;R26-LSL-ZsGreen mice (n=4) were induced in adulthood and then examined by flow cytometry for pSmad1,5 positivity, indicative of Bmp signaling. A significantly higher proportion of cells were pSmad1,5+in the Grem1+ vs. the Grem1 negative population. J. Nr2f2 gene expression was on average 4.8 xs higher in the Grem1+ clones (23 clones) vs. polyclonal Nes-GFP derived marrow stromal culture. K. The 23 Grem1+ derived clones revealed relatively homogeneous expression of the important mesenchymal genes Runx2, Sox9, Pparg, Myod and Sp7. L. 100% of the 3 distinct human MSC lines we examined expressed GREW FIG. 11A-11J represents A, Grem1creERT;R26-LSL-Td-Tomato;2.3colGFP mice. P1 induction, by 6 weeks in addition to traced osteoblasts (white arrow) and chondrocytes (not shown in this figure) Grem1+ cells had also traced an extensive network of reticular marrow stromal cells that spanned the endosteal and perivascular areas. These were CD105+ (white), yellow arrows, scale bar=10 µm. B, 4 weeks (P28) following P1 induction, Grem1+ cells give rise to approximately 64% of the bone and 50% of the chondrocytes within the metaphysis and epiphysis, C, Grem1-creERT;R26-LSL-TdTomato adult induction, traced for 11 months, traced articular cartilage, here shown on the articular cartilage on the inferior aspect of the femoral head. D, at 12 months, following adult induction the Grem1 OCR stem cells Grem1-creERT;R26-LSL-ZsGreen mice had generated diaphyseal osteoblasts along the endosteal surface (white arrows) and periosteal cells (yellow arrow). 12 months after adult induction Grem1+ cells, which are green (Grem1-creERT;R26-LSL-ZsGreen mice), did not generate adipocytes in the femur E, or in the vertebrae F. Anti-perilipin immunostaining (red) was used to identify adipocytes. G-J, 11 months after adult induction of Grem1-creERT;R26-LSLTdTomatosingle recombined red clones could be harvested from the bone marrow (G), and then expanded and clonally differentiated in bone, I (alizarin red), and cartilage J, (toluidine blue), but again adipocytic differentiation (oil red) was poor H.

DESCRIPTION

Figure 1G:
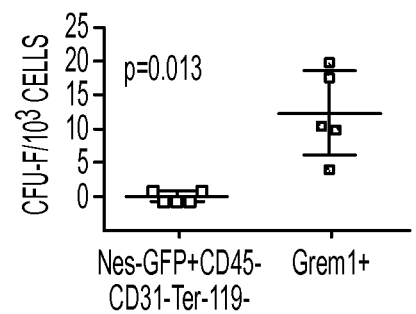

In the Summary above and in the Detailed Description below, in the claims below, and in the accompanying drawings, reference is made to particular features (including method steps) of the invention. It is to be understood that the disclosure of the invention in this specification includes all possible combinations of such particular features. For example, where a particular feature is disclosed in the context of a claim, that feature can also be used to the extent possible, in combination with and/or in the context of other particular aspects and embodiments of the invention, and in the invention generally.

1. Introduction

Regenerative medicine is often described as harnessing the body's regenerative mechanisms in a clinically targeted manner, using the body's capacity to regenerate in ways that are not part of the normal healing mechanism or by artificially amplifying normal mechanisms. Stem cells are pluripotent or multipotent cells with the potential to differentiate into a variety of other cell types, which perform one or more specific functions and have the ability to self-renew. It has been found that stem cells from a variety of sources can be used for multiple therapeutic or prophylactic purposes. For example, mesenchymal stem cells (MSCs) derived from multiple tissues in the adult body are multipotent non-hematopoietic stem cells and are characterized by extensive proliferative ability in an uncommitted state while retaining the potential to give rise to cell types including osteoblasts, myocytes, chondrocytes, adipocytes, endothelial cells and beta pancreatic islet cells. MSCs are present in tissues which arise from the embryonic mesoderm (e.g., hematopoietic cells and connective tissue). Thus, stem cells can be isolated from many tissue sources within the adult body.

The current understanding in skeletal biology is that a MSC exists in the bone marrow, which is the cellular origin of all adult bone, fat and cartilage. MSCs can differentiate into a variety of cell types including cells of connective tissues such as cartilage, muscle, adipose, or tendon. MSCs can be obtained from the bone marrow and can be expanded in vitro.

Arthritis is a degenerative disease in which cartilage cells lose its function over time, leading to inflammation and other complications accompanied by the loss of cartilage surface on bones, ligaments and joints. Stem cells may be used for orthopedic application including treatment of treatment of cartilage damage in joints caused by osteoarthritis, aging, and/or mechanical injury.

Described herein is the discovery that there is an alternate stem cell, the osteochondroreticular stem cell, that is the chief origin of cartilage and bone during development and that traditional mesenchymal stem cells, contribute very little to cartilage. Current approaches for cellular therapy in bone and cartilage regeneration and repair have utilized pooled mesenchymal stem cells. The novel stem cell population described herein provides improved benefits over other stem cells, particularly for the repair of cartilage.

The new stem cell described herein is called the "osteochondroreticular stem cell" and can be identified and isolated from the bone by expression of the gene Gremlin 1 and/or by particular cell surface markers including, but not limited to, CD200, CD109, CD105. These markers were identified through the process of microarray screens and flow cytometry experiments. These and related markers identified from the screen can be used to isolate human osteochondroreticular stem cells. Described herein is data showing these cells in mice are easily propagated in culture, behave differently to traditional mesenchymal stem cells, are more chondrogenic, and can be easily transplanted into fracture.

The utility for this discovery is vast for treatment of osteoarthritis. Osteoarthritis describes a degenerative disease whereby the cartilage surrounding tissue at joints wears down, leading to rubbing of bones (Noth U, Steinert A, Tuan R. "Technology Insight: Adult Mesenchymal Stem Cells for Osteoarthritis Therapy." Nat Clin Pract Rheumatol. 2008; 4 (7):371-380). Symptoms of osteoarthritis include pain and decreased motility in the joint. Current methods of treatment include pain killers to alleviate symptoms and invasive joint replacement surgery for severe cases. Stem cells are cells that can be differentiated into any type of cell depending on the stimulus given. Mesenchymal stem cells have osteogenic (bone) and condrogenic (cartilage) potential (Solchaga L, Penick K, and Welter J. "Chondrogenic Differentiation of Bone Marrow-Derived Mesenchymal Stem Cells: Tips and Tricks." Methods Mol Biol. 2011; 698:253-278). Clinical trials are under way to test the viability of using mesenchymal stem cells to generate cartilage in joints where arthritis is present (Jo C, Lee Y, Shin W, et al. "Intra-Articular Injection of Mesenchymal Stem Cells for the Treatment of Osteoarthritis of the Knee: A Proof-of-Concept Clinical Trial." Stem Cells. 2014; 32:1254-1266).

Knee osteoarthritis is a chronic, debilitating condition affecting more than 250 million people world wide (Buchbinder, R. Meniscectomy in Patients with Knee Osteoarthritis and a Meniscal Tear? N Engl J Med 2013; 368:1740-1741). Unfortunately, arthroscopic surgical approaches for this condition are no superior to sham procedure and physical therapy alone (Katz J N, Brophy R H, Chaisson C E, et al. Surgery versus physical therapy for a meniscal tear and osteoarthritis. N Engl J Med2013;368:1675-1684). Prosthetic joint replacement is the only viable approach for many patients with severe disease. Joint replacement is expensive, complicated and is associated with many specific complications including, infection, joint failure and venous thromboembolism. Despite its limited efficacy, arthroscopy continues to be performed throughout the Western world. Delivery of an effective cellular therapy for osteoarthritis at the time of arthroscopy, would provide enormous benefit to patients and would be of great value.

There are current clinical trials proceeding looking at the role of allogeneic mesenchymal stem cells for use in knee osteoarthritis (NCT01453738), but pooled MSCs are less chondrogenic than osteochondroreticular stem cells and expansion of the most chondrogenic fraction for delivery, the osteochondroreticular stem cells described herein, has the greatest opportunity for clinical success.

Accordingly, described herein are methods of identifying and/or isolating osteochondroreticular stem cells. These stem cells are isolated typically from bone tissue and can be distinguished by expression of Gremlin 1 and/or cell surface markers such as CD200, CD109 and CD105, markers identified through microarray screens. Osteochondroreticular stem cells behave differently from mesenchymal stem cells in that they are more chondrogenic.

Also described herein are therapeutic methods to regenerate the cartilage tissue for treatment of osteoarthritis. It has been determined that OCRs possesses strong chondrogenic potential (able to develop into cartilage) than previously investigated mesenchymal stem cells. The OCRs can be used to developed treatment of osteoarthritis or other diseases where cartilage re-generation would be beneficial.

Use of these stem cells can regenerate cartilage between bones to alleviate pain and stiffness associated with osteoarthritis. For example, OCR stem cells can be administered directly into joints affected by osteoarthritis. Alternatively, OCR stem cells can be differentiated into cartilage in culture to aid in study of cartilages or production of cell-based implants for implantation into joints or bone structures.

In one embodiment isolated OCR stem cells can be expanded, enriched for chondrogenic properties, and used for subsequent injection into joints suffering from osteoarthritis or for application onto or into the bone either to treat or even potentially to prevent fracture in high risk patients.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

2. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N. Y. (2000). Unless defined otherwise, all technical and scientific terms used herein have the same meaning as commonly understood by one of ordinary skill in the art.

The term "acceptable carrier" as used herein, means excipients, emollients, and stabilizers or stabilizing agents or other acceptable materials, compositions, or structures involved in holding, carrying, transporting, or delivering any subject cell or composition. Each means must be "acceptable" in the sense of being compatible with the other ingredients of a subject composition and not injurious to the subject.

The term "administering" as used herein, means delivery, for example of an OCR stem cell to a subject.

The term "bone tissue" as used herein is tissue that includes bone or bone marrow.

The terms "express," "expression," and "expressing," as used herein with respect to gene products, indicate that the gene product of interest is produced by the cell at a detectable level. "Significant expression" refers to expression of the gene product of interest to 10% above the minimum detectable expression. Cells with "high expression" or "high levels" of expression of a given expression product are the 10% of cells in a given sample or population of cells that exhibit the highest expression of the expression product. Cells with "low expression" of a given expression product are the 10% of cells in a given sample or population of cells that exhibit the lowest expression of the expression product (which can be no expression).

The terms "isolated," "isolating," "purified," "purifying," "enriched," and "enriching," as used herein with respect to cells, means that the OCR stem cells at some point in time were separated, sorted and capable of directed differentiation. "Highly purified," "highly enriched," and "highly isolated," when used with respect to cells, indicates that the cells of interest are at least about 70%, about 75%, about 80%, about 85% about 90% or more of the cells, about 95%, at least 99% pure, at least 99.5% pure, or at least 99.9% pure or more of the cells, and can preferably be about 95% or more of the differentiated cells.

The term "multipotent" as used herein, refers to a property of any stem cell or progenitor cell, meaning that it has the ability to differentiate into two or more different cell types. Pluripotent stem cells, such as embryonic stem cells, can give rise to all of cell types, thus multipotent cells are less potent than pluripotent cells. Adult stem cells are considered multipotent.

The term "osteochondroreticular stem cell" or "OCR stem cell" as used herein, refers to lineage-specific Grem1+ skeletal stem cells. OCR stem cells typically reside within the bone or bone marrow.

The term "population" as used herein when used with respect to cells, means a group or collection of cells that share one or more characteristics. The term "subpopulation," when used with respect to cells, refers to a population of cells that are only a portion or "subset" of a population of cells.

The term "progenitor cell" is a cell that, like a stem cell, has a tendency to differentiate into a specific type of cell, but is already more specific than a stem cell and is pushed to differentiate into its "target" cell. In certain embodiments, the OCR stem cell is a lineage-specific progenitor cell that is pushed to differentiate into osteoblasts, chondrocytes, and reticular marrow stem cells, but not adipocytes.

The term "skeletal cell sample" as used herein means, a cell sample obtained from bone tissue. Skeletal cell samples include multiple cell types including OCRs. OCRs are isolated utilizing the techniques herein such as sorting based on Grem1 expression.

The term "stem cells" (or blank cells) are undifferentiated cells that can divide or differentiate into specialized cells, replacing dying cells or damaged tissues. There are two broad types of stem cells: embryonic stem cells (ESCs) and adult stem cells (somatic stem cells).

The terms "subject," "host," and "patient," as used herein, are used interchangeably and mean a mammalian animal being treated with the present compositions, including, but not limited to, vertebrates, simians, humans, felines, canines, equines, rodents (including rats, mice and the like), bovines, porcines, ovines, caprines, mammalian farm animals, mammalian sport animals, and mammalian pets.

The terms "substantially pure," "substantially purified," and "substantially enriched" as used herein with respect to cells means the isolated cell population of cells that includes at least 80% pure, and preferably at least 85% pure, at least 90% pure, at least 95% pure, at least 97% pure, at least 98% pure, at least 99% pure, at least 99.5% pure, or at least 99.9% pure cells of the type in question, for example, Grem1+OCR stem cells. Percentage purity refers to the percentage of the cell type in question relative to all cells in the sample.

As used herein, a "therapeutic agent" means a compound or molecule capable of producing an effect. Preferably, the effect is beneficial.

As used herein, "therapeutically effective amount" means an amount sufficient to treat a subject.

As used herein, the terms "treatment," "treating," and "treat" and the like, as used herein refer to obtaining a desired medical effect. The effect may be prophylactic in terms of completely or partially preventing a condition (i.e., disease, degeneration, disorder or injury) or symptom thereof and/or may be therapeutic in terms of a partial or complete cure or repair of the condition and/or adverse effect attributable to the same. "Treatment," includes any treatment of a condition in a mammal, particularly in a human, and includes: (a) preventing the condition or disease or symptom thereof from occurring in a subject which may be predisposed to the condition or disease but has not yet been diagnosed as having it; (b) inhibiting the condition or symptom thereof, such as, arresting its development; and (c) relieving, alleviating or ameliorating the condition or symptom thereof, such as, for example, causing regression of the condition or symptom thereof.

3. Overview

The newly-identified OCR stem cells are integrally involved in maintenance and repair of the postnatal skeleton. One model that has been previously suggested is that perisinusoidal mesenchymal stem cells (MSCs) give rise to osteoblasts, chondrocytes and marrow stromal cells, as well as adipocytes. However, the existence of such an endogenous MSC has not been proven through fate-mapping experiments. The discovered OCR stem cells that express the BMP antagonist gremlin 1 (Grem1) are found in bone and bone marrow. OCR stem cells self-renew and generate osteoblasts, chondrocytes and reticular marrow stromal cells, but not adipocytes. In adulthood, OCR stem cells are concentrated within the metaphysis of long bones and are distinct from traditional perisinusoidal, nestin-expressing MSCs. OCR stem cells are important for bone development, adult skeletal homeostasis and fracture repair, while nestin+ MSCs contribute little to skeletogenesis. Incidentally, it has been discovered that Grem1 expression also identifies intestinal reticular stem cells (iRSCs) that can be transplanted and are the cell of origin for the periepithelial intestinal mesenchymal sheath.

Furthermore, OCR stem cells, when transplanted to a fracture site, contribute to bone repair. It is therefore possible that drugs or other therapies can be developed to stimulate the production of OCR stem cells and improve the body's ability to repair bone injury-a process that declines significantly in old age. These cells are particularly active during development, but they also increase in number in adulthood after bone injury. The study also showed that the adult OCR stem cells are distinct from MSCs, which play a role in bone generation during development and adulthood. Researchers presumed that MSCs were the origin of all bone, cartilage, and fat, but recent studies have shown that these cells do not generate young bone and cartilage. Without being bound by theory, OCR stem cells actually fill this function and that both OCR stems cells and MSCs contribute to bone maintenance and repair in adults.

Described herein are methods of identifying and/or isolating OCR stem cells. These stem cells are isolated typically from bone tissue and can be distinguished by expression of Gremlin 1 and/or cell surface markers such as CD200, CD109 and CD105, markers identified through microarray screens. Osteochondroreticular stem cells behave differently from mesenchymal stem cells in that they are more clonogenic and chondrogenic.

Also described herein are therapeutic methods to regenerate the cartilage tissue for treatment of osteoarthritis. It has been determined that OCRs possesses strong chondrogenic potential (able to develop into cartilage) than previously investigated mesenchymal stem cells. The OCRs can be used to developed treatment of osteoarthritis or other diseases where cartilage re-generation would be beneficial.

Use of these stem cells can re-generate cartilage between bones to alleviate pain and stiffness associated with osteoarthritis. For example, OCR stem cells can be administered directly into joints affected by osteoarthritis. Alternatively, OCR stem cells can be differentiated into cartilage in culture to aid in study of cartilages or production of cell-based implants for implantation into joints or bone structures. Further, the method by which OCRs were identified (through microarray screens) can be used to identify other types of stem cells that have chondrogenic potential.

In one embodiment, isolated OCR stem cells can be expanded, enriched for chondrogenic properties, and used for subsequent injection into joints suffering from osteoarthritis or for application onto or into the bone either to treat or even potentially to prevent fracture in high risk patients.

A specific method embodiment disclosed herein involves isolating OCR stem cells that promote regeneration of cartilage tissue useful for treatment of diseases of the bone and cartilage involving the steps of extracting bone and/or bone marrow from a subject, identifying the OCR stem cells by expression of the gene Gremlin 1 (Grem1) and/or by particular cell surface markers and isolating OCR stem cells from the bone and/or bone marrow. .

In the identification step, the OCR stem cells are identified by expression of the gene Gremlin 1 (Grem1) and/or by particular cell surface markers CD200, CD109, and CD105. These markers can be identified through the process of microarray screens and flow cytometry experiments as described herein in Example 2 and FIG. 2. These and related markers identified from the screen can be used to isolate the OCR stem cells to promote regeneration of cartilage or bone. An inducible Cre line, driven by the enhancer elements of the BMP antagonist Grem1, was generated to identify and trace rare skeletal stem cells in vivo. Adult Grem1 osteochondroreticular (OCR) stem cells were found beside the growth plate and the trabecular bone, where they generated and maintained articular and growth plate cartilage, bone and reticular marrow stromal cells, but not fat.

4. Detailed Description Of The Embodiments

The discovery of a new Grem-1+cell type, herein referred to as OCR stem cells, which is programmed to produce certain cell types, namely bone and cartilage cells, leads to a number of therapeutic possibilities. Accordingly, methods of isolating OCR stem cells, compositions and kits comprising them, are provided. Methods for treating diseases relating to damaged cartilage or bone are also provided, such as administration via direct injection into a joint to help repair cartilage, injection into subchondral defects, bone fractures, and the engineering various cell-based scaffolds for implantation for bone or cartilage repair, or bone paste materials. See, for example, U.S. Patent Pub. No. 20140147419.

A. Methods of Isolating OCR Stem Cells for Generation of Bone and Cartilage

Certain embodiments described herein relate to for isolating OCR stem cells that promote regeneration of cartilage tissue useful for treatment of diseases of the bone and cartilage resulting from age, gender, genes, excess weight, poor diet, sedentary lifestyle, injury or trauma (leading to degenerative arthritis), abnormal metabolism (such as gout and pseudogout), inheritance (such as in osteoarthritis), infections (such as in the arthritis of Lyme disease), and an overactive immune system (such as rheumatoid arthritis and systemic lupus erythematosus). The lineage restricted progenitor cells, or OCR stem cells express CD105, a well-established marker of bone marrow, (Grem1+CD105 OCR stem cells) and have skeletal tissue fates. Therefore, in certain embodiments, the method comprises the steps of: (a) identifying a subject in need of cartilage or bone repair; (b) extracting bone and/or bone marrow from a subject; (c) identifying the OCR stem cells by expression of the gene Gremlin 1 (Grem1) and/or by particular cell surface markers selected from the group consisting of CD200, CD109, and CD105; and (c) isolating OCR stem cells from the bone and/or bone marrow via enzymatic digestion wherein the isolated OCR stem cells promote regeneration of cartilage tissue and/or bone.

In some embodiments, the isolated Grem1+CD105 OCR stem cells are subjected to conditions that promote differentiation into osteoblasts, chondrocytes, and reticular marrow stromal cells that are useful for regeneration of cartilage tissue for treatment of diseases described herein. The conditions that promote differentiation comprise culturing the OCR stem cells in the presence of medium that comprises bone morphogenic protein (BMP). Other embodiments include using the immunophenotype of OCR stem cells or the presence of Grem1 expression to isolate these cells.

Extraction and Isolation of OCR Stem Cells

OCR stem cells are obtainable from bone marrow by minimally invasive techniques and can be expanded in culture and permitted to differentiate into the desired lineage. OCR stem cells can be isolated based either on surface markers ('prospectively') or by establishing clonal adherent cultures. As long as clonogenicity assays remain the mainstay of characterization of cells isolated based on surface markers, and as long as cell culture remains necessary prior to transplantation in vivo, isolation by either surface marker or by adherence and clonogenicity yield essentially identical results.

In a select embodiment, the method comprises preparing a cell suspension from bone marrow. Such a cell suspension generally comprises OCRs and is separated from the cell suspension using any convenient method known in the art, for example, a fluorescence-based sorting techniques and expression labels. Suitable labels include, but are not limited to green fluorescent protein (GFP), varieties of other fluorescent proteins including yellow and red, other optical labels utilized for cell separation whose expression is driven by a Grem promoter, Grem1, or other cell surface markers whose expression is highly correlated with the expression of GFP or its derivatives, or Grem1, or both. Anti-Grem1 antibody is preferred.

Techniques for labeling, sorting, fluorescence activated cell sorting (FACS), and enrichment of cells are well known in the art. Useful examples are described in WO 2001/022507 and U.S. application Ser. No. 13/391,251 (US 2012-0220030 A1), which are hereby incorporated by reference in their entirety, and specifically for their description of cell labeling, sorting, and enrichment. The cells can be identified, separated, and/or enriched based on cell markers. It will be understood by those of skill in the art that the stated expression levels reflect detectable amounts of the marker protein on the cell surface. Generally, cell markers can be assessed by staining or labeling cells with probes that specifically bind the marker of interest and that generate a detectable signal.

Differentiation

OCR stem cells can be cultured by a variety of means known to the art. For example, OCR stem cells can be plated (e.g., about 100,000 cells per well) for 2D culture. As another example, OCR stem cells can be centrifuged (e.g., about 2 million cells) to form a 3D pellet. Monolayer (2D) or 3D cell pellets can be cultured in a suitable growth medium. Methods of culturing OCR stem cells are generally known in the art and such methods can be adapted so as to provide optimal conditions for differentiation. OCR stem cells can be induced to differentiate in a first medium (e.g., a medium with serum and missing BMP) and then expanded in a second medium (e.g., a medium with BMP).

OCR stem cells can be expanded on an expansion medium. An expansion medium would usually be simply the base media (alphaMEM plus 10% fetal calf serum), that could include additives depending on the desired differentiation for the expanded cells. If just expanding the cells, the "base media" would be sufficient.

Differentiation can be induced by the application of specific growth factors. The transforming growth factor beta (TGF-beta) superfamily member proteins such as the bone morphogenetic proteins (BMPs) are important factors of chondrogenic and osteogenic differentiation.

Differentiation of OCR stem cells to the osteogenic lineage may be achieved by culture in osteogenic medium. For example, OCR stem cells are seeded at $3,000/cm^2$ in maintenance medium (DMEM, 1 g/l glucose, 10% FCS, 2 mM L-glutamine, 50 U/ml penicillin and 50 U/ml streptomycin) in 6-well, 12-well and chamber slides for 24 h before changing to osteogenic media (maintenance medium, 10 nM dexamethasone, 25 µg/ml ascorbic acid and 10 mM β-glycerophosphate). Cells are then maintained for up to 28 days with a media change every 3-4 days. After 14 days cells in the chamber slides may be fixed in 4% PFA and stored at 4.0 in PBS for immunohistochemistry. After 14 and 28 days the cells are stained with alizarin red S for calcium, and von Kossa for calcium phosphate. RNA may also be extracted for analysis using the Nucleospin RNA extraction kit according to the manufacturer's instructions (Macherey Nagel) and protein samples may be extracted for analysis.

Differentiation of OCR stem cells to the chondrogenic lineage in certain embodiments may be achieved by culture in chrondrogenic medium. For example, OCR stem cells are counted and resuspended at $5 \times 10^5$ cells/ml in chondrogenic media (DMEM with Cambrex chondrogenic single aliquots) with or without 10 ng/ml TGF.quadrature.3 (Cambrex) and then 500 ml aliquots were put into 15 ml tubes before centrifugation at 150.times.g at room temperature for 10 min and incubated at 37° C. for 2 days. After two days the tubes will contain loose round pellets. Pellets are maintained for 21 days with a media change every 3-4 days before RNA is isolated using Trizol (Invitrogen) or cell pellets are fixed in 4% PFA and embedded for cryosectioning. Serial sections are made before slides are stored at -80 degrees Celsius for immunohistochemistry.

Any suitable method of culturing ORC stem cells may be used, and any suitable container may be used to propagate ORC stem cells. Suitable containers include those described in US Patent Publication US2007/0264713 (Terstegge). Containers may include bioreactors and spinners, for example. A "bioreactor" is a container suitable for the cultivation of eukaryotic cells, for example animal cells or mammalian cells, such as in a large scale. A typical cultivation volume of a regulated bioreactor is between 20 ml and 500 ml.

Bioreactors may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. While some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed. In preferred embodiments, cloning cylinders are used.

Expansion of OCR Stem Cells

Expansion of OCR stem cells refers to the increase in population of OCR stem cells in a culture, achieved through cell division. In some embodiments, OCR stem cells are obtained by culture of bone marrow stromal cells alone or in the presence of BMP for sufficient time to expand a single MSC to a population of more than $1 \times 10^3$ stem cells. The culture may initially contain more than one OC stem cell. The culture time to expand the OCR stem cells may be between 5 and 50 days, more preferably between 10 and 45 days and more preferably less than one of 45 days, 40 days, 35 days, 30 days, 25 days, 20 days or 15 days.

In some embodiments, cultures may also comprise other cells, e.g. non-stem cells associated with the stem cells in the tissue from which the stem cells are collected, and/or supporting cells, e.g. feeder cells. Cells used to initiate a culture of stem cells will preferably contain a high proportion of the respective stem cells, e.g. at least 60% stem cells, more preferably one of at least 70% stem cells, 80% stem cells, 90% stem cells, 95% stem cells, 96% stem cells, 97% stem cells, 98% stem cells, 99% stem cells or 100% stem cells. Cells, e.g. cells collected from previous cell culture or from live animals or humans, may be enriched prior to initiating cell culture, e.g. by enriching for markers such as Grem1 CD200, CD109, and CD105 Marker enrichment may be performed by cell sorting, e.g. FACS. In a specific embodiment, OCR cells are sorted using the Smartflare system (Millipore) based on Grem1 expression (www.em-dmillipore.com/US/en/life-science-research/genomic-analysis/SmartFlare-Live-Cell-RNA-Detection/ZdGb.qB.KCcAAAFLAQs0i.s1,nav).

OCR stem cells described herein may be cells from any type of animal. Preferably they are mammalian. In some embodiments they are human. In other embodiments they are from a non-human mammal. The non-human mammal may be a domestic pet, or animal kept for commercial purposes, e.g. a race horse, or farming livestock such as pigs, sheep or cattle. Non-human mammals include rabbits, guinea pigs, rats, mice or other rodents (including any animal in the order Rodentia), cats, dogs, pigs, sheep, goats, cattle (including cows, e.g. dairy cows, or any animal in the order Bos), horse (including any animal in the order Equidae), donkey, and non-human primates.

The culture methodology described above is preferably performed in vitro. The term "in vitro" is intended to encompass experiments with cells in culture whereas the term "in vivo" is intended to encompass experiments with intact multi-cellular organisms.

In certain embodiments, culture of cells in the presence of a factor, such as BMP refers to culture of cells under conditions in which the cells being cultured are able to come into contact with the factor. In preferred embodiments this comprises culturing cells in culture media containing the factor. The culture media may be fluid, e.g. liquid or gel, and may contain MBP in addition to the normal nutrients, growth factors and matrix material. The factor will preferably be present in non-trace amounts. For example, the concentration of the factor in the culture media may range between about 1.0 ng/ml culture media to about 1000 ng/ml culture media. More preferably, the concentration of the factor in the culture media may be between about 5 ng/ml culture media and 200 ng/ml culture media, or between about 20 ng/ml culture media and 170 ng/ml culture media.

As mentioned above, cell culture media may include growth factors, cytokines, hormones, and various nutrients. Illustrative growth factors may include transforming growth factor-beta (TGF-β), fibroblast growth factors (FGFs), insulin like growth factors (IGFs), bone morphogenic proteins (BMPs); illustrative cytokines may include cytokine-like 1 (Cyt11); illustrative hormones may include human growth hormone (HGH); and testosterone; and illustrative nutrients may include ascorbic acid, pyruvate, hyaluronic acid and amino acids.

The properties of cells obtained from culture in the presence of a factor, such as BMP, may be compared against cells of the same type obtained from culture in control conditions. "Control conditions" or "control culture" refers to culture of the cells under conditions in which the cells being cultured do not come into contact with the factor. As such, control conditions may comprise culture in culture media that contains the normal nutrients, growth factors and matrix material but no factor. Examples of control culture media for culture of OCR stem cells include serum free media such as that Brunner, D., et al., "Serum-free cell culture: the serum-free media interactive online database," ALTEX 27(1), 53-62, 2010. Other culture conditions known in the art are disclosed in Panagiota, A., et al., "Characterization of the Optimal Culture Conditions for Clinical Scale Production of Human Mesenchymal Stem Cells", Stem Cells, 2005.

Exemplary maintenance media for cell culture in certain embodiments may comprise DMEM, 1,000 mg/l glucose supplemented with 10% fetal bovine serum (FBS) with 0.1% penicillin/streptomycin and 2 mM L-glutamine at 37° C. in a humidified 5% $CO_2$ incubator. Media may be changed at three-day intervals and the cells subcultured every 4-5 days (about 80% confluency).

B. Isolated OCR Stem Cells

Isolated Grem1+, and optionally CD105+, OCR stem cells, are made according to the methods described above, in this paragraph and throughout the specification. Preferably, the isolated Grem1+, and optionally CD105+, OCR stem cells in embodiments of the invention are at least 80% pure, at least 85% pure, at least 90% pure, at least 95% pure, at least 97% pure, at least 98% pure, at least 99% pure, at least 99.5% pure, or at least 99.9% pure Grem1+, and optionally CD105+, OCR stem cells.

In addition, certain embodiments of the invention comprise a composition comprising an acceptable carrier and the isolated Grem1+, and optionally CD105+, stem cells described above in this paragraph and described throughout the specification. Certain embodiments of the invention also include substantially pure isolated Grem1+ OCR stem cells from bone and bone marrow, which express the cell marker Grem1+ and optionally CD105+. In other embodiments, methods are provided for treating osteoarthritis and bone fracture by administering a therapeutically effective amount of the composition. The composition may be administered to tissue surround the fracture, C. Therapeutic Methods The OCR stem cells identified herein can be used for treating disease, degeneration or injury of bone and/or cartilage tissue. Examples of conditions that may be treated include, but are not limited to, arthritis; osteoarthritis; osteoporosis; osteochondrosis; osteochondritis; osteogenesis imperfecta; osteomyelitis; osteophytes; achondroplasia; costochondritis; chondroma; chondrosarcoma; herniated disk; Klippel-Feil syndrome; osteitis deformans; osteitis fibrosa cystica, a congenital defect that results in absence of a tissue; accidental tissue defect or damage; fracture; wound; joint trauma; an autoimmune disorder; diabetes; Charcot foot; tissue resection; periodontal disease; implant extraction; or tumor resection. The OCR stem cells are particularly suitable for treating conditions such as osteoarthritis, osteoporosis and fracture.

In certain embodiments, Grem1 OCR stem cells are harvested from a donor animal, expanded in vitro, and transplanted, directly and serially, into a site of need in a recipient animal. A site of need includes, but is not limited to, the space of a joint, cartilage tissue of the joint, the articular tissue of the bones forming the joint, locations on a bone outside of a joint; a site of fracture or defect and tissue surrounding a fracture or defect.

The discovery of analogous is likely to be important in intestinal replacement and repair and may inform mesenchymal hierarchy in other complicated connective tissues including the tumor microenvironment. iRSCs will be used in settings requiring the support of epithelium, such as in generation of new tissue for intestinal failure (such as short gut, inflammatory ulceration, peptic ulceration, fistulae), it could also be used for screening therapeutic targets in cancer, when the epithelial-mesenchymal partnership is more predictive of drug sensitivity then epithelial-specific tissue alone and finally could be used to help mature epithelium to better model intestinal microbiome interactions.

Accordingly, in a further embodiment, disclosed is a method that involves obtaining a population of isolated intestinal reticular stem cells (iRSCs); and administering the population of iRSCs into an intestine of a subject in need thereof. Upon administration, the population of iRSCs is able to generate periepithelial mesenchymal sheath in the intestine of the recipient. Typically, the isolated iRSCs are isolated based on expression of Grem1. The isolated Grem1 expressing intestinal cells may be subjected to cell culture conditions to generate a clone and further a gut organoid suitable for implantation.

A further method embodiment involves (a) obtaining an intestinal cell sample from a subject, wherein the intestinal cell sample comprises intestinal reticular stem cells (iRSCs); and (b) isolating from the cell sample a population of cells that express Gremlin 1 (Grem1), to produce a sample of isolated iRSCs.

Treatment of Diseases Associated with Bone or Tissue Damage.

In certain embodiments, OCR stem cells are administered to treat diseases of the bone or cartilage such as osteoarthritis. As an example, a subject in need may have damage to a tissue, such as bone tissue, and the method provides an increase in biological function of the tissue by at least 5%, 10%, 25%, 50%, 75%, 90%, 100%, or 200%, or even by as much as 300%, 400%, or 500%. As yet another example, the subject in need may have a disease, disorder, or condition, and the method provides an administration of OCR stem cells or compositions comprising them, sufficient to ameliorate or stabilize the disease, disorder, or condition. For example, the subject may have a disease, disorder, or condition that results in the loss, atrophy, dysfunction, or death of bone and/or cartilage cells. Exemplary treated conditions include arthritis; osteoarthritis; osteoporosis; osteochondrosis; osteochondritis; osteogenesis imperfecta; osteomyelitis; osteophytes (i.e., bone spurs); achondroplasia; costochondritis; chondroma; chondrosarcoma; herniated disk; Klippel-Feil syndrome; osteitis deformans; osteitis fibrosa cystica, a congenital defect that results in the absence of a tissue; accidental tissue defect or damage such as fracture, wound, or joint trauma; an autoimmune disorder; diabetes (e.g., Charcot foot); cancer; a disease, disorder, or condition that requires the removal of a tissue (e.g., tumor resection); periodontal disease; and implant extraction. In a further example, the subject in need may have an increased risk of developing a disease, disorder, or condition that is delayed or prevented by the method.

The methods, compositions, and devices of the application can include concurrent or sequential treatment with one or more of enzymes, ions, growth factors, and biologic agents, such as thrombin and calcium, or combinations thereof. The methods, compositions, and devices of the application can include concurrent or sequential treatment with non-biologic or biologic drugs.

Bone Fracture

In certain embodiments, OCR stem cells are administered to treat bone fracture. OCR stem cells stimulate bone regeneration following injury and contribute to improved wound healing in bone. OCR stem cells provide improvements in the speed of bone fracture repair enabling a reduction in the recovery time from injury. Administration of OCRs is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

In certain embodiments, fractures include closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces. Other fracture types include, compression fracture, compacted fracture, spiral fracture, complete and incomplete fractures, transverse, linear and oblique fractures and comminuted fractures. In most subjects bone healing (fracture union) occurs naturally and is initiated following injury. Bleeding normally leads to clotting and attraction of white blood cells and fibroblasts, followed by production of collagen fibeRs. This is followed by bone matrix (calcium hydroxyapatite) deposition (mineralization) transforming the collagen matrix into bone. Immature re-generated bone is typically weaker than mature bone and over time the immature bone undergoes a process of remodeling to produce mature "lamellar" bone. The complete bone healing process takes considerable time, typically many months.

Bones in which fractures occur and which may benefit from treatment using OCRs include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella). Bone fracture also includes pathological porosity, such as that exhibited by subjects with osteoporosis.

D. Compositions and Kits

For the administration in the prevention and/or treatment of a bone or cartilage disorder, such as joint disorders (e.g., osteoarthritis), ORC stem cells of the invention can be formulated in a suitable composition, comprising ORC stem cells of the invention, in a therapeutically or prophylactically effective amount, together with a suitable pharmaceutically acceptable vehicle. The composition of the invention can be formulated according to the chosen form of administration. For example, a composition is prepared in a liquid dosage form, e.g., as a suspension, to be injected into the subject in need of treatment. The composition of the invention can contain a prophylactically or therapeutically effective amount of the cells of the invention, preferably in a substantially purified form, together with the suitable vehicle in the appropriate amount in order to provide the form for proper administration to the subject. Suitable carriers or components typically used alone, or in combination, are known in the art and include, but are not limited to, water, saline, dextrose, and glycerol.

The compositions of the invention, if desired, can also contain, when necessary, additives to enhance, control, or otherwise direct the intended therapeutic effect of the cells comprising said pharmaceutical composition, and/or auxiliary substances or pharmaceutically acceptable substances, such as minor amounts of pH buffering agents, tensioactives, co-solvents, preservatives, etc. For example, the pharmaceutical composition preferably comprises constituents which protect, culture, and maintain the stem cells for a desired treatment period of 5 to 14 days or more thereby extending the release of therapeutic extracellular factors from the encapsulated cells. The pharmaceutical composition can also contain constituents to maintain the stem cells in undifferentiated form. The stability of the cells in the pharmaceutical composition of the invention can be improved by means of adding additional substances, such as, for example, amino acids such as aspartic acid, glutamic acid, etc. Pharmaceutically acceptable substances that can be used in the pharmaceutical composition of the invention are known, in general, by the skilled person in the art and are normally used in the manufacture of cellular compositions.

The compositions may also include auxiliary substances such as growth factors, cytokines, hormones, and various nutrients. Illustrative growth factors may include transforming growth factor-beta (TGF-β), fibroblast growth factors (FGFs), insulin like growth factors (IGFs), bone morphogenic proteins (BMPs); illustrative cytokines may include cytokine-like 1 (Cytl1); illustrative hormones may include human growth hormone (HGH); and testosterone; and illustrative nutrients may include ascorbic acid, pyruvate, hyaluronic acid and amino acids.

The compositions may also include additional therapeutic agents routinely used in the art for alleviation of pain and inflammation and include, but are not limited to, narcotics, corticosteroids, anti-inflammatories including ibuprofen, naproxen, diclofenac, anti-biotics, analgesics, and natural remedies, In one example of a therapeutic composition, OCR stem cells are produced by any of the methods described herein. OCR stem cells are then prepared for application to subjects in need of the cells. OCR stem cells can also be prepared in pharmaceutical dosages (e.g., in a pharmaceutically acceptable solution) and stored in appropriate containers. The OCR stem cells can be stored in an appropriate manner (e.g., frozen) until needed. Additionally, the pharmaceutical dosages can be placed in pre-prepared syringes, catheters or other medical devices appropriate for delivery to an affected joint. One of skill in the art will recognize that dosage amount, needle length and other such parameters can be adjusted for any individual preparation.

A pharmaceutical composition containing OCR stem cells of the present invention may be stored until use by means of conventional methods known by the skilled person in the art. For short term storage (less than 6 hours) the pharmaceutical composition containing said cells may be stored at or below room temperature in a sealed container with or without supplementation with a nutrient solution. Medium term storage (less than 48 hours) is preferably performed at 2-8° C., the pharmaceutical composition comprising an iso-osmotic, buffered solution in a container composed of or coated with a material that prevents cell adhesion. Longer term storage is preferably performed by appropriate cryopreservation and storage under conditions that promote retention of cellular function.

OCR stem cells produced, stored, or banked may be administered to non-autologous recipients in either prepared dosages or pre-dosage containers and can be shipped to medical facilities through any approved delivery system (governmentally approved and/or commercial). OCR stem cells can be delivered directly from the manufacturer or via an intermediary.

E. Administration of Therapeutic Compositions

The administration of the pharmaceutical composition of the invention to the subject in need thereof can be carried out by conventional means. In a particular embodiment, said pharmaceutical composition can be administered to the subject in need by administration using devices such as syringes, catheters, trocars, cannulae, etc. for direct injection into a joint to help repair cartilage, injection into subchondral defects, bone fractures, etc. engineering various cell-based scaffolds for implantation for bone or cartilage repair, or bone paste materials. In any case, the pharmaceutical composition of the invention will be administrated using the appropriate equipment, apparatus, and devices which are known by the skilled person in art in a therapeutically or prophylactically effective amount, together with a suitable pharmaceutically acceptable vehicle.

OCR stem cells disclosed herein can be applied by several routes including direct injection into the affected anatomical site. A pharmaceutical composition containing the cells may be injected in a single bolus, through a slow infusion, or through a staggered series of applications separated by several hours, several days or weeks. In any case, the pharmaceutical composition of the invention will be administrated to the target tissue using the appropriate equipment, apparatus, and devices which are known by the skilled person in art in a therapeutically or prophylactically effective amount.

One of skill in the art will recognize that cell numbers (e.g., dosage amount) will vary depending upon multiple factors including, but not limited to site of administration, extent of disease, and method of administration. For example, an administration directly into the joint of a subject suffering from OA will typically contain a smaller number of cells than an administration of the cells into the bloodstream. The dose of cells disclosed herein can be repeated, depending on the patient's condition and reaction, at time intervals of days, weeks or months as determined necessary by a treating physician or other healthcare professional.

Compositions according to the present invention may be formulated for administration in fluid or liquid form for injection, or as part of a gel suitable for application to bone or other tissue surrounding the fracture. In certain embodiments where OCR stem cells are being used for treatment of bone fracture, administration is preferably in a therapeutically effective amount, this being sufficient to improve healing of the bone fracture compared to a corresponding untreated fracture or to a fracture treated with MSCs obtained from culture in control conditions. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of OCR stem cells doses may be administered in accordance with the guidance of the prescribing medical practitioner. Purely by way of example, OCR stem cells may be delivered in dosages of about 10-10,000,000 cells. Examples of the techniques and protocols mentioned above can be found in Remington's Pharmaceutical Sciences, 20th Edition, 2000, pub. Lippincott, Williams & Wilkins.

OCR stem cells may be used to treat bone fracture alongside other treatments, such as administration of pain relieving or anti-inflammatory medicaments, immobilization and setting of the bone, e.g. immobilizing the injured limb in a plaster cast, surgical intervention, e.g. to re-set a bone or move a bone to correct displacement, angulation or dislocation. If surgery is required OCR stem cells may be administered directly to (e.g. applied to) the fracture during the surgical procedure.

Therapeutic compositions and medicaments of the invention may take the form of a biomaterial that is coated and/or impregnated with OCR stem cell. An implant may be formed from the biomaterial and be surgically implanted to assist in bone growth, regeneration, restructuring and/or re-modeling.

In other embodiments, OCR stem cells may be applied to implants to accelerate new bone formation at a desired location. The biomaterial may be coated or impregnated with OCR stem cells. Coating or impregnating may comprise contacting the OCR stem cells with the biomaterial such that they are allowed to be adsorbed and/or absorbed onto and/or into the biomaterial. Coating may comprise adsorbing the OCR stem cells onto the surface of the biomaterial. Coating or impregnation of the biomaterial may involve seeding OCR stem cells onto or into the biomaterial. The biomaterial should allow the coated or impregnated OCR stem cells to be released from the biomaterial when administered to or implanted in the subject. Biomaterial release kinetics may be altered by altering the structure, e.g. porosity, of the biomaterial. Biomaterials coated or impregnated with ORC stem cells may improve the quality of life of a patient.

In other embodiments, the biomaterial provides a scaffold or matrix support. The biomaterial may be suitable for implantation in tissue, or may be suitable for administration (e.g. as microcapsules in solution). The implant should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

The matrix configuration can be dependent on the bone tissue that is to be produced. Preferably the matrix is a pliable, biocompatible, porous template that allows for target tissue growth. The matrix can be fabricated into structural supports, where the geometry of the structure is tailored to the application. The porosity of the matrix is a design parameter that influences cell introduction or cell infiltration. The matrix can be designed to incorporate extracellular matrix proteins that influence cell adhesion and migration in the matrix. Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking Alternatively biomaterials may be relatively rigid structures, e.g. formed from solid materials such as plastics or biologically inert metals such as titanium. The biomaterial may have a porous matrix structure which may be provided by a cross-linked polymer. The matrix is preferably permeable to nutrients and growth factors required for bone growth.

Matrix structures may be formed by crosslinking fibers, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, poly-acrylonitrile, polymethylmethacrylate, co-polymers thereof A matrix with a high porosity and an adequate pore size can provide for increased cell introduction and diffusion throughout the whole structure of both cells and nutrients. Matrix biodegradability can provide for absorption of the matrix by the surrounding tissues (e.g., after differentiation and growth of bone tissues from progenitor cells) and can eliminate the necessity of a surgical removal. The rate at which degradation occurs should coincide as much as possible with the rate of tissue formation. Thus, while cells are fabricating their own natural structure around themselves, the matrix can provide structural integrity and eventually break down leaving the neotissue, newly formed tissue which can assume the mechanical load. Inj ectability is also preferred in some clinical applications. Suitable matrix materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

The biomaterial can be supplemented with additional cells. For example, one can "seed" the biomaterial with feeder cells, which may be useful for supporting growth and maintenance of the OCRs. The subject to be treated may be any animal or human. The subject is preferably mammalian. In some embodiments the subject is a human. In other embodiments the subject is an animal, more preferably a non-human mammal. In certain embodiments, non-human mammals include rabbits, guinea pigs, rats, mice or other rodents (including any animal in the order Rodentia), cats, dogs, pigs, sheep, goats, cattle (including cows or any animal in the order Bos), horse (including any animal in the order Equidae), donkey, and non-human primates. The subject may be male or female. The subject may be a patient.

The present teachings include methods for optimizing the density of OCR stem cells (and their lineage derivatives) so as to maximize the regenerative outcome of a bone tissue. Cell densities in a matrix can be monitored over time and at end-points. Tissue properties can be determined, for example, using standard techniques known to skilled artisans, such as histology, structural analysis, immunohisto-chemistry, biochemical analysis, and mechanical properties. As will be recognized by one skilled in the art, the cell densities of progenitor cells can vary according to, for example, progenitor type, tissue or organ type, matrix material, matrix volume, infusion method, seeding pattern, culture medium, growth factors, incubation time, incubation conditions, and the like.

F. Kits

Also provided are kits. Such kits can include a therapeutic composition described herein and, in certain embodiments, instructions for administration. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit. Such kits can facilitate performance of the methods described herein. When supplied as a kit, the different components of the composition can be packaged in separate containers and admixed immediately before use. Components include, but are not limited to OCR stem cells, culture media, and matrix or scaffold materials, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include OCR stem cells in a container with or without other components such as water, media, growth factors etc. Containers may include test tubes, vials, flasks, bottles, syringes, bags or pouch, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Summary of Experimental Results

The following is a summary of results of experiments described in the Examples of this application:

Grem1 expression identifies a new bone, cartilage and stromal stem cell.

Grem1 cells are endogenous OCR stem cells.

OCR stem cells are distinct from Nes-GFP+ MSCs.

Grem1 expression also defines intestinal connective tissue (reticular) stem cells (iRSCs).

Grem1+ OCR stem cells contribute to fracture repair.

A new model of skeletogenesis and intestinal mesenchymal homeostasis is established.

Example 1

Materials and Methods

Mice

The following lines were used: Nes-GFP (Mignone et al., 2004), Nes-CreER$^{T2}$ (Dranovsky et al., 2011), Grem1-LacZ (Khokha et al., 2003), Acta2-RFP (Magness et al., 2004), R26-LSL-ZsGreen (Madisen et al., 2010), R26-LSL-TdTomato (Madisen et al., 2010), R26-LSL-mT/mG (Muzumdar et al., 2007), 2.3ColGFP (Kalajzic et al., 2002), R26-LSL-Confetti (Snippert et al., 2010), and R26-LSL-DTA (Voehringer et al., 2008) (Table 1B). The R26-LSL- mT/mG was used in the intestine to better appreciate intestinal architecture, but for the bone marrow, either the R26-LSL-ZsGreen or the R26-LSL- TdTomato was used to enable the addition of a second reporter, such as Nes-GFP, 2.3colGFP or Acta2-RFP. We generated the Grem1-CreERT transgenic by BAC recombineering (clone RP24-317C19), as previously described (Sharan et al., 2009). The recombineering primers amplified the CreER$^T$-pA-fNf cassette with 60 bp homology arms upstream and downstream of the Grem1 translational start site in exon 2 (Table 1). We generated three founder lines. Line 3 displayed the greatest recombination following adult tamoxifen induction, and it was backcrossed six generations to C57BL/6J. All experiments were performed according to the guidelines of the Institute of Comparative Medicine at Columbia University.

Marrow Stromal Cell Isolation

Long bones of the arms and legs were harvested and gently disrupted using a mortar and pestle, in PBS with 2% FBS and 1 mM EDTA. The bone and all of the liberated bone marrow were collected and digested in 0.25% collagenase type I (Worthington, Lakewood, N.J., USA, LS004196) in PBS with 20% FBS, for cell culture or flow cytometry.

Clonal In Vitro Bone Marrow MSC Culture, Clonogenicity Assays, and Differentiation Marrow stromal cells were plated at clonal density and cultured for 14 days in aMEM+10% defined MSC FBS+1% penicillin/streptomycin. The total number of colonies, defined as R50 cells, was stained with Giemsa. The number of clones were reported as (CFU-Fs)/1,000 cells plated. For differentiation, single recombined clones were isolated using cloning cylinders and then expanded and split for differentiation using Invitrogen StemPro differentiation products into adipocytes, chondrocytes, and osteoblasts. All in vitro differentiation reported in this study is clonal.

Fracture Studies

Adult Grem1-creER$^T$;R26-LSL-TdTomato;2.3ColGFP mice were induced with tamoxifen with a 1 week washout period before fracture. Unilateral femoral osteotomy was internally fixed by an angiocatheter. Femurs were harvested at 7 days. For the fracture transplantation, a single Grem1-derived clone (after adult in vivo induction) was expanded in vitro and then 500 3 $10^6$ cells were mixed with a HyStem-C(TM) Hydrogel Kit (Glycosan) and injected around the fracture sites of the recipient wild-type mice. The fractured bones were harvested at 7 days. Some of the fracture callus was recultured to recover the donor Grem1$^+$ cells. The fractures were imaged by X-ray and a Kodak In Vivo Multispectral Imaging System FX (carestream Health) specific for TdTomato fluorescence.

Tissue-Engineered Small Intestines

Organoid units were harvested from 3-week-old, P1 tamoxifen-induced Grem1-creERT;R26-LSL-TdTomato donor mice and transplanted into 8 wild-type adult C57BL/6 mice. The procedure was otherwise performed as previously described (Levin et al., 2013) with the TESIs harvested at 4 weeks post-implantation for analysis.

Tamoxifen Induction of Mice

Tamoxifen for adult induction of creERT lines was administered at 6 to 8 weeks of age. Induction schedule for intestine was one 6mg dose of tamoxifen dissolved in 300 µL of corn oil administered by gastric gavage. For the bone marrow 4×6 mg doses of tamoxifen were administered alternate days by gastric gavage. For perinatal induction, the pups were injected subcutaneously with 2 mg of tamoxifen dissolved in corn oil. The embryonic induction was 2 mg of tamoxifen administered by oral gavage to pregnant dams at E13.5.

Flow Cytometry

For all flow cytometry and FACS the cells were blocked and then incubated with primary antibodies from BioLegend and BD Biosciences following standard procedures (Table 2). Flow cytometry and FACS was performed on a BD FACSAria cell sorter.

In Situ Hybridization

Single whole-mount in situ hybridization was performed as previously described (Brent et al., 2003). Briefly, embryos were fixed in 4% PFA, dehydrated into Methanol and bleached. DIG-labeled antisense probes (~300-600 ng/ml) were hybridized at 70° C., detected with α-DIG-AP (1:2000, Roche), and developed using BM Purple (Roche). Grem1 probe was a generous gift from Richard Harland.

Microarray n=3 adult (6-8 weeks) Grem1-creERT;R26-LSL-TdTomato mice were induced and bone marrow sorted by FACS with the non-recombined CD45/CD31/Ter 119 triple negative population compared to the Grem1+ cells. The extracted RNA was amplified using the Nugen single direct kit. Data from the hybridized chips were scanned and analyzed using Bioconductor and R software (Gentleman et al., 2004; Ihaka and Gentleman, 1996). All chips passed recommended QC tests (Bolstad et al., 2005), Normalization was performed using GCRMA (Wu and Irizarry, 2005; Wu et al., 2004) and statistical analysis was performed using Limma (Smyth, 2004). A cutoff of a Benjamini-Hochberg False Discovery Rate (Benjamini and Hochberg, 1995), fdr<0.05, was used found. The array data was deposited in the Gene Expression Omnibus (GSE57729)(Barrett et al., 2005). Pathway Analysis was performed with PathwayGuide (Tarca et al., 2009)

Analysis of Clonal Confetti Labeling in the Bone

We estimated the probability that patches of adjacent identically-colored cells ("clones") where not in fact clonally-derived, but instead due to the merging of multiple independently initiated clones that by chance bore the same confetti color. To do this, we constructed a Monte Carlo simulation of clone labeling in the growing bone. We assumed that the analyzed area of the bone growth plate at P1 could be reasonably described by a square-lattice, consisting of the approximately 400 cells (which subsequently grow to form the approximately 1000 cells that constitute the analyzed area of the growth plate at 6 weeks of age). The transformation efficacy at P1 was measured to be 94/439 cells (approx. 21%), but we note that only 8 clones were observed at 6 weeks implying the fraction of labeled clones that survive to 6 weeks is 8/94 (approx. 9%). To initiate each Monte Carlo simulation we randomly labeled 2% of cells (e.g. the transformation efficiency x survival fraction) as red, blue or yellow with equal probability according to the observed proportions of each confetti-color (green clones were never observed in practice). Clones where observed to grow to an average of 8 cells by 6 weeks (std dev: 6.2 cells), thus we assumed that two clones within a distance of 3 cells (approximately twice the radius of the average clone size) would collide (merge) in the growing bone. For each labeled cell, we then computed any collisions, and recorded the proportion of the resulting "clones" that were composed of two or more independently labeled cells of the same color. All simulations were performed in the R statistical computing environment. The simulations suggest that 9% of patches of adjacent uniformly colored cells actually had a polyclonal origin, thus >90% were monoclonal.

MicroCT Analyses

MicroCT was performed on a Quantum FX Micro-CT (Perkin-Elmer). The 3D microCT images were imported to image analysis software (ImageJ, National Institutes of Health, Bethesda, Md.). A heuristic algorithm was used to eliminate non-bone voxels. Bone volume was estimated by multiplying the total bone voxel counts in the region of interest (e.g. total field or left femur) after segmentation by the volume per voxel.

Histology

Femoral sections were processed in usual fashion and sectioned using either a Tungsten blade and the CryoJane tape transfer system or following decalcification before conventional sectioning. For the Grem1 in situ hybridization on adult small intestine we used an ACD RNAscope® FFPE reagent kit specific for Grem1, using manufacturer's instructions.

Transmission Electron Microscopy

To define the anatomical relationship between the Grem1+ iRSC-derived periepithelial sheath and the epithelium of the small intestine, fragments from the jejunum of a 6-week-old Grem1-creERT;R26-LSL-TdTomato mouse induced at P1 were fixed by 4% PFA and 0.1% glutaraldehyde. Specimens were embedded in 20% gelatin and 70 μm sections were cut by vibratome. The sections were incubated for 30 minutes at room temperature in the blocking solution (10% normal goat serum in phosphate buffered saline (PBS)) and then with polyclonal rabbit antibodies against dsRed diluted (Table 2). Primary antibodies were located with biotinylated secondary antibodies and avidin coupled to horseradish peroxidase (HRP; Vector ABC elite kit) and visualized with 3-3'-diaminobenzine and glucose/glucose oxidase to generate the peroxide substrate. The sections were then dehydrated through a graded ethanol and examined with a JEOL 1200EX electron microscope.

Small Intestinal Lineage Tracing

6mg of tamoxifen was administered by oral gavage once to 6-8 week old mice, which were then sacrificed at increasing time points post tamoxifen including 24 hours, 1 month, 3 months, 6 months, 9 months, 12 months and 24 months. Three to 5 mice were sacrificed at each time point.

Isolation of Small Intestinal CFU-Fs

Intestines from Grem1-creERT; R26-LSL-TdTomato mice were induced at P1, digested with collagenase VIII and dispase adapted from previous protocols (Manieri et al., 2012; Newberry et al., 1999). The cells were cultured in a 10 cm dish containing 10 mLs of DMEM with 10% FBS, 1% antibiotics with 100 μL of 20 mg/mL DNAse I.

Statistics

All analyses were performed using Stata version 12 (StataCorp, College Station, Texas, USA) or Prism 6 (GraphPad software Inc.).

Example 2

Generating a Specific Marker of Skeletal Stem Cells

To select a specific MSC marker in the bone and intestine, we considered human gene-expression arrays from bone marrow, intestine, and peritumoral mesenchyme (Delorme et al., 2009; Kosinski et al., 2007; Sneddon et al., 2006). Gremlin 1 (Grem1), identified from these studies, is a secreted antagonist of bone morphogenetic protein (Bmp)-2, -4, and -7 and a VEGFR2 agonist (Hsu et al., 1998; Mitola et al., 2010). Grem1 is important in normal skeletal and renal development and homeostasis (Canalis et al., 2012; Khokha et al., 2003; Michos et al., 2004). Furthermore, overexpression of Grem1 interrupts normal intestinal function and has been linked to intestinal cancer (Jaeger et al., 2012). Grem1 expression identified the most clonogenic fraction of marrow stromal cultures (Quante et al., 2011). In the present study, it was confirmed that expression of Grem1 was increased in undifferentiated mesenchymal cultures compared to endogenous bone marrow mesenchyme (FIG. 1A-FIG. 1C). To extend these findings in vivo, a tamoxifen-inducible BAC transgenic creERT line specific for Grem1 expression (Grem1-creERT, was generated. (FIG. 1D- FIG. 1F, Table 1). The Grem1-creERT BAC transgenic line was crossed to different reporters (such as R26-LSL-TdTomato and R26-LSL-ZsGreen) and the R26-LSL-diphtheria toxin subunit A (DTA) line to allow lineage tracing and functional ablation of specific mesenchymal cells, respectively (See Tables 1B and 1C for summary of transgenic lines).

Example 3

Grem1+ Cells Are Distinct from, and More Clonogenic than, Nes-GFP+

Figure 5A:
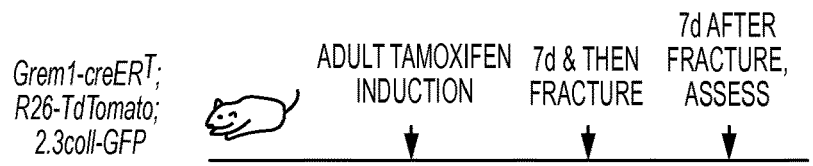
Figure 5B:
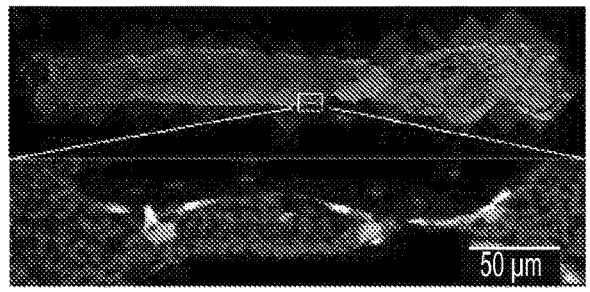

MSCs Tamoxifen induction of adult Grem1-creERT-R26-LSL-TdTomato mice (FIG. 1A) resulted in recombination in and expression of the TdTomato reporter (red fluorescent protein) in a rare and exclusively mesenchymal population of bone marrow cells (0.0025% of all single, live, nucleated cells after collagenase digestion [95% confidence interval (CI) 0.0022-0.0028]). In this experiment and elsewhere in the paper, we defined skeletal mesenchyme as triple negative for CD45$^-$Ter-119$^-$CD31$^-$ in enzymatically digested bone and bone marrow cells. CD45 characterizes most hematopoietic cells with the exception of maturing erythroid cells, which are marked by Ter-119. CD31 was used to exclude endothelial cells (Park et al., 2012) (Table 1D). The CD45-negative, Ter-119-negative, and CD31-negative fraction of bone marrow defines the nonendothelial, nonhematopoietic compartment that contains putative skeletal stem cells. Many Grem1-creER$^{T+}$ cells, identified by a recombined fluorescent reporter gene shortly after tamoxifen administration (hereafter referred to as Grem1$^+$ cells), were immediately adjacent to the growth plate and trabecular bone (FIG. 1B, FIG. 1C, and FIG. 5B).

Figure 9A:
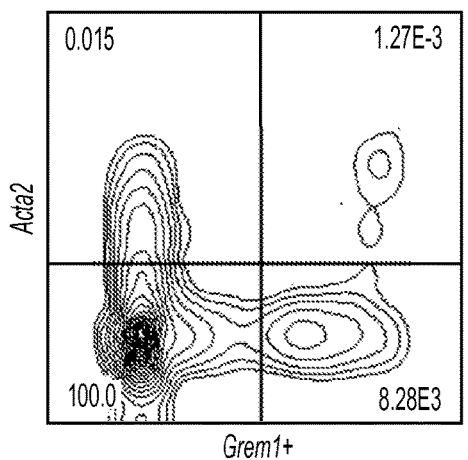
FIG. 9A-9G illustrates (A) Grem1-creER$^T$;R26-LSL-Zs-Green;Acta2-RFP mice (n=3), induced in adulthood revealed that Grem1 cells were usually Acta2-RFP negative. B, When the Grem1 and Acta2 positive populations were sorted and cultured, the Grem1+population was significantly more clonogenic than the CD45-CD31-Ter-119-Acta2-RFP positive cells, p=0.002. In adherent culture the Grem1+ (green) but Acta2 negative cells ultimately differentiate into Acta2 expressing cells (yellow arrows), C, and after sorting these cells and repeating the CFU-F assay, self-renewal was diminished within the Acta2 expressing descendants of Grem1$^+$ cells i.e. clonogenicity in first passage of cultured cells was higher in Grem1+ Acta2- than those that had become Grem1+Acta2+, p=0.003, D. Although, Grem1 cells traced Acta2 cells, they never traced Nes-GFP expressing cells in vitro or in vivo. E, Representative flow cytometry of Grem1-creER$^T$;R26-LSL-TdTomato;Nes-GFP mice induced in adulthood and then followed for 10 months. Despite Grem1 OCR stem cells having generated multiple mesenchymal lineages by this time point, none of the Grem1-recombined cells had differentiated into Nes-GFP cells. Suggesting they are distinct lineages. F & G additional clonal differentiation experiments. In F confirming osteoblast differentiation with alkaline phosphatase detection, and in G, confirming mineralized bone with Alizarin red, and chondrogenesis with Alcian blue.
Figure 9B:
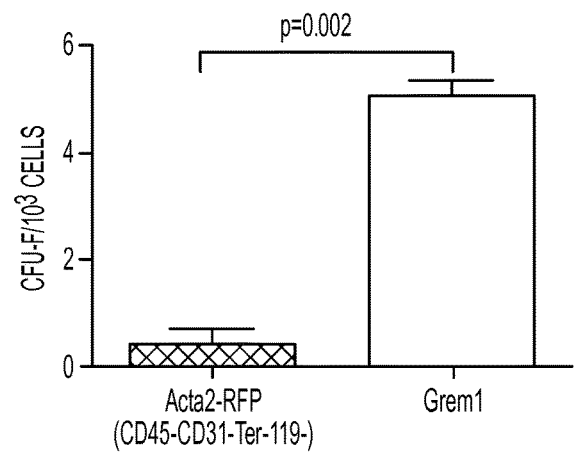
Figure 9C:
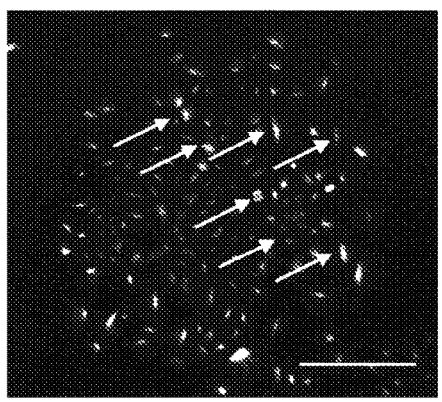
Figure 9D:
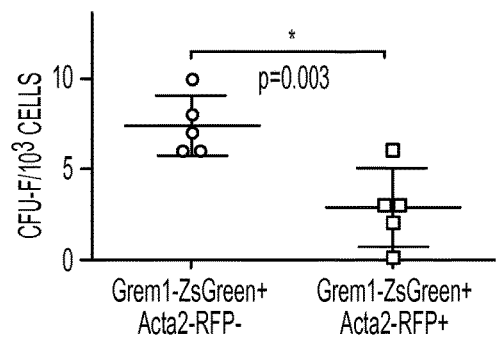
Figure 9E:
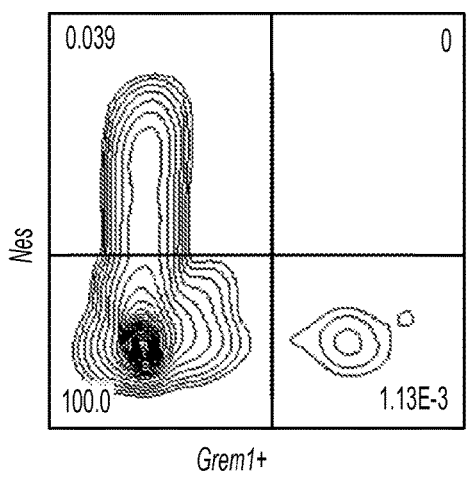

To determine the overlap between Grem1$^+$ and other reported CFU-F populations, Grem1-creERT were crossed to Nes-GFP; R26-LSL-TdTomato (Grem1$^+$ cells and their progeny were red, and Nes-GFP-expressing cells were green) and to Acta2- RFP;R26-LSL-ZsGreen (Grem1$^+$ cells and their progeny were green, and Acta2-RFP-expressing cells were red) (Grcevic et al., 2012; Méndez-Ferrer et al., 2010). Adult Grem1$^+$ cells did not express Nes-GFP (FIG. 1B and FIG. 1D), and only a minority of Grem1$^+$ cells expressed Acta2-RFP (mean 5.9% of Grem1+ were Acta2+; FIG. 9A). The Grem1+ population was more clonogenic than Nes-GFP or Acta2-RFP cells, even after depletion of contaminating nonmesenchymal lineages (FIG. 1D-FIG. 1G and FIG. 9B). Grem1+ CFU-Fs did not initially express Acta2-RFP, but during culture, the Grem1+ progeny differentiated into Acta2-RFP-expressing myofibroblasts (these cells were yellow, expressing both ZsGreen and Acta2-RFP; FIG. 9C). Importantly, the proportion of CFU-Fs was diminished within the Grem1+ descendants expressing Acta2-RFP, suggesting that Acta2 expression marks a more differentiated cell less capable of clonogenic growth (FIG. 9D). Grem1+ cells, however, never gave rise to Nes-GFP-expressing cells, either in adherent culture or in vivo (10 months tracing after adult tamoxifen induction of Grem1-creER$^T$;R26-LSL-TdTomato;Nes-GFP mice; FIG. 9E).

Figure 1H:
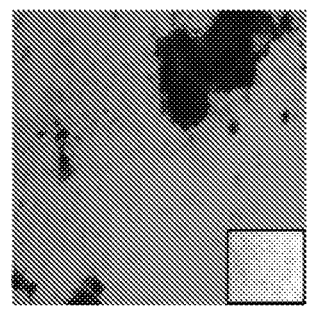
Figure 1I:
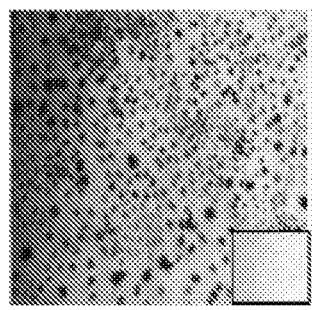
Figure 1J:
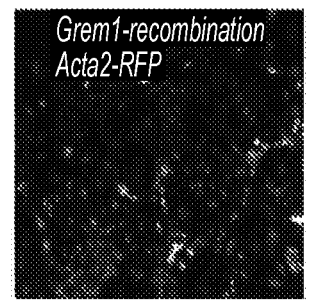
Figure 1K:
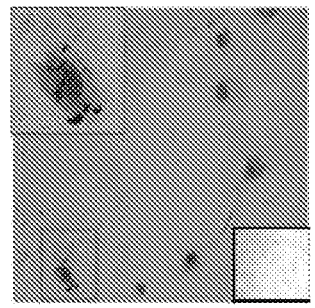
Figure 9F:
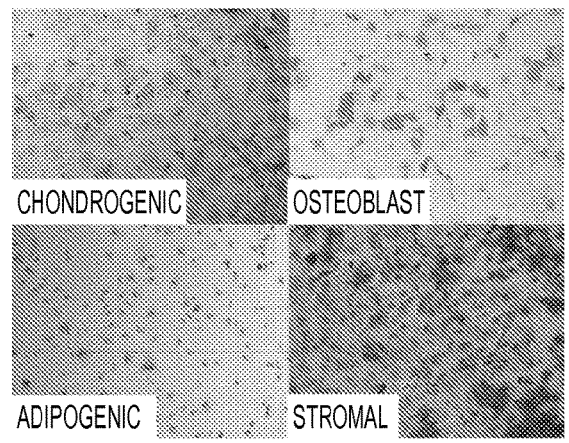
Figure 9G:
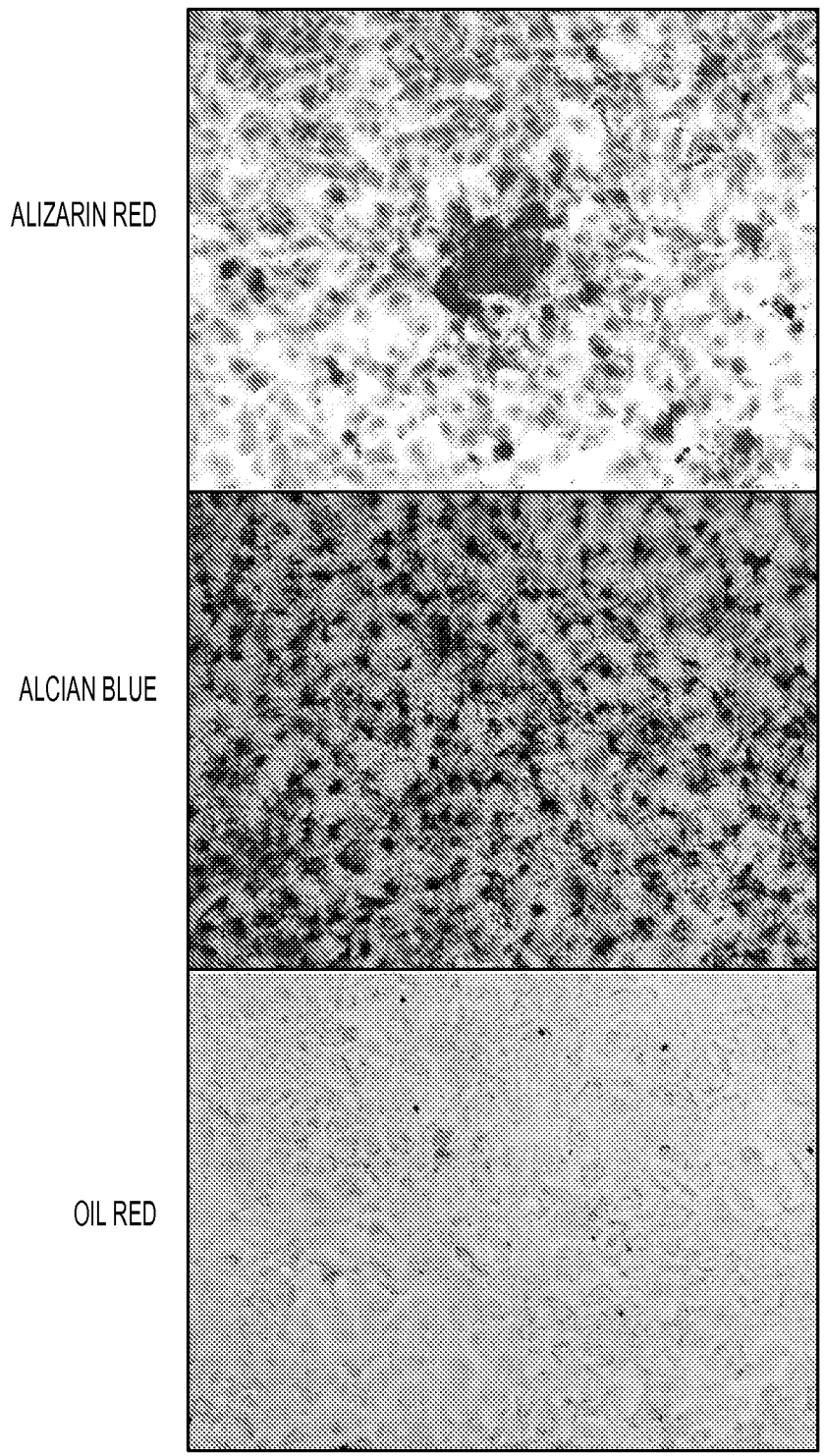

For the clonal differentiation experiments (FIG. 1), adult Grem1-creER$^T$;R26-LSL-ZsGreen;Acta2-RFP and Grem1-creER$^T$;R26-LSL-TdTomato mice were administered tamoxifen by oral gavage at 6-8 weeks of age. Bones were processed as described (see Experimental Procedures), and the fluorescent Grem1+ cells were sorted by fluorescence-activated cell sorting (FACS) and plated at clonal density <2,500 cells/10 cm dish. Clones (i.e., isolated clusters of >50 cells at 10-14 days) were harvested using a cloning cylinder and expanded into individual wells for differentiation. 19 clones were evaluated after in vitro differentiation. Single clones gave rise to osteoblasts (defined by alizarin red [FIG. 1H] or alkaline phosphatase staining in 84% of clones, [FIG. 9F and FIG. 9G]), chondrocytes (100% of clones confirmed by toluidine blue staining), and myofibroblasts on the basis of coexpression of the Acta2-RFP transgene (100%, FIG. 1H-FIG. 1J). In contrast, the Grem1+ cell-derived clones showed little capacity for adipocytic differentiation (defined by oil red staining, FIG. 1K, 0 of 19 single clones). Polyclonal cultures from sorted Grem1+ cells also failed to differentiate into adipocytes.

A substantial proportion (40%) of Grem1+ cells, in addition to being triple negative for CD45$^-$Ter-119$^-$CD31$^-$, were also positive for CD105, a well-established marker of bone marrow CFU-Fs (Park et al., 2012). In contrast, less than 2% of the Grem1-negative cells were CD45$^-$CD31$^-$Ter-119$^-$CD105$^+$. Grem1+ cells, however, expressed lower levels of CD140a and Sca-1 (FIG. 2A-FIG. 2F). The Grem1+ population was enriched for CD45$^-$CD31$^-$Ter-119$^-$CD105$^+$ cells, a subpopulation previously reported to contain all mouse bone marrow CFU-Fs (Park et al., 2012). It followed that Grem1+ cells were also enriched for CFU-Fs compared to Grem1-negative fractions (FIG. 10A and FIG. 10B). It is worth noting that we used standard adherent cell culture conditions (aMEM with 10% FBS), whereas other studies have used 20% FBS, hypoxic conditions, and a ROCK inhibitor, which enhance the recovery of CFU-Fs (Zhou et al., 2014). Thus, the exact CFU-F efficiencies reported in our study may not be directly comparable to other reports.

Gene-expression microarray of Grem1+ versus Grem1-negative mesenchymal (CD45$^-$CD31$^-$Ter-119$^-$) cells revealed 1,426 differentially expressed genes (false discovery rate [FDR]<0.05). The Grem1+ population had significantly higher expression of many osteoblast (Sp7), chondrocyte (Acan), pericytic (Cpsg4, Fap), and putative stem cell genes (Klf4), all of which were confirmed by qPCR (FIG. 2G-FIG. 2M, and FIG. 10C and FIG. 10E). Grem1+ cells did not differentially express Nes (FIG. 2H) or other genes typical of the perisinusoidal mesenchymal niche .

Figure 10F:
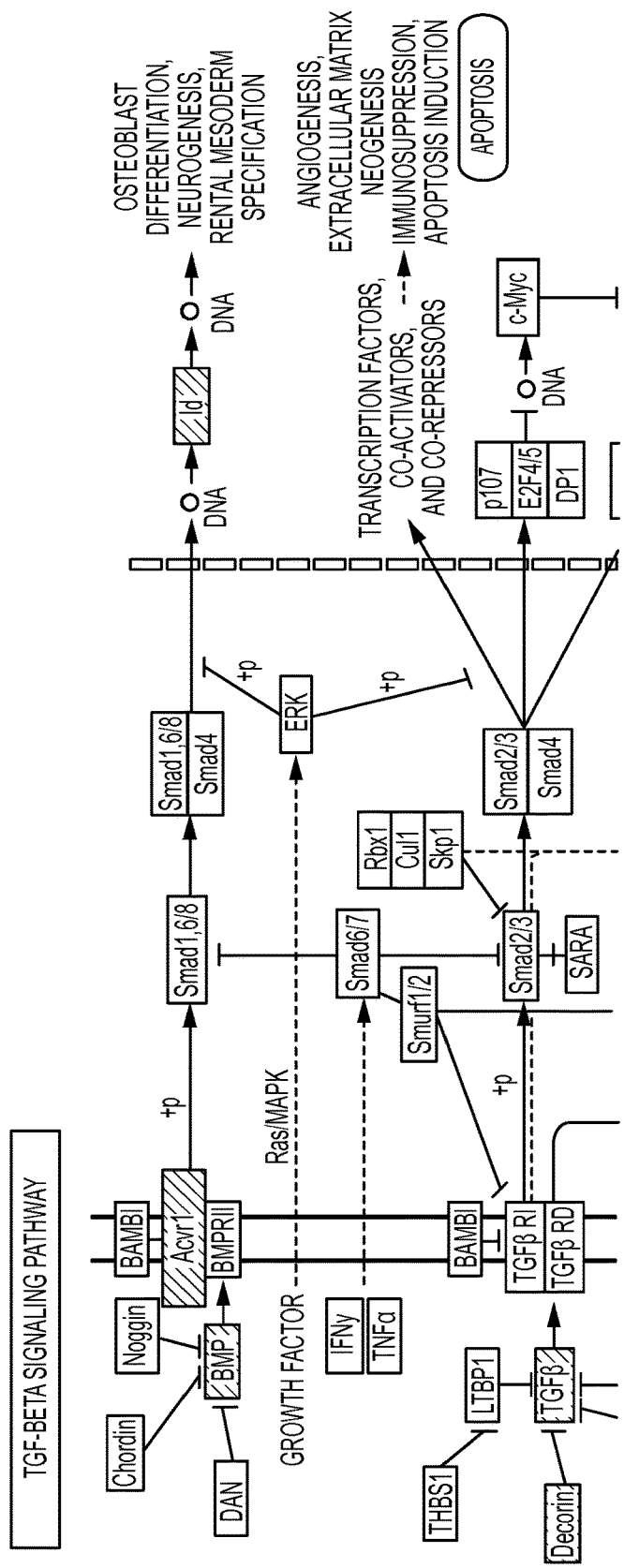
Figure 10G:
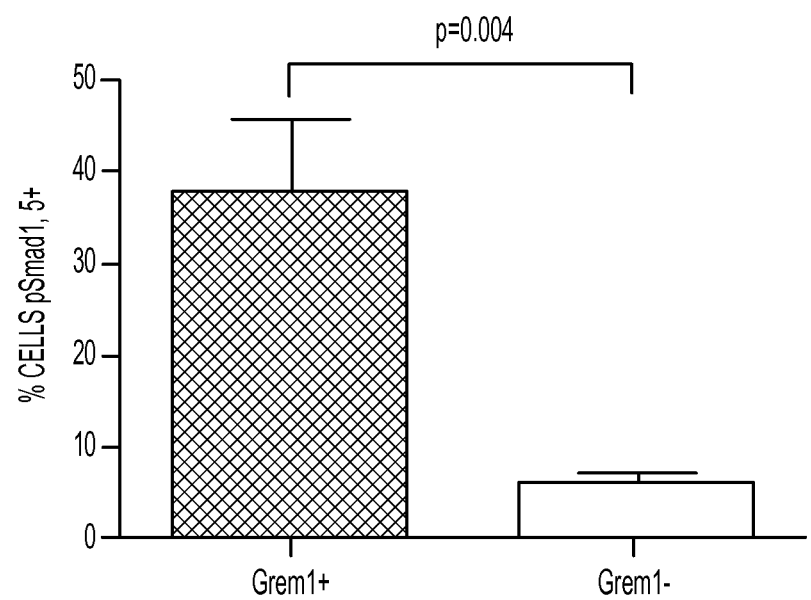
Figure 10H:
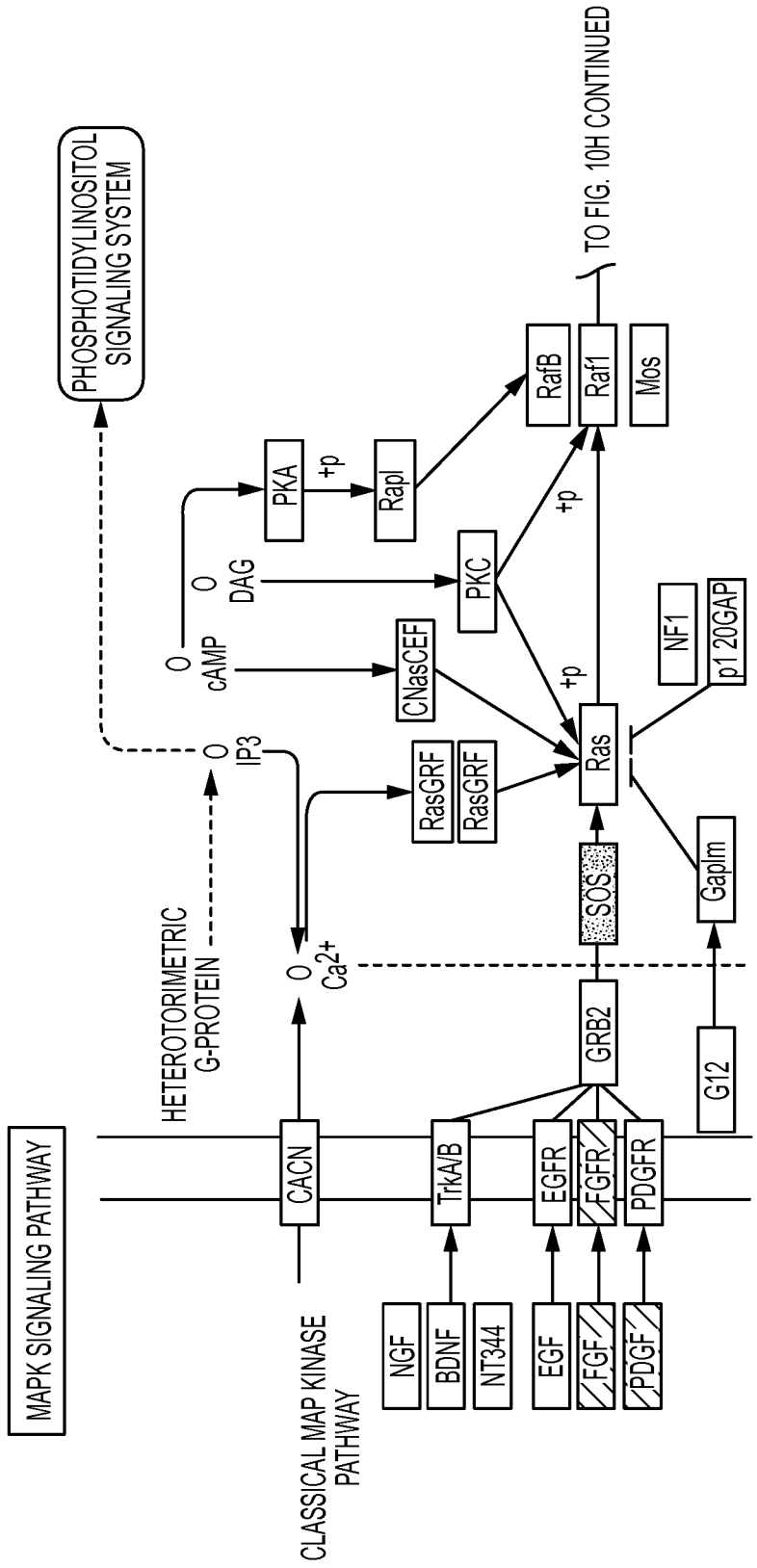
Figure 10H:
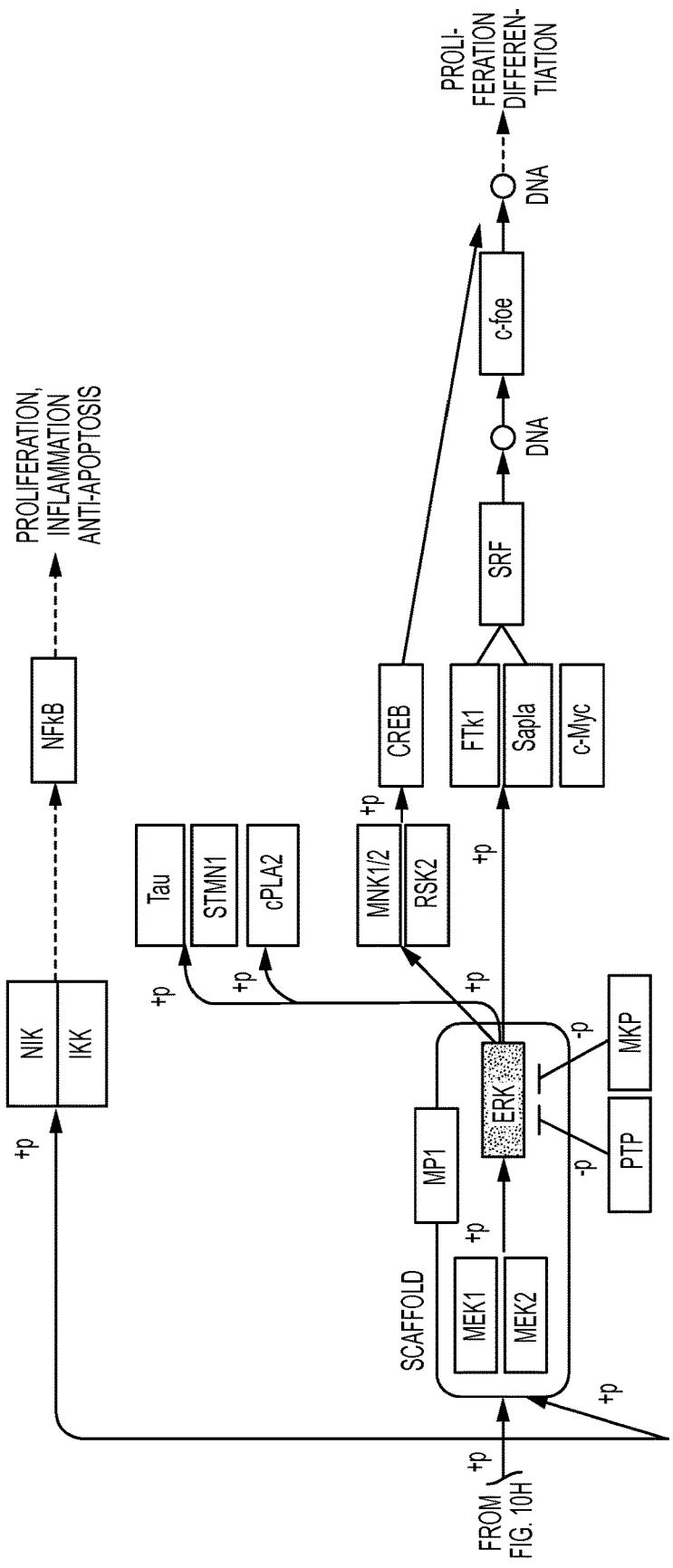
Figure 10I:
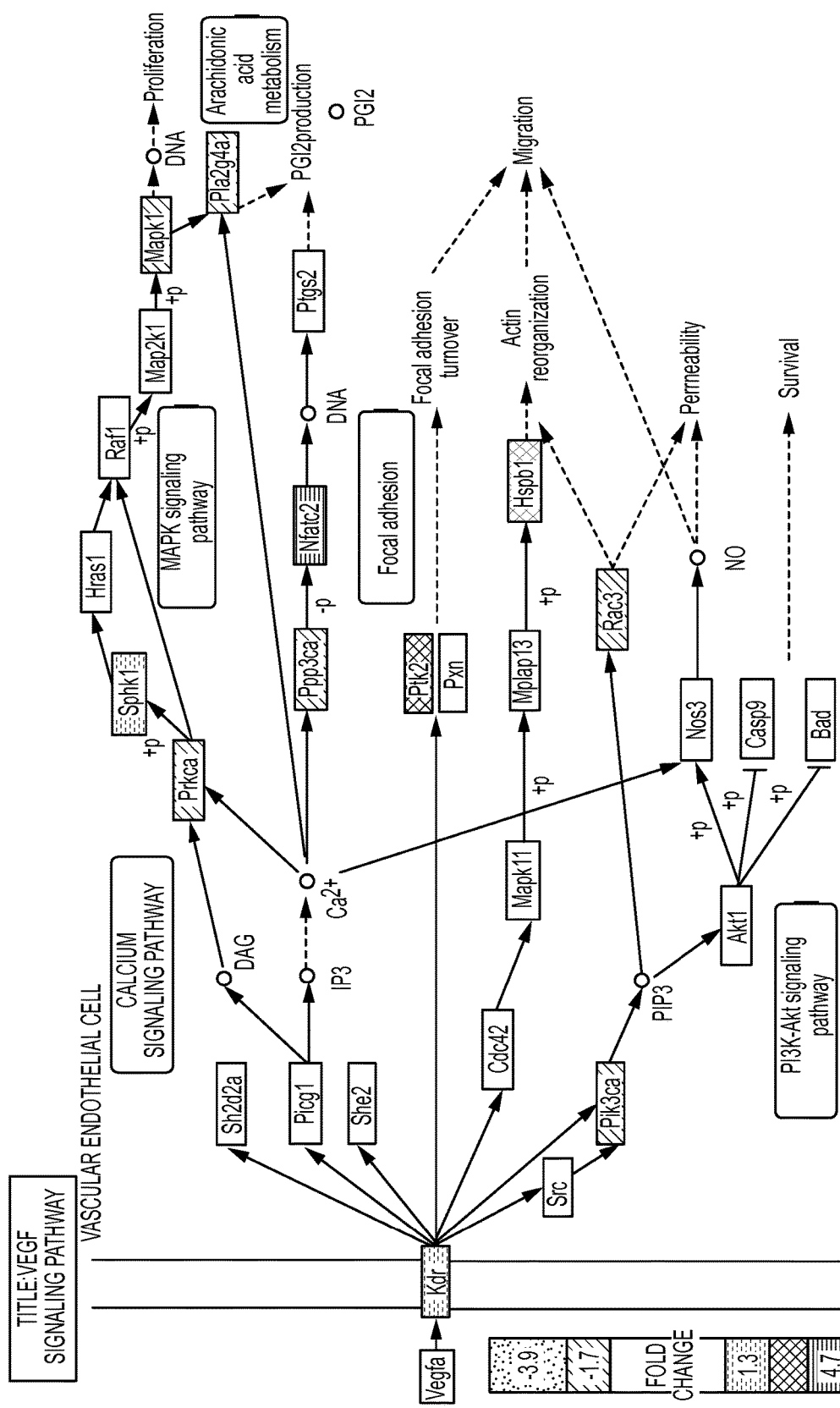

To determine the signaling pathways that were activated in the Grem1+ cells, we investigated candidate pathways previously reported to be relevant in MSC differentiation, such as the BMP, TGF-b, FGF/PDGF, and VEGF pathways (Gerber et al., 1999; Ng et al., 2008). Although all of these pathways were statistically significant (<2.2 3 $10^{16}$ by the c2 test), only the genes in the Bmp-activating pathway were consistently increased. Bmp2, Bmp5, Bmp6, the Bmp receptor Acvr1, and the BMP signaling target gene Id2 were all upregulated in Grem1+ versus Grem1-negative mesenchymal cells (FIG. 10F and Table 1E). To support the role of BMP signaling in the Grem1+ population, we performed qPCR on 23 clones derived from Grem1+ bone marrow cells. Id2 was expressed in 100% of clones, and Bmp2 was expressed in 91% of clones. Furthermore, using flow cytometry, pSmad1,5, a marker of BMP signaling, was detected in 37.5% of Grem1+ versus 5.8% of Grem1-negative freshly sorted cells (Data SIG, p=0.004). In contrast, genes identified in the TGF-b, FGF/PDGF, and VEGF pathways were found to be both activators and repressors and so did not generate a coherent signal constituting pathway activation (FIG. 10F, Data 1H, and FIG. 10I). We also used an unbiased analysis in which all differentially expressed genes in Grem1+ versus Grem1-negative cells (fdr<0.05) were evaluated against the KEGG and Reactome databases. Pathways with a gamma fdr<0.05 are included in Table 1F (KEGG) and Table 1G (Reactome). The top 3 significant KEGG pathways, the ECM-receptor interaction, PI3K-Akt signaling, and focal adhesion pathways, were all activated according to PathwayGuide's statistical criterion. Differentially expressed genes from these pathways are given in Table 1H-Table 1I. Many of the genes upregulated in these pathways are involved in differentiation into bone and cartilage and include the following: chondroadherin, cartilage oligomeric matrix protein, fibroblast growth factors, collagens, integrins, and cyclins. Taken together, BMP signaling along with ECM-receptor inter-action, PI3K-Akt signaling, and focal adhesion pathways were all significantly activated in the Grem1+ cells and are likely to be important either in determining or as a consequence of the Grem1+ cells' osteochondral lineage potential.

Figure 10J:
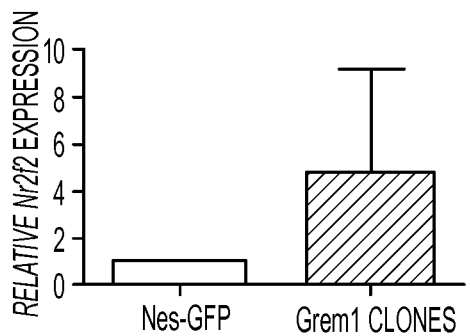
Figure 10K:
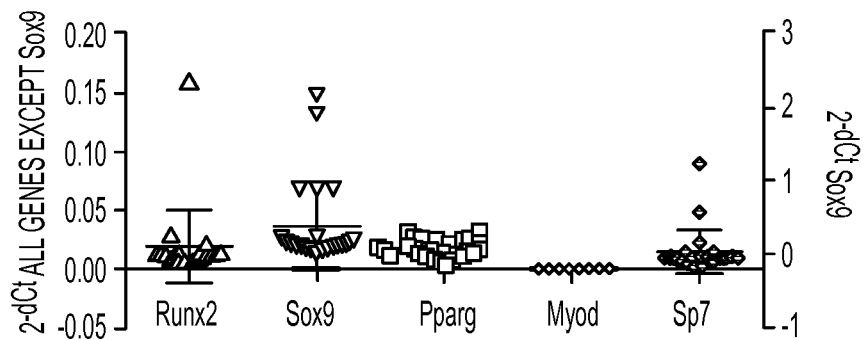
Figure 10L:
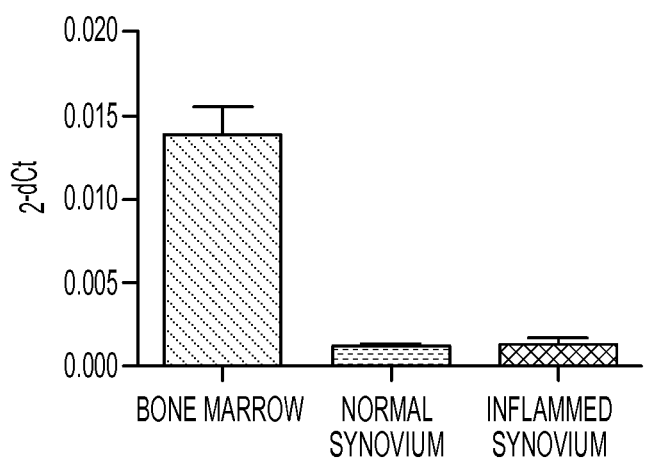

The expression profile of Grem1+ cells was enriched for genes implicated in bone and cartilage, rather than adipocytic, differentiation (FIG. 10J; FIG. 10L-FIG. 10N). Furthermore, Grem1+ cells, and their derivative clones, expressed active inhibitors of adipogenesis (e.g., Nr2f2; FIG. 10K; Xu et al., 2008). The exact molecular explanation for the more restricted mesenchymal repertoire of Grem1+ cells, however, remains to be confirmed.

Further qPCR analysis of 23 Grem1+ cell-derived clones confirmed the mesenchymal homogeneity of Grem1 cells and their derivative clones (FIG. 10L). Interestingly, 100% of the Grem1+ clones expressed both Nes and Grem1, and Grem1 transcripts were also detectable within polyclonal Nes-GFP cultures. Thus, endogenous Grem1 and Nes expression are not as mutually exclusive as their respective transgenes in vivo. Finally, GREM1 is also expressed in human MSCs. We examined three distinct human MSC lines derived from normal bone marrow, normal synovium, or inflamed synovium. All lines expressed GREM1 (FIG. 10M). Grem1 Cells Are Endogenous OCR Stem Cells Grem1-creER$^T$;R26-LSL-ZsGreen;Acta2-RFP mice were induced with perinatal tamoxifen (postnatal day [P] 1, FIG. 3A). In these mice, all Grem1+ cells and their subsequent progeny were labeled by green fluorescence, and any cells expressing Acta2 were marked by red fluorescence. Twenty-four hours after P1 induction, Grem1+ (green) cells were present within the primitive mesenchyme and the primary spongiosa of the femur. In contrast, the Acta2-expressing (red) stromal cells were localized within the bone marrow (FIG. 3B). By P5, Grem1+ cells had differentiated into columns of chondrocytes (FIG. 3C and FIG. 3D, green) as well as spindle-shaped stromal cells immediately inferior to the developing growth plate (FIG. 3C and FIG. 3E).

By using Grem1-creERT;R26-LSL-TdTomato;2.3colGFP mice, one can track Grem1+ cells and their progeny by red fluorescence, and osteoblasts are marked by green fluorescence. The 2.3colGFP mouse is a transgenic line in which GFP expression, driven by a short 2.3 kb promoter element from the rat collagen 1a1 gene, has been used to identify committed osteoblasts (Kalajzic et al., 2002). After 6 weeks, the P1-labeled Grem1+ cells had differentiated into reticular marrow stromal cells (red), chondrocytes (red), and osteoblasts (yellow), all concentrated within the peritrabecular bone area (FIG. 3F-FIG. 3I). Many of the reticular marrow stromal cells anatomically spanned perivascular and endosteal regions and were CD105+ by immunostaining (FIG. 10A). As early as 4 weeks (P28) following P1 induction, Grem1+ cells give rise to approximately 64% of the bone and 50% of the chondrocytes within the metaphysis and epiphysis, albeit with little contribution to diaphyseal bone (FIG. 10B). To prove that the fluorescent cells represented clonal populations, we generated Grem1-creERT;R26-Confetti mice and again induced at P1. Single-color clones of chondrocytes and marrow stromal cells were present by 6 weeks, confirming single-cell multipotentiality (FIG. 3J and FIG. 3K). Our Monte Carlo simulation confirmed that the majority (>90%) of patches of adjacent identically colored cells ("clones") were likely to be monoclonal in origin (see Experimental Procedures).

Approximately 12 months after adult (6-8 weeks, FIG. 3L) tamoxifen induction of Grem1-creERT;R26-LSL-TdTomato mice (and Grem1-creERT;R26-LSL-ZsGreen, mice), we found that Grem1+ cells had differentiated into columns of chondrocytes (FIG. 3M and FIG. 3N), articular cartilage (FIG. 10C), reticular marrow stromal cells (FIG. 3O), periosteal cells (FIG. 3P), diaphyseal osteoblasts (FIG. 10D), and osteocytes (FIG. 3P). No adipocytes, either in the femurs (FIG. 10E) or in the vertebral bodies (FIG. 10F), were derived from adult Grem1 cells, even at 1 year after tamoxifen induction. Fluorescently labeled Grem1+ cells harvested from the bone marrow after 1 year could still self-renew in vitro. The harvested Grem1+ cells in culture formed large colonies, which were clonally expanded (using cloning cylinders) to prove that they retained clonal in vitro multi- potentiality, even 12 months after adult tamoxifen induction (FIG. 10G). Again, in vitro differentiation was skewed to osteoblast and chondrocyte (FIG. 10G-FIG. 10J), with little in vitro adipogenesis (FIG. 10H). These results indicate that expression of Grem1 also identified adult multipotent stem cells.

Figure 11A:
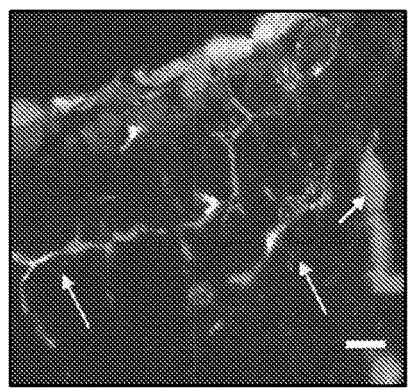
Figure 11B:
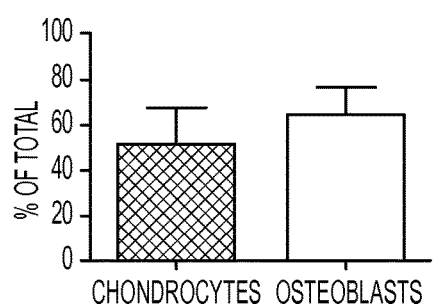
Figure 11C:
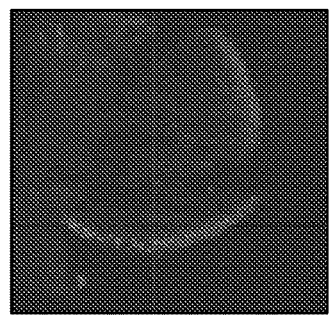

To confirm that Grem1+ cells were functional, postnatal skeletal stem cells, Grem1-creERT;R26-LSL-ZsGreen;R26-LSL-DTA mice and Grem1-creERT;R26-LSL-ZsGreen littermate and related controls were generated. In these mice, Cre-mediated excision of a STOP signal leads to the expression of the Diphtheria toxin (DTA) and thus ablation of Grem1-expressing cells. We administered four daily doses of 2 mg subcutaneous tamoxifen starting at P9 and measured total body and left femoral bone volume by microcomputed tomography (CT) at P23 (Quantum FX MicroCT, Perkin-Elmer; FIG. 11A-FIG. 11C). Grem1 cells were incompletely ablated, although reduced, as assessed by the proportion of ZsGreen-expressing cells in the bone marrow (FIG. 11A). The DTA+ mice were significantly smaller than the controls (FIG. 11B). There was a significant difference in femoral volume between the groups and a trend toward reduced total bone volume in the DTA versus the control mice (FIG. 11C).

Figure 11D:
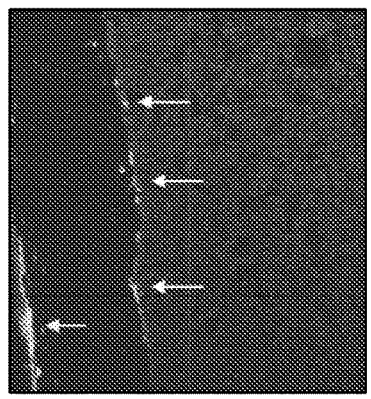

It was noted that the major site of Grem1-driven recombination at P23, after P9 induction, was within the femoral epiphysis (nearly 60% of the epiphyseal bone was labeled). Therefore, we examined anatomically comparable sections in Grem1 DTA versus control mice and measured the fraction of mineralized bone in the femoral epiphysis. Here too, the trabecular bone fraction was significantly reduced in DTA mice versus control mice (FIG. 11D). This suggested a functional role of Grem1+ cells in postnatal skeletogenesis. We acknowledge, however, that ablation of extra-skeletal Grem1+ cells may have indirectly contributed, at least in part, to the impaired skeletogenesis.

Figure 4A:
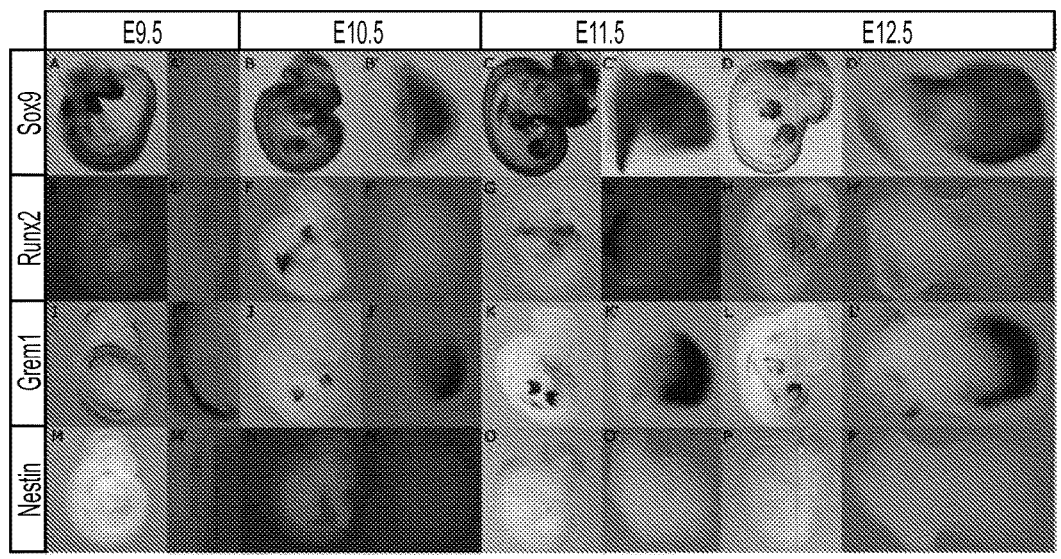
FIG. 4A-4H illustrates that Nes-GFP cells make little contribution to skeletal tissues during early life. (A) Whole-mount in situ hybridization on mouse embryos at E9.5, E10.5, E11.5 and E12.5. These embryos were evaluated for Sox9, Runx2, Grem1, and Nes expression. Nes-creER$^T$; R26-LSL-TdTomato; Nes-GFP mice (n=3) were generated to lineage trace from Nes-GFP-positive cells throughout the bone marrow. These mice were induced at P1 and examined 6-8 weeks after. (B) Protocol. (C) By flow cytometry, approximately 4% of Nes-GFP-positive cells recombined (that is, were both green and red). (D-H) This specific Nes-CreERT transgenic line recombined in all typical Nes-GFP populations, including perivascular cells immediately inferior to the growth plate (D), in periarteriolar cells (E), and in perisinusoidal Nes-GFP-positive cells (red arrows, F-H). The only osteochondral lineage tracing found were isolated osteocytes throughout the diaphyseal bone (H, white arrow).
Figure 11E:
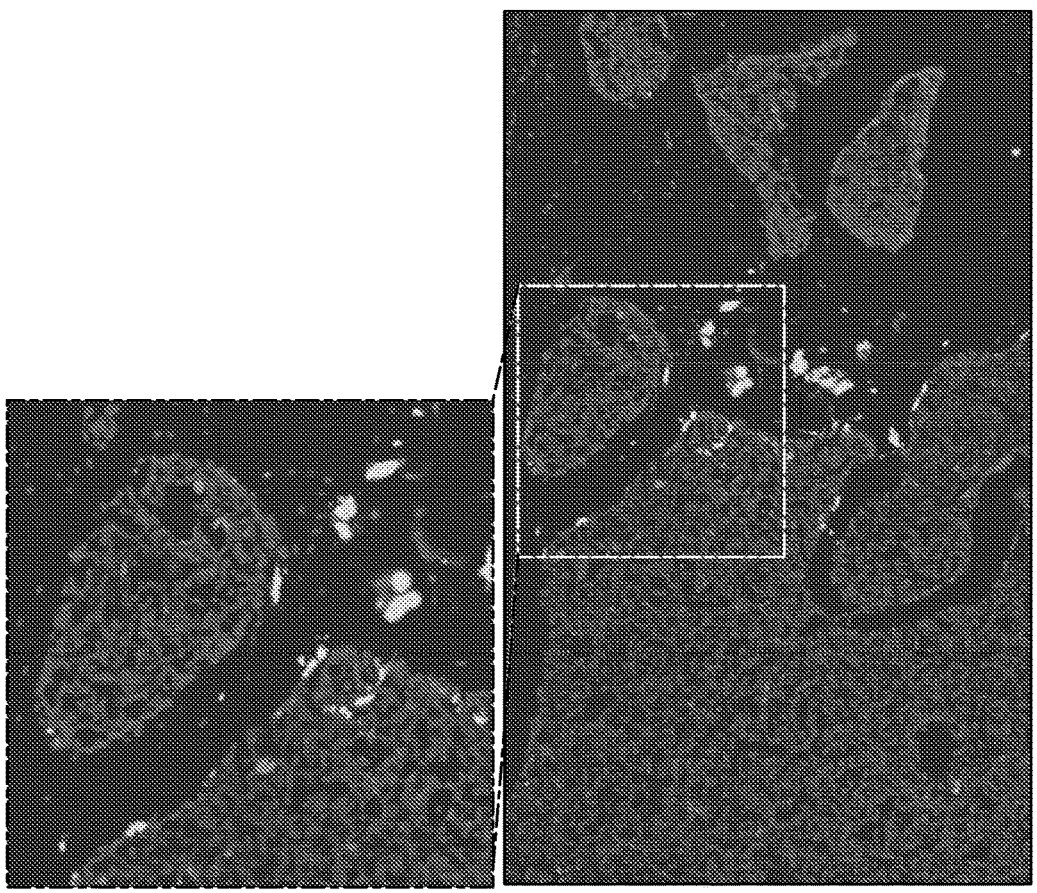
Figure 11F:
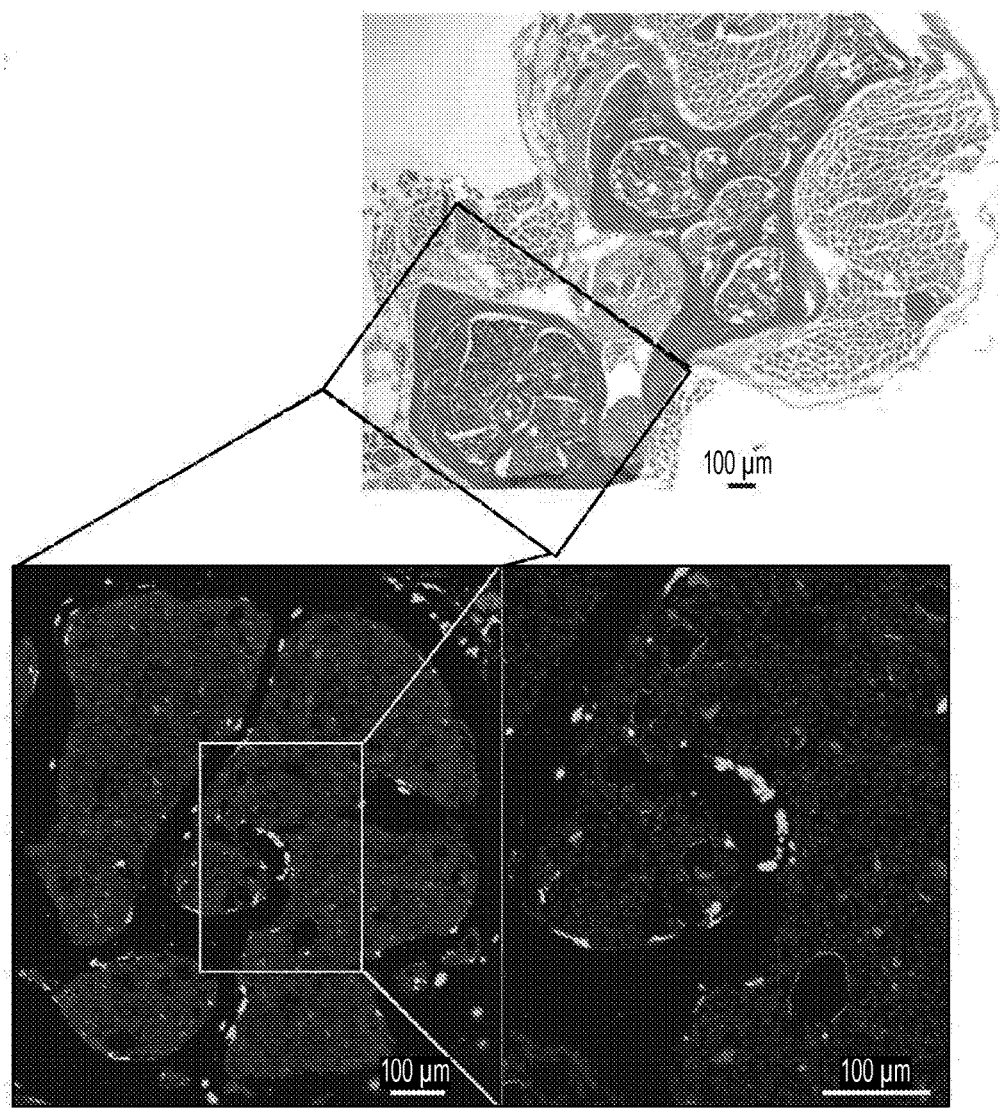
Figure 11G:
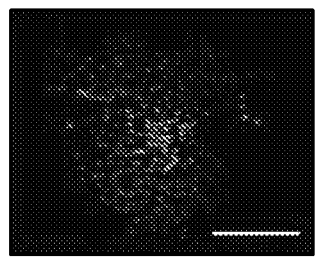
Figure 11H:
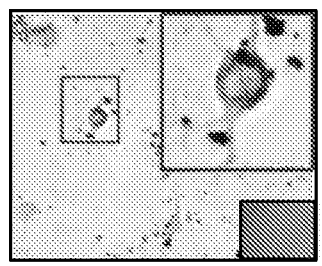
Figure 11I:
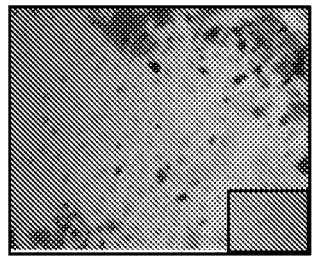
Figure 11J:
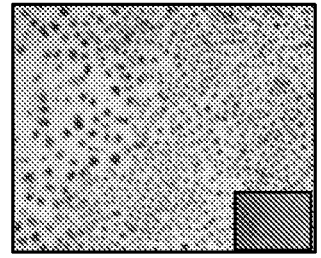

The expression of Grem1, Nes, Runx2, and Sox9 was measured by whole-mount in situ hybridization during the earliest stages of hind limb bud development, i.e., embryonic day (E) 9.5, E10.5, E11.5, and E12.5 (FIG. 4A). Grem1 was expressed at the onset of hind limb development, E9.5. Nes was not expressed within the hind limb at these stages. To confirm that Grem1 marked a multipotent mesenchymal stem/progenitor cell during development, tamoxifen was administered to pregnant Grem1-creERT;R26-LSL-TdTomato dams at E13.5. Consistent with the in situ hybridization findings, Grem1 was expressed within much of the primitive hind limb mesenchyme within the embryos and gave rise to almost all of the cells within the primitive mesenchyme and the primary spongiosa by E21 (FIG. 11E and FIG. 11F). Taken together, these results confirm that Grem1 expression marked a new, endogenous skeletal stem cell, in development and adulthood, which lacked any significant capacity for adipogenesis. As a result, it does not meet the minimal criteria for MSCs (Dominici et al., 2006). Thus, we named these Grem1 stem cells as osteochondroreticular "OCR stem cells" in reference to the earlier concept of the osteochondroprogenitor (Ducy et al., 1997).

Example 4

Perisinusoidal Nes-GFP+ Cells May Not Be Skeletal Stem Cells During Early Life

Figure 4B:
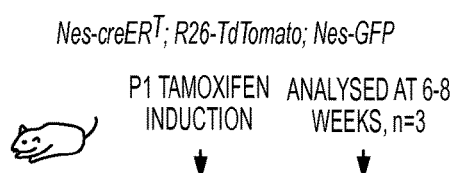
Figure 4C:
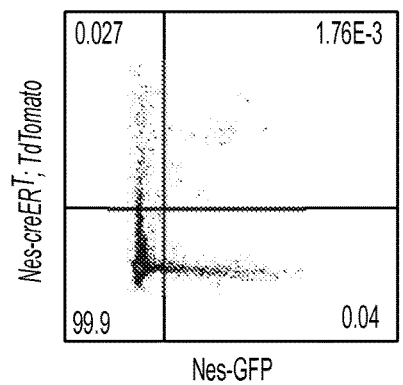
Figure 4D:
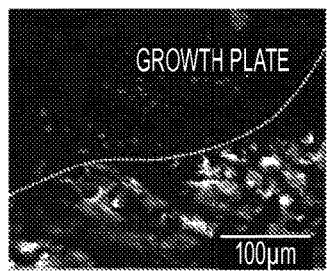
Figure 4E:
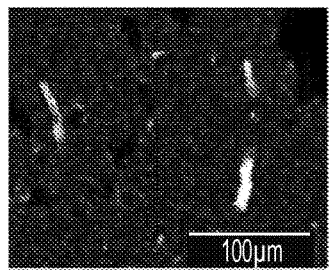
Figure 4F:
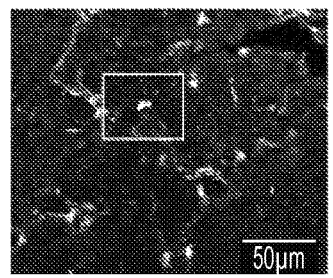
Figure 4G:
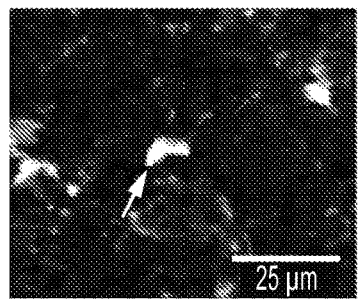
Figure 4H:
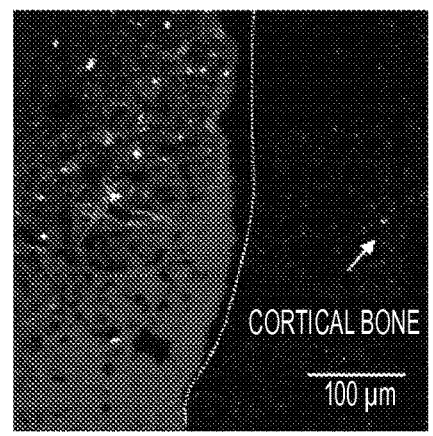

The previously published Nes-cre and Nes-creER$^T$ lines may not reliably identify the perisinusoidal Nes-GFP cells that are purported to be endogenous MSCs (Ding et al., 2012; Méndez- Ferrer et al., 2010). Thus, we used a different transgenic Ne-s-creER$^T$ line in an attempt to better understand the lineage potential of Nes-GFP+ perisinusoidal MSCs (Dranovsky et al., 2011). Compared to previously reported Nes reporter mouse lines, the transgenic Nes-creER$^T$ line used here had a different Nes regulatory sequence directing the expression of creER$^T$ (Dranovsky et al., 2011). Following P1 tamoxifen induction of Nes-creER$^T$;R26-LSL-TdTomato;Nes-GFP mice (FIG. 4B), Nes-creER$^T$ recombined R26-LSL-TdTomato in approximately 4% of all bone marrow Nes-GFP cells by 6-8 weeks (FIG. 4C). This included metaphyseal (FIG. 4D), periarteriolar (FIG. 4E), and perisinusoidal Nes-GFP cells (FIG. 4F-FIG. 4H). In keeping with previous perisinusoidal lineage-tracing studies, this Ne-s-creER$^T$ line did not generate cartilage or trabecular bone by 6-8 weeks (Ding et al., 2012; Mizoguchi et al., 2014). The only osteochondral cells that were traced consisted of rare, isolated osteocytes embedded within the diaphyseal cortical bone (FIG. 4H). Our findings suggest that perisinusoidal cells, labeled by Nes-GFP, may not be the principal skeletal stem cells during development or early postnatal life (Ding et al., 2012; Mizoguchi et al., 2014; Zhou et al., 2014). It is quite possible, however, that the endogenous Nes gene or other Nes-transgenic lines could be expressed in postnatal skeletal stem/progenitor cells, but that these cells were not captured by our lineage-tracing strategy in young (<8-week-old) mice.

Example 5

Grem$^+$ OCR Stem Cells Contribute to Fracture Repair

Figure 5C:
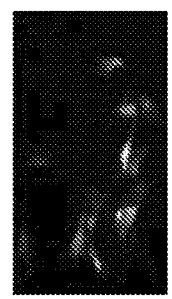
Figure 5D:
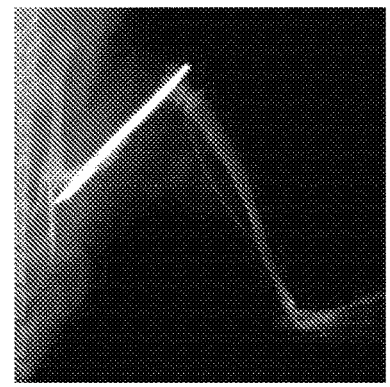
Figures 12A, 12B:
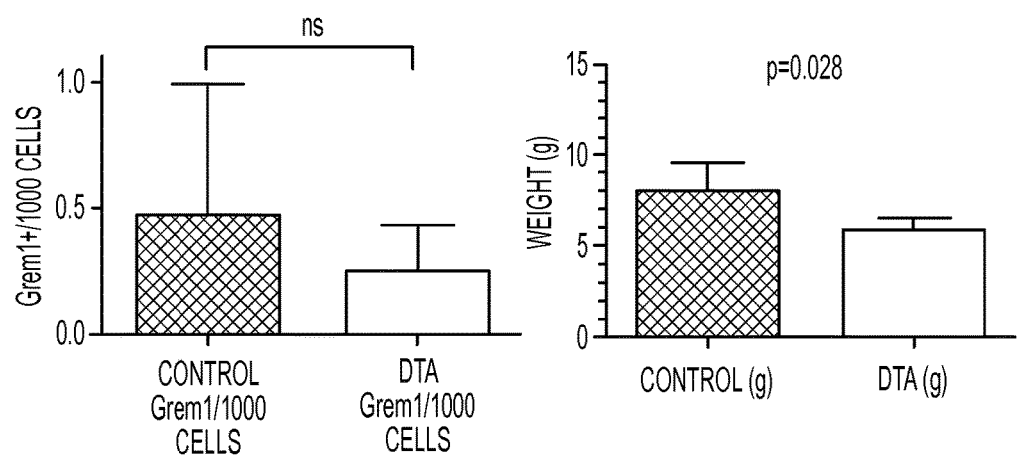
FIG. 12A-12F illustrates (A), Grem1-creERT; R26-LSL-ZsGreen;R26-LSL-DTA mice (DTA mice, n=3) vs Grem1-creERT;R26-LSL-ZsGreen littermates/related controls (control mice, n=10), tamoxifen induction at P9 (4 doses subcut, 2mg), sacrificed at P23. As one would expect, he DTA mice had a trend towards fewer green cells in the femur, but this did not reach significance, suggesting incomplete ablation. Nevertheless, the DTA mice were significantly lighter than the control mice, B. C, we performed microCT on these mice and there was significantly reduced femur volume in the DTA mice, and a trend towards reduced total bone volume. D, this was associated with reduced trabecular bone development on histology using thresholded measurements and analysis of epiphyseal trabecular bone area in ImageJ (p=0.04). E & F, Induction of Grem1+cells at E13.5 results in almost all of the primary spongiosa being labeled with red fluorescence by E21 (Grem1-creERT;R26-LSL-TdTomato, n=4).
Figure 12C:
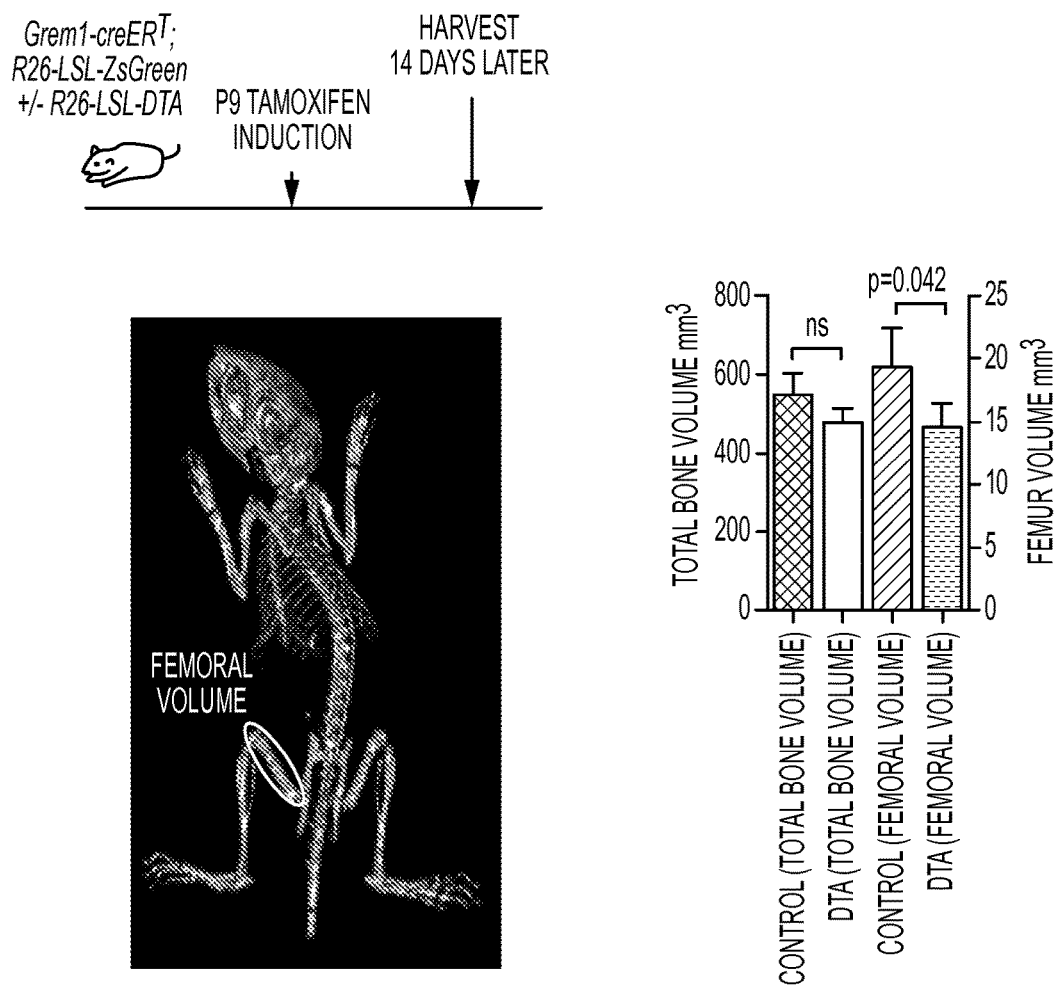
Figure 12D:
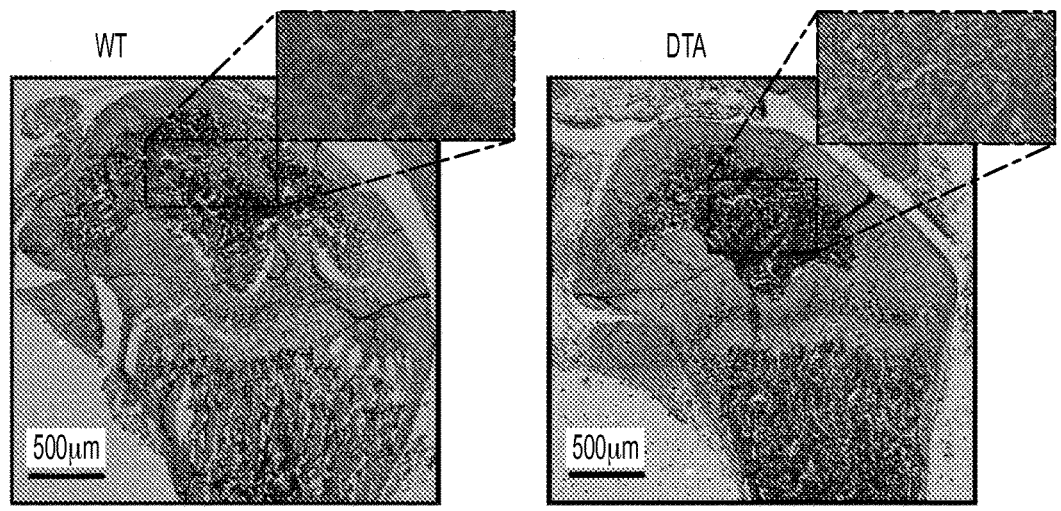
Figure 12D:
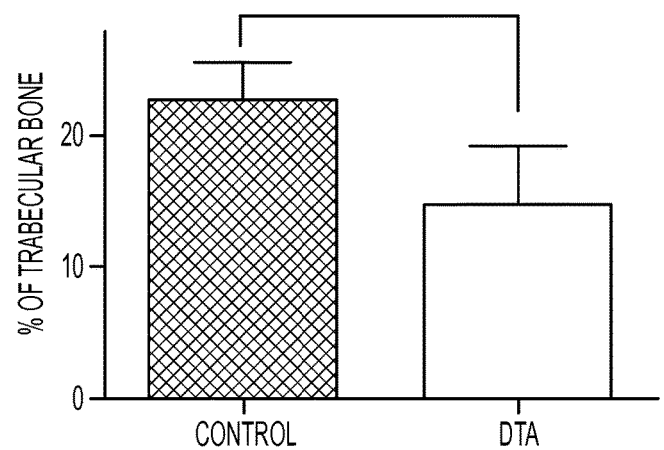

Adult Grem1$^-$ cells do not overlap with 2.3colGFP$^-$ osteoblasts. Grem1$^+$ cells are, however, adjacent to osteoblasts in vivo and during early adherent bone marrow stromal culture (FIG. 5B and FIG. 5C). Surgical fracture with internal fixation of the femur in Grem1-creER$^T$;R26-LSL-TdTomato;2.3colGFP mice (performed 1 week after adult induction with tamoxifen) (FIG. 5A and FIG. 5D) resulted in Grem1$^+$ OCR stem cell expansion and differentiation into 2.3colGFP-positive (and osteocalcin-positive, FIG. 12D osteoblasts and 2.3colGFP-negative, Sox9$^+$ chondrocytes within the fracture callus (FIG. 5E-5H and FIG. 12A-FIG. 12C). The Grem1$^+$ OCR stem cell lineage, as defined by red fluorescence, contributed approximately 28% of osteoblasts (red and 2.3colGFP green) and 14% of chondrocytes (defined by Sox9 immunostaining and/or by hematoxylin and eosin staining [H&E] on serial sections) within the fracture callus. Next, we tested whether Grem1$^+$ cells could be transplanted into the fracture site.

Figure 12E:
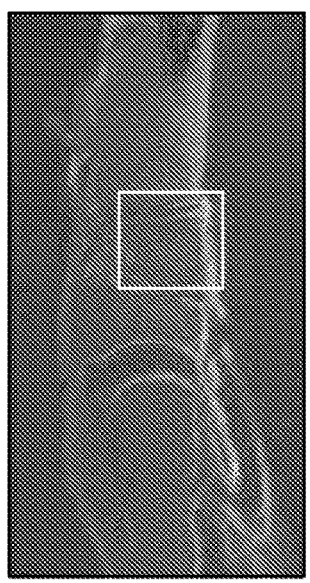
Figure 12F:
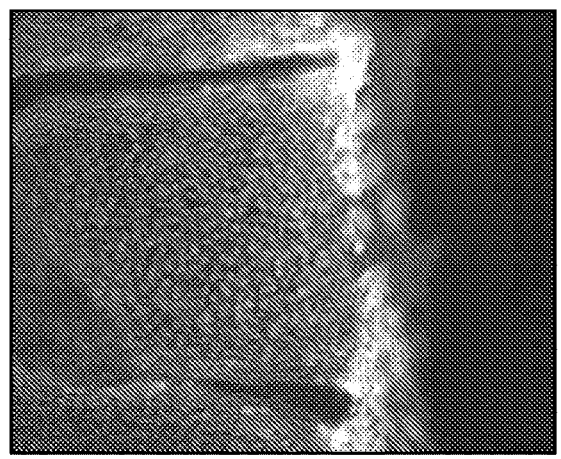
Figures 13A, 13B, 13C:
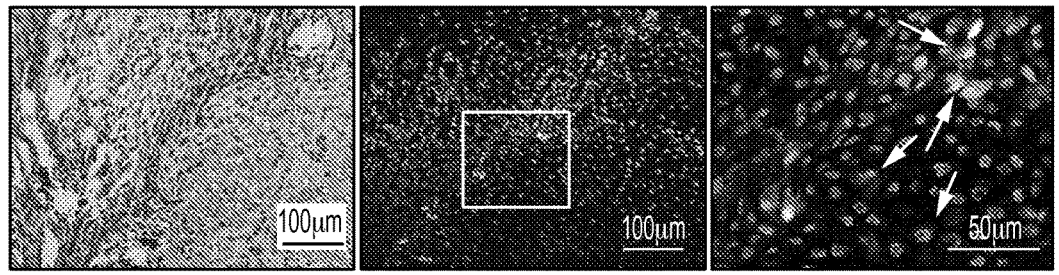
FIG. 13A-13E illustrates (A-C), Grem1-creERT;R26-LSL-TdTomato;2.3colGFP mice induced in adulthood 1 week before fracture prove that Grem1+ cells generate both bone and cartilage within the fracture callus (just another example of lineage tracing as shown in main FIG. 5, but from different mice). In C, the Grem1+ OCR-derived osteoblasts are yellow (white arrows) and the OCR stem cell derived chondrocytes are identified by yellow arrows. D, The fracture callus from another Grem1-creERT;R26-LSL-TdTomato;2.3colGFP was counterstained by anti-osteocalcin (white) as further proof that the Grem1 + OCR stem cells generate osteoblast (cells that are red (Grem1+derived), 2.3ColGFP+ (green) and osteocalcin+ (white). Triple+ (red, green, white cells) are identified by yellow arrows. The different colors are separated into distinct images to help with interpretation. E, This figure describes the serial transplantation experiment. Grem1+ OCR stem cells (red) from one of the fractures described in main FIG. 5, were recovered by callus culture and serially transplanted into a secondary fracture site. Again the secondary fracture showed significant TdTomato fluorescence specifically at the site of engraftment and serial H&E and fluorescence sections reveal the serial engraftment of the red Grem1 OCR stem cell derived cells into the secondary fracture callus (white arrows), and these cells were positive for Sox9 immunostaining (green) suggesting that they had differentiated into fracture callus chondrocytes (shown in high power, yellow arrows).
Figure 13D:
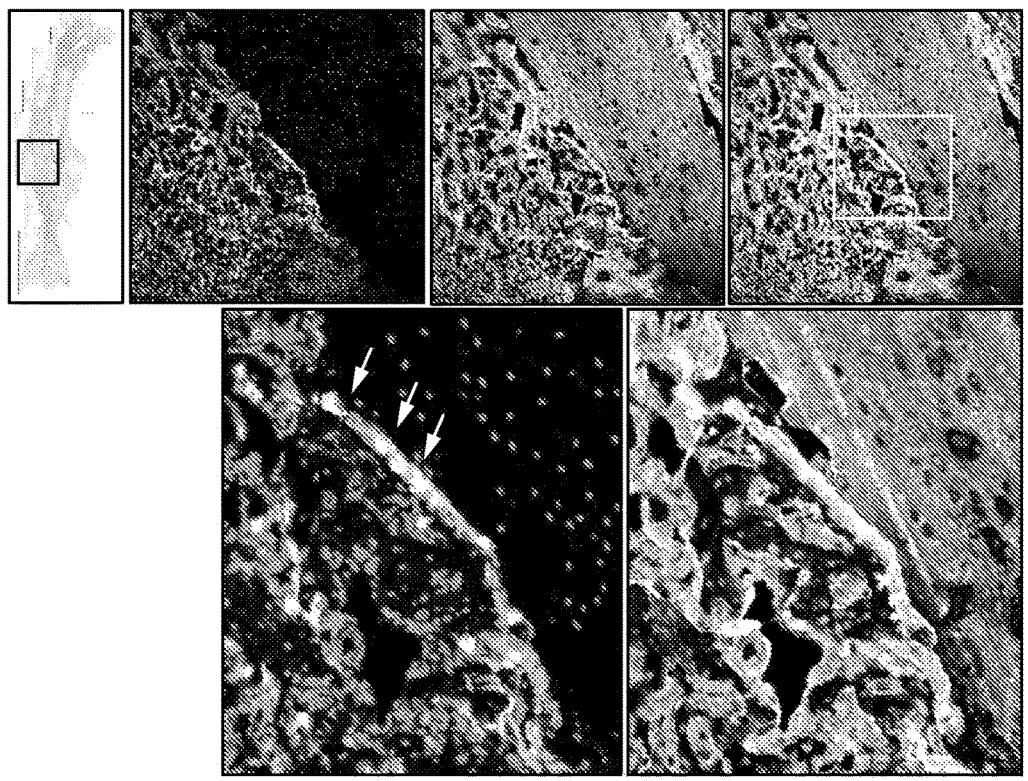
Figure 13E:
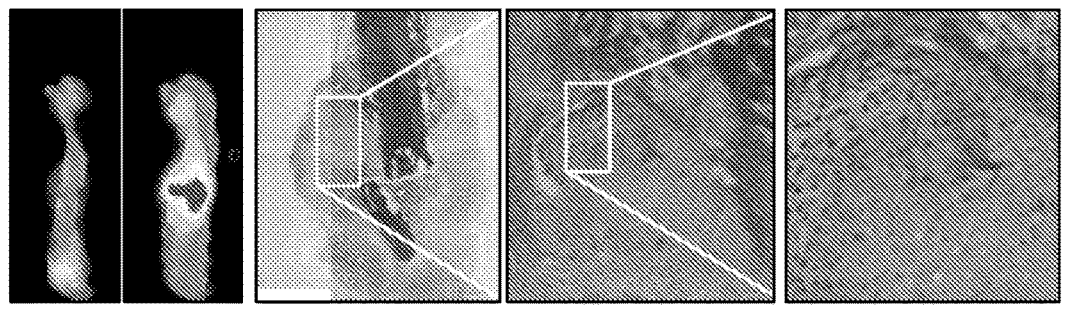
Figure 13E:
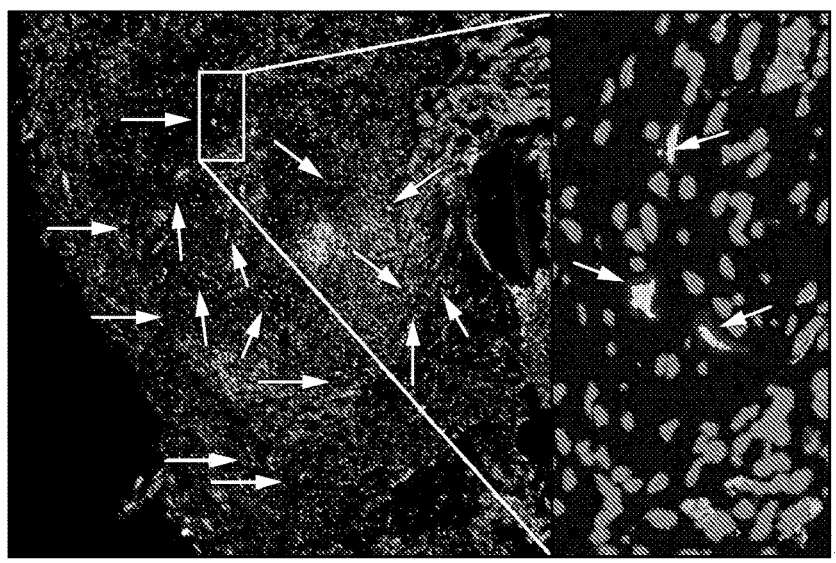

A clonal population of Grem1$^+$ OCR stem cells was expanded and harvested. This clone, mixed with hydrogel, was applied to the fracture site at the time of injury and engrafted into the callus of the recipient wild-type mice (FIG. 5I and FIG. 5J). The transplanted cells differentiated into osteoblasts (alkaline phosphatase-expressing) within the fracture callus (FIG. 5K). OCR stem cells self-renewed within the callus and were recovered from the recipient animals and rapidly expanded again in fracture callus cultures (FIG. 5L). The Grem1$^+$ OCR stem cells cultured from the fracture callus and expanded in vitro could be serially transplanted into a second fracture (FIG. 12E). Thus, Grem1 expression identifies developmental and adult, both physiological and reactive, endogenous OCR stem cells amenable to serial transplantation.

Example 6

Grem1 Expression Also Defines a New iRSC

Figure 6A:
Figure 6B:
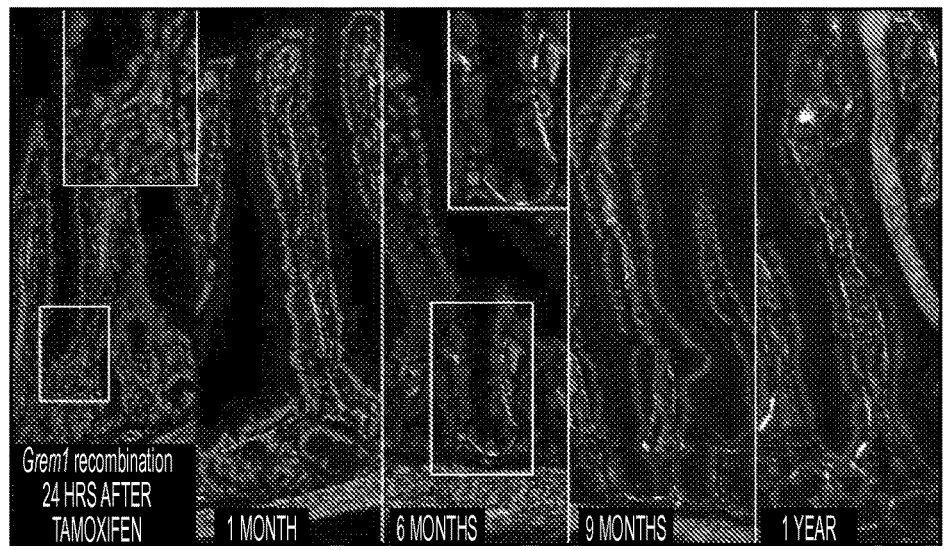
Figure 6C:
Figure 7:
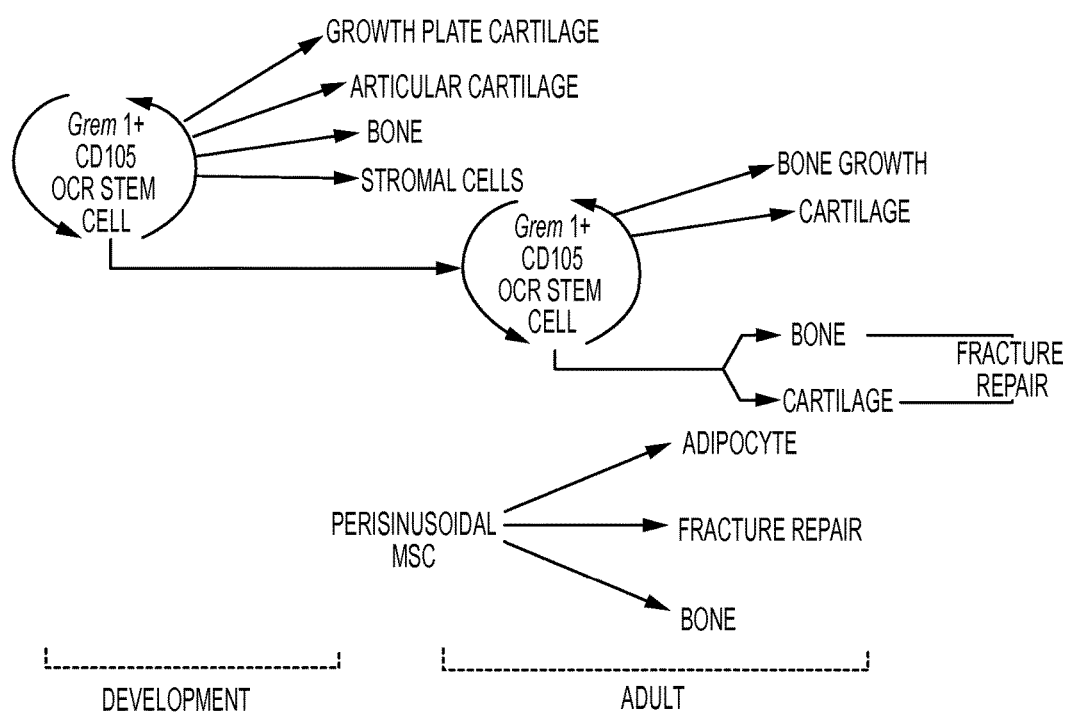
FIG. 7 is a schematic representation showing the OCR stem cell and the perisinusoidal MSC make a complementary contribution to skeletal development, adult homeostasis, and Repair.
Figure 8A:
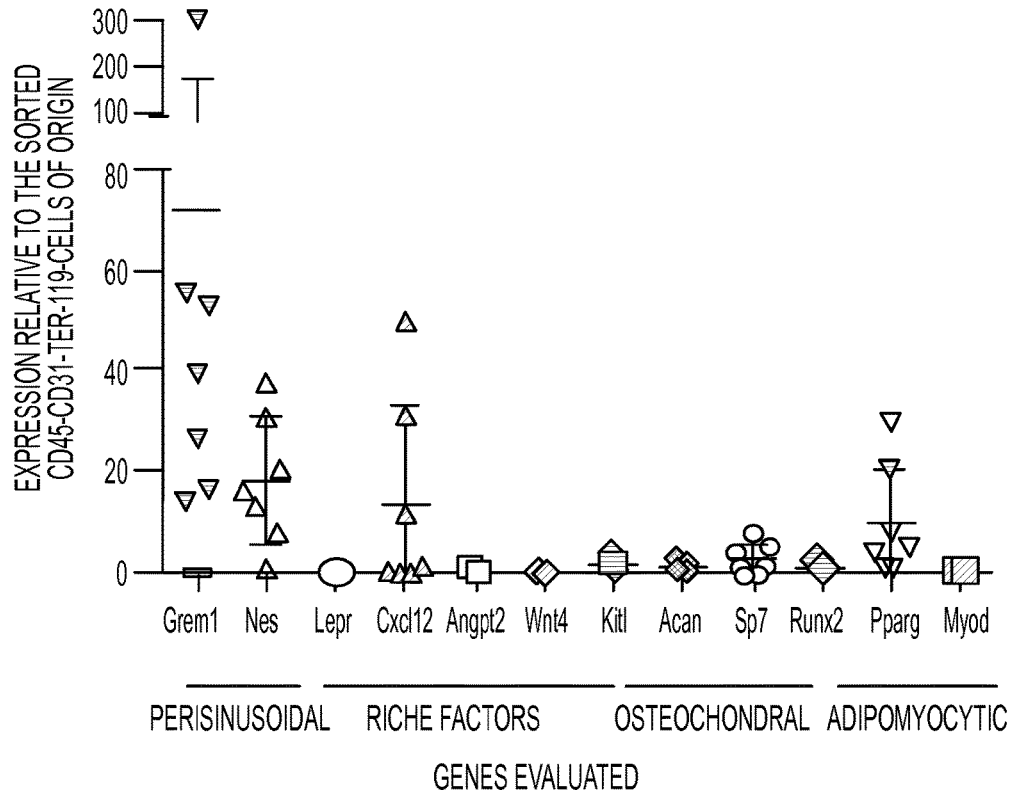
Figure 8B:
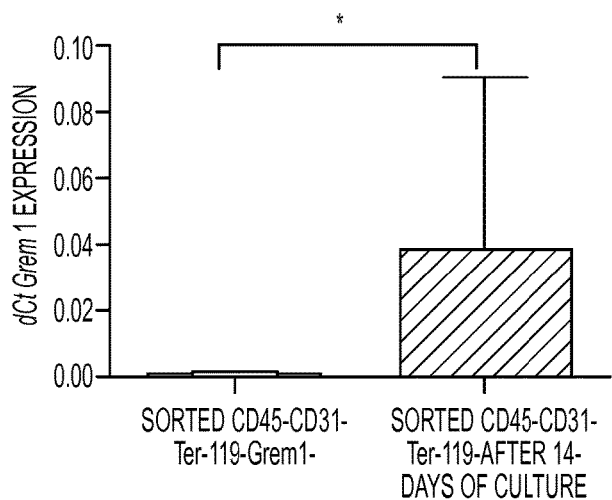
Figure 8C:
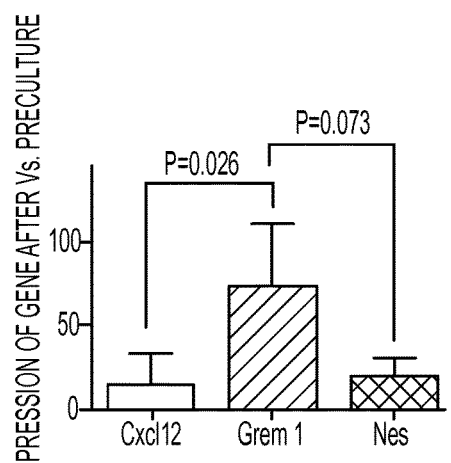

It was investigated whether Grem1 could also mark extramedullary connective tissue stem cells. The small intestine was selected as our extramedullary organ of interest because the gut is known to contain multipotent mesenchymal stromal cells (Powell et al., 2011). It is worth emphasizing that we searched for a connective tissue stem cell within the lamina propria and not for an epithelial stem cell, such as that previously identified by Lgr5 expression (Barker et al., 2007). Furthermore, the small intestine does not contain bone and cartilage, and thus it was not expected to find a bona fide OCR stem cell. Rather, testing for an organ-relevant connective tissue stem cell, sharing Grem1 expression and the defining stem cell characteristics of self-renewal and multipotentiality was of interest. The connective tissue immediately beneath the intestinal epithelium is a mesenchymal sheath that invests the entire intestinal gland (Powell et al., 2011). Adult Grem1 recombination (24 hr after 6 mg of tamoxifen by oral gavage, Grem1-creER$^T$; R26-mT/mG) identified single cells (Grem1$^+$=green) immediately beneath the epithelium at the junction between the small-intestinal crypt and villus, a region known as the intestinal isthmus (FIG. 6A and FIG. 6B). In situ hybridization confirmed Grem1 expression within periepithelial isthmus cells, and these cells were also positive in the Grem1-LacZknockin line (FIG. 14A-FIG. 14F) (Khokha et al., 2003).

Figure 14A:
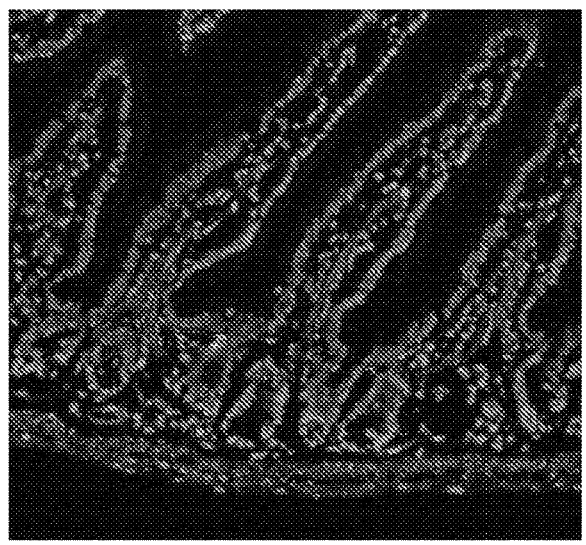
FIG. 14A-14P illustrates (A) Small intestine of adult Grem1-creERT;R26-mT/mG mice 24 hours after tamoxifen induction recombine in single, periepithelial cells at the small intestinal isthmus. B-E the same cells were positive by Grem1 in situ hybridization. F, Grem1-LacZ knock in mouse reported Grem1 expression in the same periepithelial cells at the isthmus (black arrows). In addition, the Grem1-LacZ mice also were positive for LacZ within the muscularis propria, which was occasionally positive within adult Grem1-creERT;fluorescent reporter mice. But, in keeping with our Grem1-creERT line, there were never any Grem1-LacZ positive cells in the lamina propria of the small intestinal villus. G, Grem1 recombined cells (Green) divided slowly, BrdU incorporation, red, over 1 month of continuous BrdU administered via the drinking water. Given the extended BrdU administration, all of the epithelial cells have incorporated BrdU. H, many of the traced (green) Grem1-lineage periepithelial cells expressed Ng2 a mesenchymal and pericytic marker (also known as Cspg4), which was also elevated in our bone marrow microarray. I, Grem1creERT; R26-LSL-TdTomato mice induced at P1 and then the jejunum was examined by wholemount confocal microscopy. Patches of glands surrounded by Grem1+ iRSC derived (red) mesenchymal sheaths can be found. The Grem1+ iRSC-derived sheath (red) is intimately related to, but distinct from, the overlying s100b+ (I) and Nes-GFP+ (J) glial sheath. The Grem1+ iRSC-derived sheath is more closely related to the epithelium, than the glial sheath. K, the intimacy between the Grem1 lineage and the epithelium was best shown by transmission electron microscopy where long cellular processes (red arrows) are very closely opposed to the overlying epithelium, here at the small intestinal crypt base. (L), Grem1-creERT;R26-mT/mG mice induced with 6mg of tamoxifen once in adulthood, (6-8 weeks) still have fully iRSC-derived (green) small intestinal gland periepithelial mesenchyme (here in the jejunum) at 2 years, confirming self-renewal of the Grem1 iRSCs. M, Grem1-creERT;R26-Confetti mice, induced at P1. R26-Confetti displayed less robust recombination of the reporter than the other reporters we used. Nevertheless, occasional clones of iRSCs could be tracked to confirm that the Grem1 sheath is derived from one iRSC and that the mesenchymal unit in the small intestine conforms to the epithelial unit, i.e. the periepithelial mesenchymal sheath from one crypt contributes to multiple associated villi, just as in the epithelial compartment. Shown here, with a recombined yellow clone from different sides of the same small intestinal crypt tracked across serial (5 µm) sections contributing to the periepithelial sheath in two distinct villi (one villi identified by white, the other by red, arrows). N, The red Grem1 iRSCs from Grem1creERT;R26-LSL-TdTomato mice, can be isolated and cultured to form in vitro clones, confirming that Grem1 iRSCs contribute to small intestinal CFU-Fs. O, expression of Grem1-creERT also identified stem/progenitor populations in the hair follicle/skin and the stomach. P, Tissue engineering: Another example of Grem1+ cells (red) derived from donor Grem1+ iRSCs within the harvested TESI. Shows that the periepithelial mesenchymal sheath (red) is derived from the donor Grem1 cells (red), dotted white line outlines the regenerated intestinal epithelium within the TESI.
Figure 14B:
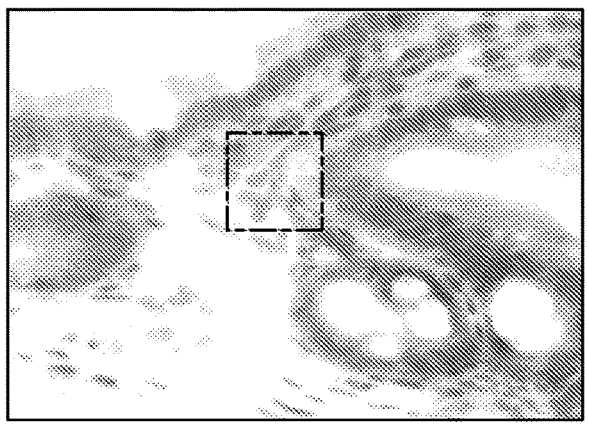
Figure 14C:
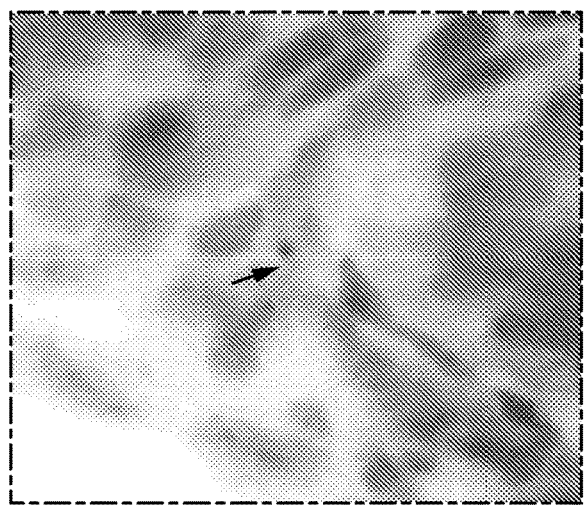
Figure 14D:
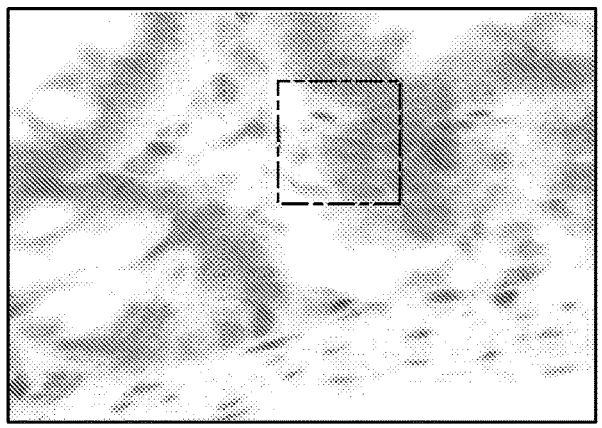
Figure 14E:
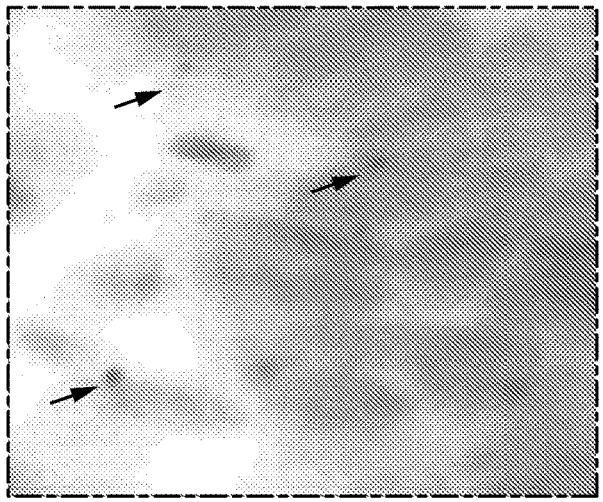
Figure 14F:
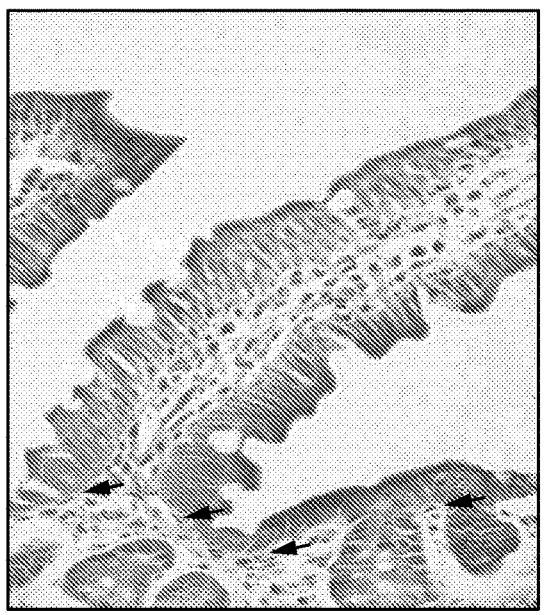
Figure 14G:
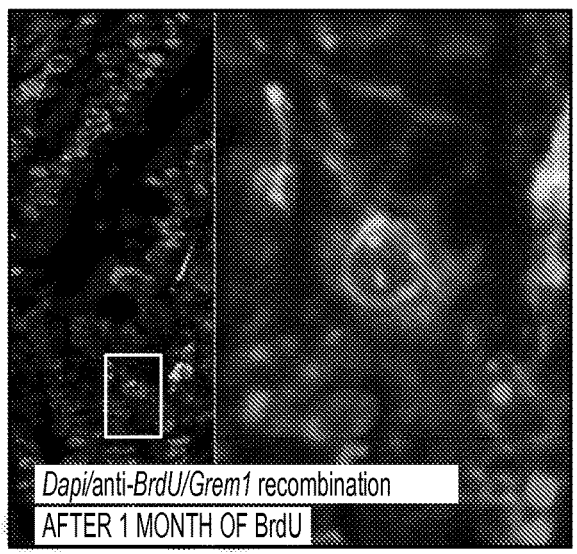
Figure 14H:
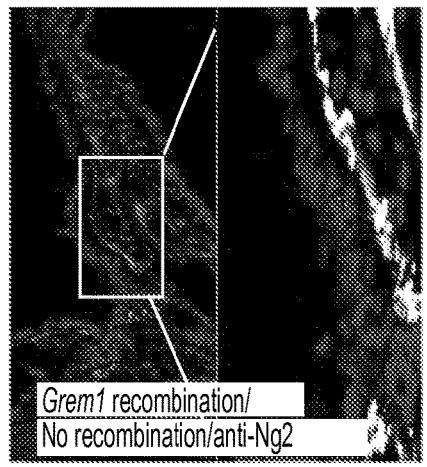
Figure 14I:
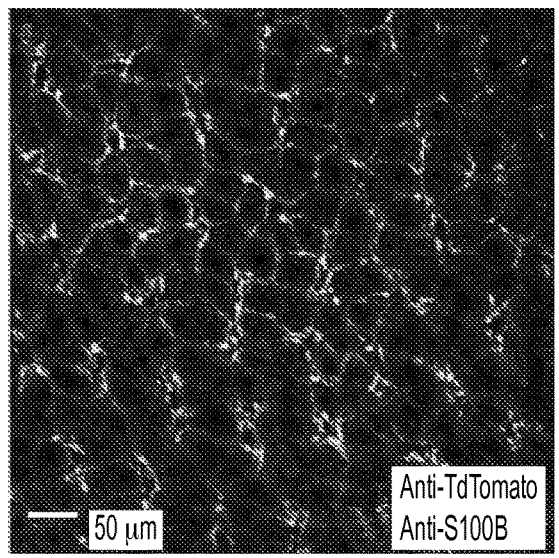
Figure 14J:
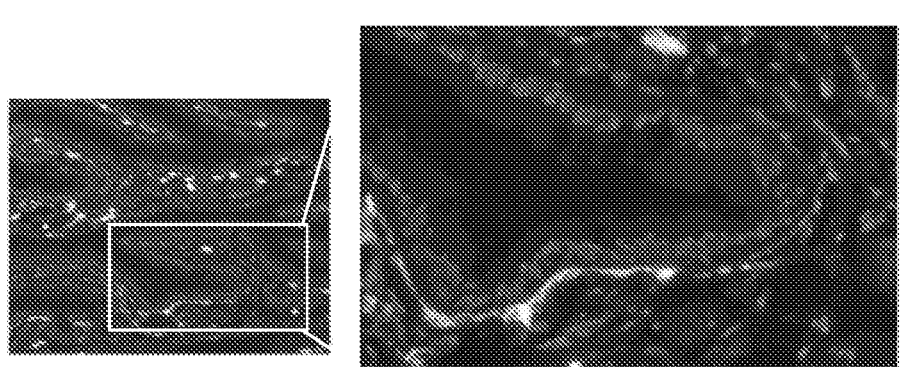
Figure 14L:
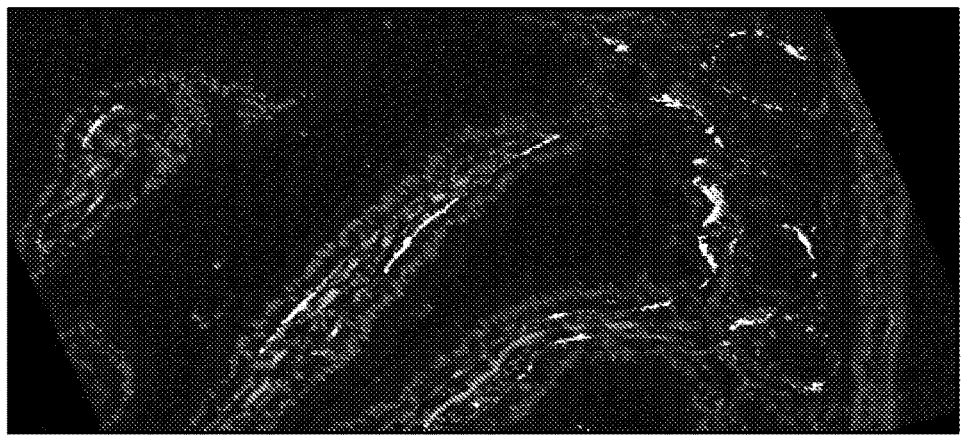
Figure 14K:
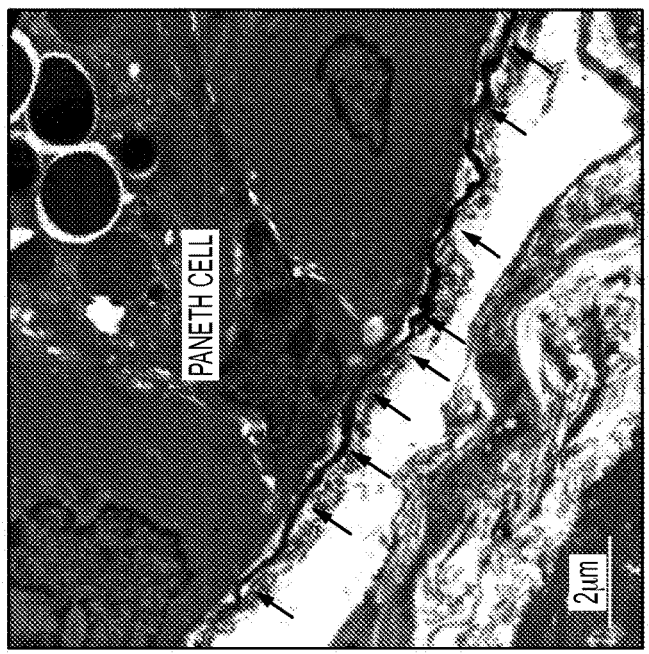
Figure 14M:
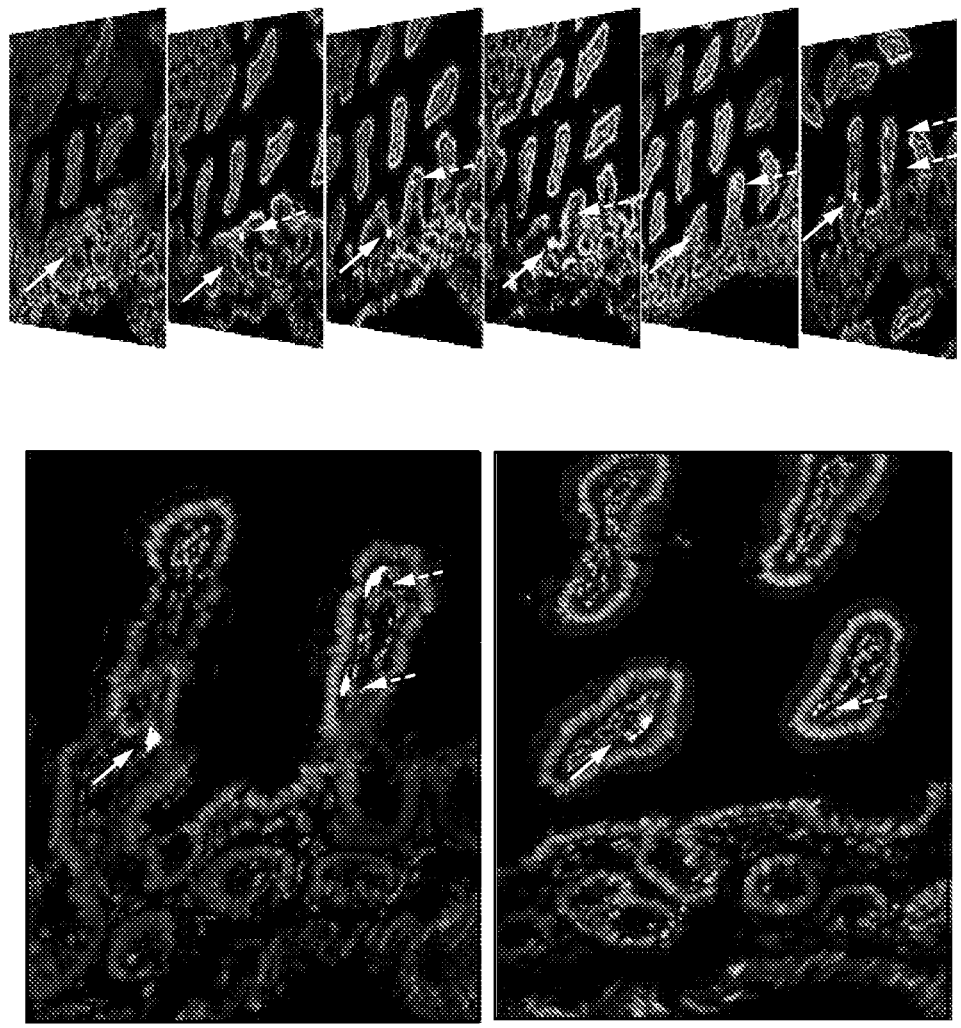
Figure 14N:
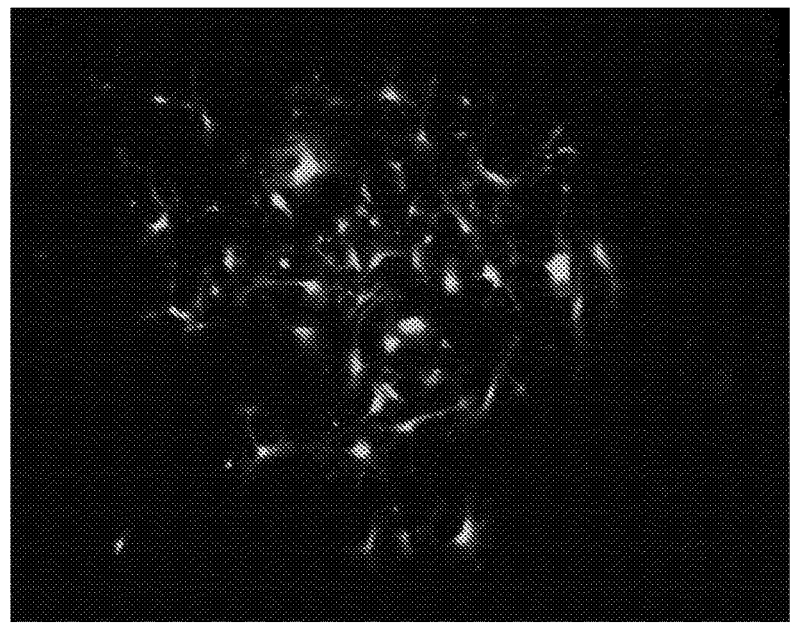
Figure 14O:
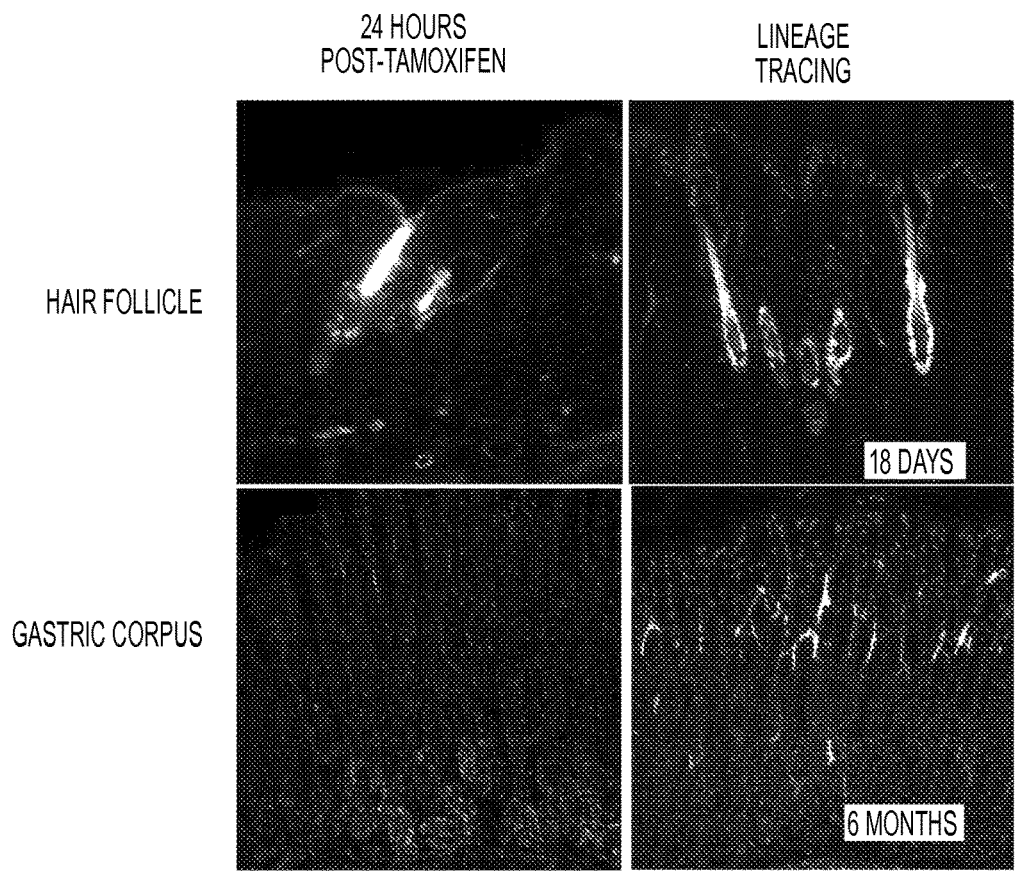

Single periepithelial Grem1 cells divided slowly (BrdU incorporation over 1 month of continuous dosing; FIG. 14G). Over time, the fluorescently tagged Grem1$^+$ cells gave rise to reticular, periepithelial mesenchymal lineages throughout both the crypt and villus sheaths (FIG. 6B-FIG. 6E). The Grem1$^+$ cells differentiated into both Acta2-positive myofibroblasts (FIG. 6F) and Acta2- negative, but Ng2-positive, stromal cells (FIG. 14H). Grem1 cells gave rise to an intricate reticular network of cells that invested the entire gland (FIG. 6B- FIG. 6E,). The Grem1 lineage was distinct from the closely associated s100b (FIG. 14I) and Nes-GFP positive periepithelial glial sheath (FIG. 14J) (Belkind-Gerson et al., 2013). The Grem1 cell lineage was related to the overlying intestinal epithelium (FIG. 6G and FIG. 14K). After 6 to 9 months, intestinal Grem1 cells had expanded to give rise to the mesenchymal sheath subjacent to the Lgr5$^+$ crypt base columnar stem cell zone (FIG. 6B, FIG. 6C, and FIG. 6E) (Barker et al., 2007). After 12 months, the cells had also renewed the periepithelial mesenchymal sheath to the tip of the villi (FIG. 6B). The Grem1$^+$ cells at the isthmus self- renewed so that their fluorescently tagged lineage persisted across the entire crypt-villus axis for at least 2 years after adult tamoxifen induction (FIG. 14L). Perinatal induction at P1 led to accelerated intestinal mesenchymal tracing (at 6 weeks), providing further proof of the clonality of the Grem1 lineage within the mesenchymal sheath (Grem1-creER$^T$;R26-Confetti mice; FIG. 14-M). The Grem1 lineage also identified small-intestinal CFU-Fs (FIG. 14N). Similar patterns of lineage tracing were evident throughout the entire gastrointestinal tract, including the stomach (FIG. 14O). Grem1 also identified a progenitor population within the skin (FIG. 14O). The exact nature of these cells, however, requires further study.

Figure 14P:
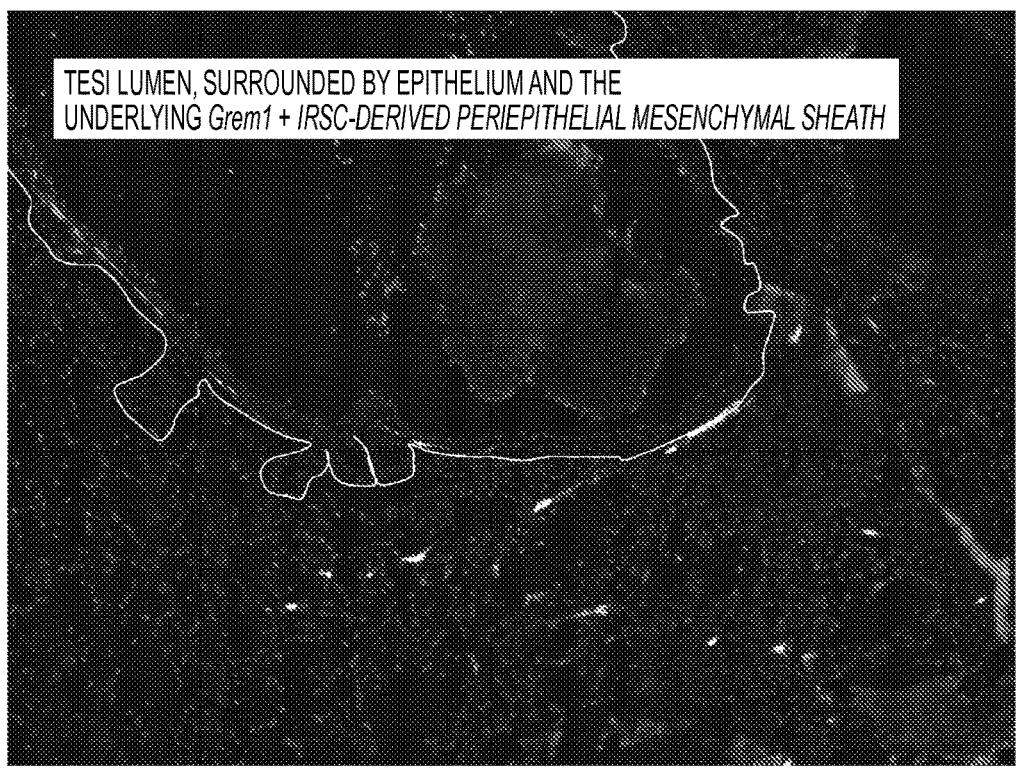

Extending the concept of connective tissue stem cells to extramedullary mesenchyme, however, requires that the model be rigorously validated in vivo. A protocol was adopted for generating tissue-engineered small intestines (TESIs) to test whether Grem1$^+$ intestinal mesenchymal cells could be transplanted to generate the small-intestinal, periepithelial mesenchymal sheath within the recipient's TESI graft (Levin et al., 2013). Grem1-creER$^T$;R26-LSL-TdTomato donor small-intestinal organoid units were transplanted into the omentum of recipient wild- type mice. Only one or two Grem1$^+$ cells were present within the harvested donor units (FIGS. 6H), but they were able to expand and restore the intestinal mesenchymal sheath in the TESI (FIGS. 6I and FIG. 14P). Thus, small-intestinal Grem1$^+$ cells self-renew and clonally generate multiple distinct, compartment-relevant mesenchymal lineages and can be transplanted to recapitulate the periepithelial mesenchymal sheath, confirming that they are connective tissue stem cells. In this context, they are referred to as iRSCs. The term, iRSCs, reflects their morphology and the reticular network formed by these cells and in reference to their Grem1-expressing reticular counter- parts in the bone marrow.

Although the present invention has been described in considerable detail with reference to certain preferred embodiments, other embodiments are possible. Therefore, the spirit and scope of the appended claims should not be limited to the description of the preferred embodiments contained herein.

TABLE 1A

| Gene | Purpose | Sequence (5'-3')/Sequence name (IDT descriptor) | |
|---|---|---|---|
| F-Grem1 recombineering primer | Recombineering | GATTTTTACTAAATAACTTTCTTATTGTCTGTG TCCCCCTCTCTTTGTCCTTTGTCTAGAATGTC CAATTTACTGACCGTACA | SEQ ID NO.: 1 |
| R-Grem1 recombineering primer | Recombineering | GTTGGCAGTAGGGTCCCCAGGAGGAGAAGC AACGCTCCCACAGTGTATGCGGTGCGATTAT TATGTACCTGACTGATGAAGTT | SEQ ID NO.: 2 |
| F-Grem1-creERT | Genotyping | CTG TGT CGA ATT ACT CAG TTT GAT G | SEQ ID NO.: 3 |
| R-Grem1-creERT | Genotyping | AAT GTT GCT GGA TAG TTT TTA CTG C | SEQ ID NO.: 4 |
| F-Grem1-LacZ | Genotyping | ATCCTCTGCATGGTCAGGTC | SEQ ID NO.: 5 |
| R-Grem1-LacZ | Genotyping | CGTGGCCTGATTCATTCC | SEQ ID NO.: 6 |
| F-R26-TdTomato or ZsGreen (the WPRE) | Genotyping | ACT GTG TTT GCT GAC GCA AC | SEQ ID NO.: 7 |
| R-R26-TdTomato or ZsGreen (the WPRE) | Genotyping | CAA CAC CAC GGA ATT GTC AG | SEQ ID NO.: 8 |
| F-Nes-GFP or 2.3ColGFP or R26-Confetti (the GFP) | Genotyping | GAG CTG AAG GGC ATC GAC TTC AAG | SEQ ID NO.: 9 |
| R-Nes-GFP or 2.3ColGFP or R26-Confetti (the GFP) | Genotyping | GGA CTG GGT GCT CAG GTA GTG G | SEQ ID NO.: 10 |
| F-Nes-CreERT | Genotyping | GCG GCA TGG TGC AAG TTG AAT | SEQ ID NO.: 11 |
| R-Nes-CreERT | Genotyping | CGT TCA CCG GCA TCA ACG TTT | SEQ ID NO.: 12 |
| F-R26-iDTA | Genotyping | ACC TGG TTA TGT AGA TTC CAT TCA A | SEQ ID NO.: 13 |
| R-R26-iDTA | Genotyping | CAG AAG TAA GGT TCC TTC ACA AAG A | SEQ ID NO.: 14 |
| Acan | qPCR | Mm.PT.56a.10174685 | |
| Angpt2 | qPCR | Mm.PT.56a.29139310 | |
| Bmp2 | qPCR | Mm.PT.58.10419414 | |
| Cspg4 | qPCR | Mm.PT.56a.29461721 | |
| Cxcl12 | qPCR | Mm.PT.56a.7098583.g | |
| Fap | qPCR | Mm.PT.56a.31960536 | |
| Gapdh | qPCR | Mm.PT.39a.1 | |
| Grem1 | qPCR | Mm.PT.53a.31803129 | |
| Id2 | qPCR | Mm.PT.58.13116812.g | |
| KitI | qPCR | Mm.PT.56a.6382703 | |
| Klf4 | qPCR | Mm.PT.56a.10779296 | |
| Lepr | qPCR | Mm.PT.56a.33275723 | |

TABLE 1A-continued

| Gene | Purpose | Sequence (5'-3')/Sequence name (IDT descriptor) |
|---|---|---|
| Myod | qPCR | Mm.PT.56a.8193525 |
| Nes | qPCR | Mm.PT.56a.5953887 |
| Pparg | qPCR | Mm.PT.56a.31161924 |
| Runx2 | qPCR | Mm.PT.56a.31234632.g |
| Sox9 | qPCR | Mm.PT.56a.42739087 |
| Sp7 (Osterix) | qPCR | Mm.PT.56a.10898265 |
| Wnt4 | qPCR | Mm.PT.56a.8723468 |
| GAPDH (human) | qPCR | Hs.PT.39a.22214836 |
| GREM1 (human) | qPCR | Hs.PT.53a.26917089.g |
| Acta2-RFP and R26-mT/mG | Phenotyping | Carriers were detected by red fluorescence of the tail |

TABLE 1B

Mice used in our study

| Mouse line used | Reference | Received from | Description |
|---|---|---|---|
| Grem1-creER$^T$ | Published here | Generated in the Wang lab. | A BAC transgenic in which the regulatory elements of Grem1 drive expression of a tamoxifen inducible Cre recombinase. Grem1 expressing cells express Cre recombinase that can, following binding of tamoxifen, translocate to the nucleus to recombine and thus activate fluorescent reporters or the diphtheria toxin subunit A lines described below. |
| Grem1-LacZ | Khokha et al, 2003 | investigator | A LacZ reporter is knocked in to the endogenous Grem1 locus. Cells that express Grem1 can be detected by LacZ activity. |
| Nes-creER$^T$ | Dranovsky et al., 2011 | investigator | A transgenic line in which a short regulatory sequence of Nes drives expression of a tamoxifen inducible Cre recombinase. Following administration of tamoxifen, Nes expressing cells express Cre recombinase that can translocate to the nucleus to recombine and thus activate fluorescent reporters. In this line a 5.3 kb region drives the CreERT2 upstream of the transcriptional start site of the Nestin gene. This fragment is fused to the CreERT2 followed by a |

TABLE 1B-continued

Mice used in our study

| Mouse line used | Reference | Received from | Description |
| --- | --- | --- | --- |
| | | | polyA tail and then a 653bp region of the 2nd intron (corresponding to base pare positions 2880–>3533 downstream of the start site). |
| Nes-GFP | Mignone et al., 2004 | investigator | A transgenic line in which a short regulatory sequence of Nes drives GFP expression. |
| 2.3ColGFP | Kalajzic et al., 2002 | JAX stock no. 13134 | A transgenic line in which a short (2.3 kb) regulatory sequence of rat Col1a1 drives GFP expression. This line is used to identify committed osteoblasts in mice. |
| Acta2-RFP | Magness et al., 2004 | investigator | A transgenic line in which a short regulatory sequence of Acta2 drives RFP expression. |
| R26-LSL-TdTomato | Madisen et al., 2010 | JAX stock no. 7909 | A cre recombinase activated red fluorescent reporter knocked into the Rosa26 locus. |
| R26-LSL-ZsGreen | Madisen et al., 2010 | JAX stock no. 7906 | A cre recombinase activated green fluorescent reporter knocked into the Rosa26 locus. |
| R26-LSL-mT/mG | Muzumdar et al., 2007 | JAX stock no. 7676 | A cre recombinase activated green fluorescent reporter knocked into the Rosa26 locus. Prior to recombination all cells express a red fluorescent protein, which allows easier appreciation of tissue architecture on fluorescent microscopy. |
| R26-LSL-Confetti | Snippert et al., 2010 | JAX stock no. 17492 | A cre recombinase activated fluorescent reporter knocked into the Rosa26 locus. The value of this reporter is that one of 4 fluorescent tags is expressed randomly following recombination, either, YFP, RFP, mCFP or nGFP. This allows clones to be mapped in vivo. |
| R26-LSL-DTA | Voehringer et al., 2008 | JAX stock no. 9669 | A cre recombinase activated diphtheria toxin subunit A expressing construct knocked into the Rosa26 locus. This allowed cell specific programmed cell death. |

TABLE 1C

Other mice previously reported as marking mesenchymal stem/progenitor cells, not included in our study

| Mouse line used | Reported in | Description |
|---|---|---|
| Lepr-cre | Ding et al, 2012; Zhouet al 2014, Mizoguchi et al, 2014. | Lepr-cre is a knock-in, constitutive Cre line that primarily identifies perisinusoidal mesenchymal cells in the bone marrow. Across 3 papers the perisinusoidal cells it marks have been shown to not generate bone or cartilage in early postnatal life, but that in later life beginning around 2 months, Lepr+ perisinusoidal cells begin to differentiate into bone and adipocytes and, in fracture callus, chondrocytes. |
| Nes-Cre | Mendez-Ferrer, et al, 2010; first published in Tranche et al, 1999. | Lineage tracing of bone and cartilage has been reported from this line, albeit that the recombination may not perfectly mimic the perisinusoidal distribution of Nes-GFP. |
| Nes-CreERT | Mendez-Ferrer, et al, 2010; first published in Balordi & Fishell, 2007. | Lineage tracing of bone and cartilage has been reported from this line, albeit that the recombination may again not perfectly mimic the perisinusoidal distribution of Nes-GFP. |
| Osx-Cre | Mizoguchi et al, 2014. Maes et al, 2010, Park, et al 2012. | Osterix (Sp7) is a broad mesenchymal marker, but in adulthood is recognized as an early, but non-self-renewing, osteolineage marker. However, Osx is expressed in cell populations of varying potential throughout development and it was recently shown that perinatal Osx expressing cells (P5) are long-lived with bone and stromal potential. |
| Ng2-CreERT | Kunisaki et al, 2013; Feng, et al, 2011. | In the adult murine bone marrow Ng2-CreER$^T$ identifies periarteriolar cells, important for the HSC niche. In the tooth Ng2+ cells are mesenchymal stem/progenitor cells generating odontoblasts. |
| Acta2-CreER | Grcevic et al, 2012. | Acta2 expressing cells act as in vitro and in vivo mesenchymal stem/progenitor cells. Acta2 is also expressed in smooth muscle and thus is probably expressed in both differentiated and less differentiated mesenchymal populations. |
| Prx1-Cre | Logan et al, 2002. | Prx1 is expressed in early limb bud mesoderm and as a constitutive Cre will thus trace all lineages derived from limb bud mesoderm including bone, stroma and cartilage. It has been used in studies requiring broad mesodermal tracing and conditional knockouts. |

TABLE 1D

Antibodies

| Primary antibody | Clone | Purpose | Manufacturer | Catalog number | Conjugated/Biotinylated | Dilution |
|---|---|---|---|---|---|---|
| Sca-1 | D7 | FC | BioLegend | 108116 | Alexa Fluor ® 488 | 0.388888889 |
| CD105 | MJ7/18 | FC | BioLegend | 120405 | Alexa Fluor ® 488 | 0.388888889 |
| CD31 | MEC13.3 | FC | BioLegend | 102509 | APC | 0.388888889 |
| CD45 | 30-F11 | FC | BioLegend | 103111 | APC | 0.388888889 |
| TER-119 | TER-119 | FC | BioLegend | 116211 | APC | 0.388888889 |
| Sca-1 | D7 | FC | BioLegend | 108125 | APC/Cy7 | 0.388888889 |
| CD140a | APA5 | FC | BioLegend | 135905 | PE | 0.388888889 |
| CD105 | MJ7/18 | FC/IF | BioLegend | 120404 | BIOTINYLATED | 0.388888889 |
| CD105 | MJ7/18 | FC | BioLegend | 120410 | PE/Cy7 | 0.388888889 |
| CD140a | APA5 | FC | BioLegend | 135910 | BIOTINYLATED | 0.388888889 |
| GFP | Polyclonal | IF | Invitrogen | A-11122 | None (rabbit anti-GFP) | 0.180555556 |
| CD31 | MEG 13.3 | IF | BD Biosciences | 550274 | None (LEW rat host anti-mouse CD31) | 0.180555556 |
| Sox9 | Polyclonal | IF | Millipore | ABE571 | None | 0.180555556 |
| Osteocalcin | Polyclonal | IF | Takara | M173 | None | 0.180555556 |
| Perilipin | D1D8 | IF | Cell Signalling | 9349 | None | 0.180555556 |
| pSmad1,5 | 31H14L11 | FC | Invitrogen | 700047 | None | 0.388888889 |
| Ng2 | polyclonal | IF | Millipore | AB5320 | None | 0.180555556 |
| TdTomato | Polyclonal | TEM | Clontech | 632496 | None (rabbit anti-dsRed worked for TdTomato) | 0.388888889 |

TABLE 1E

Bmp2 pathway Genes, Grem1+VsGrem1- fdr < .05

| Symbol | Description | Log₂ FC |
|---|---|---|
| Acvrl | activin A receptor, type 1 | 6.94 |
| Bmp2 | bone morphogenetic protein 2 | 5.79 |
| Bmp5 | bone morphogenetic protein 5 | 4.36 |
| Bmp6 | bone morphogenetic protein 6 | 2.18 |
| Id2 | inhibitor of DNA binding 2 | 2.56 |

TABLE 1F

Grem1+ vs Grem1- Signficant KEGG Pathways

| Rank | Name | ID | pSize | onArray |
|---|---|---|---|---|
| 1 | ECM-receptor interaction | 4512 | 87 | 85 |
| 2 | PI3K-Akt signaling pathway | 4151 | 356 | 333 |
| 3 | Focal adhesion | 4510 | 205 | 203 |
| 4 | Fc gamma R-mediated phagocytosis | 4666 | 89 | 87 |
| 5 | Natural killer cell mediated cytotoxicity | 4650 | 125 | 112 |
| 6 | Osteoclast differentiation | 4380 | 127 | 118 |
| 7 | Amoebiasis | 5146 | 120 | 113 |
| 8 | Proteoglycans in cancer | 5205 | 230 | 222 |
| 9 | Cytokine-cytokine receptor interaction | 4060 | 266 | 227 |
| 10 | B cell receptor signaling pathway | 4662 | 78 | 77 |
| 11 | Regulation of actin cytoskeleton | 4810 | 217 | 210 |
| 12 | Aldosterone-regulated sodium reabsorption | 4960 | 40 | 40 |
| 13 | Fc epsilon RI signaling pathway | 4664 | 71 | 70 |
| 14 | MAPK signaling pathway | 4010 | 259 | 253 |
| 15 | HIF-1 signaling pathway | 4066 | 113 | 104 |
| 16 | VEGF signaling pathway | 4370 | 66 | 66 |
| 17 | Leishmaniasis | 5140 | 66 | 66 |
| 18 | Jak-STAT signaling pathway | 4630 | 156 | 136 |
| 19 | Transcriptional misregulation in cancer | 5202 | 181 | 164 |
| 20 | Axon guidance | 4360 | 133 | 133 |
| 21 | Phosphatidylinositol signaling system | 4070 | 81 | 79 |
| 22 | Long-term depression | 4730 | 61 | 59 |
| 23 | Tuberculosis | 5152 | 179 | 170 |
| 24 | Bacterial invasion of epithelial cells | 5100 | 77 | 76 |
| 25 | Salivary secretion | 4970 | 77 | 73 |
| 26 | Pancreatic secretion | 4972 | 103 | 99 |
| 27 | Leukocyte transendothelial migration | 4670 | 121 | 116 |
| 28 | Rheumatoid arthritis | 5323 | 84 | 81 |
| 29 | Viral myocarditis | 5416 | 94 | 74 |
| 30 | Renal cell carcinoma | 5211 | 69 | 68 |
| 31 | Staphylococcus aureus infection | 5150 | 52 | 49 |
| 32 | Glioma | 5214 | 66 | 64 |
| 33 | Hepatitis B | 5161 | 149 | 140 |
| 34 | Small cell lung cancer | 5222 | 86 | 85 |
| 35 | HTLV-I infection | 5166 | 290 | 266 |
| 36 | Salmonella infection | 5132 | 79 | 77 |
| 37 | Amphetamine addiction | 5031 | 70 | 68 |
| 38 | Viral carcinogenesis | 5203 | 236 | 191 |
| 39 | GnRH signaling pathway | 4912 | 89 | 87 |

TABLE 1G

Grem1+ vs Grem1 - Signficant Reactome Pathways

| Rank | Name | ID | pSize | onArray | NDE | tA |
|---|---|---|---|---|---|---|
| 1 | Collagen biosynthesis and modifying enzymes | 5605856 | 52 | 50 | 20 | 1.96 |
| 2 | MPS IIIC - Sanfilippo syndrome C | 5605255 | 110 | 108 | 25 | −0.98 |
| 3 | MPS IV - Morquio syndrome B | 5605261 | 110 | 108 | 25 | −0.96 |
| 4 | MPS VI - Maroteaux-Lamy syndrome | 5605253 | 110 | 108 | 25 | −0.96 |
| 5 | MPS II - Hunter syndrome | 5605257 | 110 | 108 | 25 | −0.95 |
| 6 | Glycosaminoglycan metabolism | 5605249 | 110 | 108 | 25 | −0.96 |
| 7 | MPS IX - Natowicz syndrome | 5605250 | 110 | 108 | 25 | −0.95 |
| 8 | MPS VII - Sly syndrome | 5605256 | 110 | 108 | 25 | −0.94 |
| 9 | MPS I - Hurler syndrome | 5605258 | 110 | 108 | 25 | −0.94 |
| 10 | MPS IIIB - Sanfilippo syndrome B | 5605252 | 110 | 108 | 25 | −0.94 |
| 11 | MPS IIIA - Sanfilippo syndrome A | 5605260 | 110 | 108 | 25 | −0.94 |
| 12 | MPS IIID - Sanfilippo syndrome D | 5605259 | 110 | 108 | 25 | −0.93 |
| 13 | MPS IV - Morquio syndrome A | 5605254 | 110 | 108 | 25 | −0.95 |
| 14 | Fcgamma receptor (FCGR) dependent phagocytosis | 5605170 | 72 | 71 | 17 | −0.53 |
| 15 | Cell surface interactions at the vascular wall | 5605041 | 83 | 81 | 17 | 1.45 |
| 16 | Collagen degradation | 5605823 | 31 | 31 | 10 | 1.47 |
| 17 | Integrin cell surface interactions | 5605038 | 60 | 58 | 14 | 1.00 |
| 18 | Assembly of collagen fibrils and other multimeric structures | 5605828 | 27 | 27 | 9 | −0.91 |
| 19 | Degradation of the extracellular matrix | 5605824 | 94 | 87 | 16 | −1.05 |
| 20 | Signaling by Rho GTPases | 5605351 | 100 | 97 | 15 | 1.77 |
| 21 | GPVI-mediated activation cascade | 5605042 | 26 | 26 | 8 | 0.21 |
| 22 | Response to elevated platelet cytosolic Ca2+ | 5605037 | 86 | 81 | 14 | −0.17 |
| 23 | Syndecan interactions | 5605962 | 18 | 18 | 6 | 0.37 |
| 24 | Elastic fibre formation | 5605850 | 36 | 36 | 7 | −1.32 |
| 25 | Signaling by Hippo | 5605905 | 20 | 20 | 6 | 0.29 |
| 26 | Activation of Matrix Metalloproteinases | 5605848 | 45 | 39 | 8 | 0.93 |
| 27 | Immunoregulatory interactions between a Lymphoid and a non-Lymphoid cell | 5605383 | 51 | 43 | 7 | 1.66 |
| 28 | Regulation of lipid metabolism by Peroxisome proliferator-activated receptor alpha (PPARalpha) | 5605592 | 73 | 73 | 11 | −1.10 |

| NDE | tA | pNDE | pPERT | pG | pG FDR | Status |
|---|---|---|---|---|---|---|
| 26 | 4.91 | 4.E−12 | 0.00 | 1.E−08 | 2.E−06 | Activated |
| 48 | 2.53 | 3.E−08 | 0.02 | 3.E−07 | 2.E−05 | Activated |
| 49 | 2.36 | 6.E−17 | 0.02 | 4.E−07 | 2.E−05 | Activated |
| 27 | 1.53 | 1.E−12 | 0.12 | 2.E−06 | 7.E−05 | Not Applicable |
| 21 | 2.12 | 4.E−06 | 0.04 | 2.E−06 | 7.E−05 | Activated |
| 23 | 0.94 | 7.E−07 | 0.34 | 5.E−06 | 1.E−04 | Not Applicable |

TABLE 1G-continued

Grem1+ vs Grem1 - Signficant Reactome Pathways

| | | | | | | |
|---|---|---|---|---|---|---|
| 25 | 0.65 | 2.E−08 | 0.52 | 8.E−06 | 2.E−04 | Not Applicable |
| 36 | 0.44 | 9.E−08 | 0.66 | 1.E−05 | 2.E−04 | Not Applicable |
| 32 | −1.70 | 1.E−05 | 0.08 | 1.E−05 | 2.E−04 | Not Applicable |
| 18 | 0.13 | 7.E−07 | 0.89 | 1.E−05 | 2.E−04 | Not Applicable |
| 34 | −0.10 | 2.E−07 | 0.92 | 1.E−05 | 2.E−04 | Not Applicable |
| 11 | −0.46 | 2.E−05 | 0.67 | 2.E−04 | 2.E−03 | Not Applicable |
| 14 | 1.00 | 8.E−05 | 0.30 | 3.E−04 | 3.E−03 | Not Applicable |
| 33 | 0.07 | 4.E−05 | 0.94 | 4.E−04 | 4.E−03 | Not Applicable |
| 16 | 1.71 | 6.E−04 | 0.07 | 5.E−04 | 4.E−03 | Not Applicable |
| 13 | −1.06 | 2.E−04 | 0.28 | 5.E−04 | 4.E−03 | Not Applicable |
| 13 | 0.88 | 2.E−04 | 0.36 | 6.E−04 | 5.E−03 | Not Applicable |
| 20 | −0.76 | 2.E−04 | 0.46 | 1.E−03 | 9.E−03 | Not Applicable |
| 22 | −0.47 | 5.E−04 | 0.34 | 2.E−03 | 0.01 | Not Applicable |
| 19 | −0.83 | 5.E−04 | 0.40 | 2.E−03 | 0.01 | Not Applicable |
| 13 | −0.73 | 1.E−03 | 0.30 | 3.E−03 | 0.02 | Not Applicable |
| 9 | 2.11 | 9.E−03 | 0.04 | 3.E−03 | 0.02 | Activated |
| 22 | 0.67 | 8.E−04 | 0.49 | 3.E−03 | 0.02 | Not Applicable |
| 13 | −0.36 | 7.E−04 | 0.72 | 4.E−03 | 0.02 | Not Applicable |
| 12 | −0.68 | 2.E−03 | 0.50 | 6.E−03 | 0.03 | Not Applicable |
| 15 | −0.24 | 1.E−03 | 0.82 | 7.E−03 | 0.04 | Not Applicable |
| 16 | 0.71 | 2.E−03 | 0.46 | 7.E−03 | 0.04 | Not Applicable |
| 11 | 1.53 | 1.E−02 | 0.09 | 7.E−03 | 0.04 | Not Applicable |
| 12 | −0.61 | 2.E−03 | 0.54 | 8.E−03 | 0.04 | Not Applicable |
| 11 | −0.88 | 3.E−03 | 0.39 | 8.E−03 | 0.04 | Not Applicable |
| 8 | −1.43 | 9.E−03 | 0.12 | 9.E−03 | 0.04 | Not Applicable |
| 10 | −1.11 | 5.E−03 | 0.22 | 9.E−03 | 0.04 | Not Applicable |
| 18 | −0.62 | 2.E−03 | 0.53 | 1.E−02 | 0.04 | Not Applicable |
| 12 | 1.19 | 6.E−03 | 0.23 | 1.E−02 | 0.04 | Not Applicable |
| 29 | 0.41 | 2.E−03 | 0.68 | 1.03E−02 | 0.040327256 | Not Applicable |
| 12 | 0.44 | 2.E−03 | 0.65 | 1.20E−02 | 0.045777725 | Not Applicable |
| 11 | 0.49 | 3.E−03 | 0.63 | 1.26E−02 | 0.0467475 | Not Applicable |
| 22 | −0.70 | 3.E−03 | 0.57 | 1.41E−02 | 0.049467655 | Not Applicable |
| 12 | 0.98 | 7.E−03 | 0.29 | 1.41E−02 | 0.049467655 | Not Applicable |

| pNDE | pPERT | pG | pG FDR | Status |
|---|---|---|---|---|
| 0.E+00 | 0.05 | 0.00 | 7.E−05 | Activated |
| 0.E+00 | 0.32 | 0.00 | 7.E−05 | Not Applicable |
| 0.E+00 | 0.33 | 0.00 | 7.E−05 | Not Applicable |
| 0.E+00 | 0.34 | 0.00 | 7.E−05 | Not Applicable |
| 0.E+00 | 0.34 | 0.00 | 7.E−05 | Not Applicable |
| 0.E+00 | 0.35 | 0.00 | 7.E−05 | Not Applicable |
| 0.E+00 | 0.35 | 0.00 | 7.E−05 | Not Applicable |
| 0.E+00 | 0.35 | 0.00 | 7.E−05 | Not Applicable |
| 0.E+00 | 0.35 | 0.00 | 7.E−05 | Not Applicable |
| 0.E+00 | 0.35 | 0.00 | 7.E−05 | Not Applicable |
| 0.E+00 | 0.35 | 0.00 | 7.E−05 | Not Applicable |
| 0.E+00 | 0.37 | 0.00 | 7.E−05 | Not Applicable |
| 1.E−06 | 0.61 | 0.00 | 1.E−04 | Not Applicable |
| 7.E−06 | 0.13 | 0.00 | 1.E−04 | Not Applicable |
| 1.E−05 | 0.13 | 0.00 | 2.E−04 | Not Applicable |
| 8.E−06 | 0.34 | 0.00 | 3.E−04 | Not Applicable |
| 2.E−05 | 0.56 | 0.00 | 1.E−03 | Not Applicable |
| 7.E−05 | 0.28 | 0.00 | 2.E−03 | Not Applicable |
| 8.E−04 | 0.06 | 0.00 | 4.E−03 | Not Applicable |
| 1.E−04 | 0.83 | 0.00 | 0.01 | Not Applicable |
| 4.E−04 | 0.93 | 0.00 | 0.02 | Not Applicable |
| 5.E−04 | 0.74 | 0.00 | 0.02 | Not Applicable |
| 6.E−03 | 0.12 | 0.01 | 0.03 | Not Applicable |
| 1.E−03 | 0.80 | 0.01 | 0.04 | Not Applicable |
| 2.E−03 | 0.36 | 0.01 | 0.04 | Not Applicable |
| 1.E−02 | 0.07 | 0.01 | 0.04 | Not Applicable |
| 5.E−03 | 0.23 | 0.01 | 0.04 | Not Applicable |

TABLE 1H

ECM-Receptor Interaction Genes in Grem1+ Vs Grem1− (fdr < 0.05)

| Symbol | Description | Log$_2$ FC |
|---|---|---|
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |

TABLE 1H-continued

ECM-Receptor Interaction Genes in Grem1+ Vs Grem1− (fdr < 0.05)

| Symbol | Description | Log₂ FC |
|---|---|---|
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |
| Dag1 | dystroglycan 1 | 2.35 |
| Hspg2 | perlecan (heparan sulfate proteoglycan 2) | 2.60 |
| Ibsp | integrin binding sialoprotein | 3.26 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Lama4 | laminin, alpha 4 | 1.80 |
| Lamb2 | laminin, beta 2 | 2.50 |
| Npnt | nephronectin | 3.91 |
| Sdc1 | syndecan 1 | 2.76 |
| Sdc4 | syndecan 4 | 4.91 |
| Thbs3 | thrombospondin 3 | 4.57 |

Table 1I: PI3K-Akt Signaling Genes in Grem1+ Vs Grem1− (fdr < 0.05)

| Symbol | Description | Log₂ FC |
|---|---|---|
| Ccnd1 | cyclin D1 | 4.35 |
| Ccnd3 | cyclin D3 | −2.04 |
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |
| Creb3l2 | cAMP responsive element binding protein 3-like 2 | 4.85 |
| Csf1r | colony stimulating factor 1 receptor | −1.73 |
| Fgf2 | fibroblast growth factor 2 | 5.70 |
| Fgfr1 | fibroblast growth factor receptor 1 | 2.60 |
| Fgfr2 | fibroblast growth factor receptor 2 | 5.65 |
| Fgfr3 | fibroblast growth factor receptor 3 | 3.86 |
| Ibsp | integrin binding sialoprotein | 3.26 |
| Igf1 | insulin-like growth factor 1 | 4.11 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Lama4 | laminin, alpha 4 | 1.80 |
| Lamb2 | laminin, beta 2 | 2.50 |
| Lpar1 | lysophosphatidic acid receptor 1 | 3.03 |
| Lpar4 | lysophosphatidic acid receptor 4 | 4.46 |
| Lpar6 | lysophosphatidic acid receptor 6 | −3.83 |
| Mapk1 | mitogen-activated protein kinase 1 | −3.32 |
| Myb | myeloblastosis oncogene | −5.06 |
| Ngf | nerve growth factor | 5.93 |
| Osmr | oncostatin M receptor | 5.40 |
| Pdgfa | platelet derived growth factor, alpha | 1.50 |
| Pik3cd | phosphatidylinositol 3-kinase catalytic delta polypeptide | −2.58 |
| Pten | phosphatase and tensin homolog | −3.97 |
| Ptk2 | PTK2 protein tyrosine kinase 2 | 2.83 |
| Rheb | Ras homolog enriched in brain | 1.33 |
| Sgk1 | serum/glucocorticoid regulated kinase 1 | 2.45 |
| Sos2 | son of sevenless homolog 2 (Drosophila) | −2.70 |
| Syk | spleen tyrosine kinase | −4.15 |
| Thbs3 | thrombospondin 3 | 4.57 |
| Tlr4 | toll-like receptor 4 | −2.88 |
| Vegfa | vascular endothelial growth factor A | 1.87 |
| Ywhaq | tyrosine 3-monooxygenase/tryptophan 5-monooxygenase activation protein, theta polypeptide | 1.77 |

TABLE 1J

Focal Adhesion Genes in Grem1+ Vs Grem1− (fdr < 0.05)

| Symbol | Description | Log₂ FC |
|---|---|---|
| Actn4 | actinin alpha 4 | 1.47 |
| Capn2 | calpain 2 | 3.45 |
| Cav1 | caveolin 1, caveolae protein | 3.07 |
| Cav2 | caveolin 2 | 3.08 |
| Ccnd1 | cyclin D1 | 4.35 |
| Ccnd3 | cyclin D3 | −2.04 |
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |
| Flnb | filamin, beta | 2.89 |
| Flnc | filamin C, gamma | 3.35 |
| Ibsp | integrin binding sialoprotein | 3.26 |
| Igf1 | insulin-like growth factor 1 | 4.11 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Jun | jun proto-oncogene | 1.98 |
| Lama4 | laminin, alpha 4 | 1.80 |
| Lamb2 | laminin, beta 2 | 2.50 |
| Mapk1 | mitogen-activated protein kinase 1 | −3.32 |
| Mylk | myosin, light polypeptide kinase | 2.14 |
| Pak3 | p21 protein (Cdc42/Rac)-activated kinase 3 | 5.49 |
| Parvg | parvin, gamma | −3.07 |
| Pdgfa | platelet derived growth factor, alpha | 1.50 |
| Pik3cd | phosphatidylinositol 3-kinase catalytic delta polypeptide | −2.58 |
| Prkcb | protein kinase C, beta | −3.85 |
| Prkcg | protein kinase C, gamma | 2.75 |
| Pten | phosphatase and tensin homolog | −3.97 |
| Ptk2 | PTK2 protein tyrosine kinase 2 | 2.83 |
| Rac2 | RAS-related C3 botulinum substrate 2 | −3.03 |
| Sos2 | son of sevenless homolog 2 (Drosophila) | −2.70 |
| Thbs3 | thrombospondin 3 | 4.57 |
| Vasp | vasodilator-stimulated phosphoprotein | −1.39 |
| Vav1 | vav 1 oncogene | −4.46 |
| Vav2 | vav 2 oncogene | 2.38 |
| Vav3 | vav 3 oncogene | −2.01 |
| Vegfa | vascular endothelial growth factor A | 1.87 |
| Xiap | X-linked inhibitor of apoptosis | −2.45 |

TABLE 1K

| Osteoblast differentiation GO:0001649 | | | | |
|---|---|---|---|---|
| Symbol | probeid | logFC | P. Value | fdr |
| Shox2 | 1438042_at | 7.139693094 | 1.12E−05 | 0.024717328 |
| Fgfr2 | 1433489_s_at | 5.652317879 | 1.51E−05 | 0.024717328 |
| Bmp2 | 1423635_at | 5.787265063 | 5.84E−05 | 0.024717328 |
| Col9a1 | 1421381_a_at | 5.143849185 | 7.20E−05 | 0.024717328 |
| Sox9 | 1424950_at | 6.90133905 | 0.000110199 | 0.024717328 |
| Comp | 1419527_at | 3.999527882 | 0.00013709 | 0.025235259 |
| Papss2 | 1421987_at | 5.85768973 | 0.000137253 | 0.025235259 |
| Col10a1 | 1422253_at | 4.649700769 | 0.000150964 | 0.025235259 |
| Matn1 | 1418477_at | 5.63933284 | 0.000191855 | 0.026424026 |
| Impad1 | 1437290_at | 4.000095671 | 0.000198075 | 0.02656323 |
| Ltbp3 | 1437833_at | 2.966172299 | 0.000217433 | 0.027040111 |
| Sp7 | 1418425_at | 3.103511735 | 0.000261664 | 0.028624838 |
| Ddr2 | 1422738_at | 3.897227684 | 0.000269907 | 0.028738428 |
| Ankrd11 | 1458452_at | −1.749643873 | 0.000427813 | 0.03083902 |
| Bmp6 | 1450759_at | 2.177660599 | 0.000527626 | 0.032374884 |
| Thbs3 | 1416623_at | 4.56764372 | 0.000569659 | 0.033236981 |
| Ptprc | 1440165_at | −5.673465126 | 0.000645357 | 0.03437141 |
| Igf1 | 1419519_at | 4.105829219 | 0.000766857 | 0.03552034 |
| Mef2c | 1451506_at | 1.562297202 | 0.000772609 | 0.03552034 |
| Gli3 | 1456067_at | 2.454729863 | 0.000813139 | 0.036059697 |
| Insig1 | 1454671_at | 2.083603859 | 0.000857009 | 0.036461333 |
| Csgalnact1 | 1452365_at | 6.102113169 | 0.000870032 | 0.036461333 |
| Asxl2 | 1460597_at | −2.69793666 | 0.000925415 | 0.036876699 |
| Hspg2 | 1418670_s_at | 2.601492005 | 0.000988966 | 0.037703609 |
| Dlx5 | 1449863_a_at | 3.758824499 | 0.001062068 | 0.039185564 |
| Sparc | 1416589_at | 1.604128392 | 0.001134471 | 0.040211493 |
| Slc38a10 | 1427295_at | 1.836342464 | 0.001251799 | 0.041425472 |
| Has2 | 1449169_at | 4.992358344 | 0.001262338 | 0.041642764 |
| FgfrS3 | 1421841_at | 3.862610571 | 0.001486791 | 0.044252631 |
| Npr2 | 1427191_at | 3.46860457 | 0.00168539 | 0.046605008 |
| Sulf2 | 1442408_at | 1.6036124 | 0.001818939 | 0.048072123 |
| Serpinh1 | 1450843_a_at | 1.296545474 | 0.00188638 | 0.048519059 |
| Sema4d | 1420824_at | −1.802904281 | 0.001947949 | 0.04888768 |
| Phospho2 | 1425190_a_at | −2.814035598 | 0.001978658 | 0.049100382 |
| Alpl | 1423611_at | 2.963453942 | 0.003152191 | 0.059797918 |
| Cadm1 | 1417376_a_at | 4.105907278 | 0.003749737 | 0.06413052 |
| Smad1 | 1448208_at | 3.171019581 | 0.003939544 | 0.065217381 |
| Fat4 | 1459749_s_at | 3.238993925 | 0.004025324 | 0.065970771 |
| Runx2 | 1424704_at | 2.887812904 | 0.005507695 | 0.0751405 |
| Rarg | 1419415_a_at | 1.550286712 | 0.005801297 | 0.076976842 |
| Insig2 | 1417980_a_at | 2.44324681 | 0.005844576 | 0.077271793 |
| Sik3 | 1460439_at | −1.085764805 | 0.007557193 | 0.087776707 |
| Cyp26b1 | 1460011_at | 2.414945578 | 0.007803403 | 0.089217497 |
| Glg1 | 1460554_s_at | 1.08231524 | 0.009548025 | 0.098119909 |
| Pex7 | 1418988_at | −1.511451194 | 0.010079617 | 0.101400796 |
| Gnas | 1450186_s_at | 1.15793611 | 0.01017669 | 0.101946203 |
| Smad5 | 1433641_at | 1.326053173 | 0.011763418 | 0.109476522 |
| Ostc | 1449139_at | 1.477735339 | 0.013125314 | 0.116439497 |
| Plxnb1 | 1435254_at | 2.942409912 | 0.013429212 | 0.117743176 |
| Bbx | 1425835_a_at | 2.446951157 | 0.014483662 | 0.122648828 |
| Twist1 | 1418733_at | 1.382611779 | 0.015769561 | 0.1278689 |
| Nab1 | 1438819_at | −2.921685423 | 0.01616797 | 0.129413797 |
| Asxl1 | 1458380_at | −1.336329518 | 0.020033869 | 0.144567603 |
| Osr2 | 1426155_a_at | 0.502214387 | 0.024820681 | 0.160932229 |
| Setdb1 | 1451833_a_at | −0.705544003 | 0.026029982 | 0.164930909 |
| Pthlh | 1422324_a_at | 2.22023888 | 0.027653676 | 0.170616752 |
| Ift80 | 1427568_a_at | 2.136527636 | 0.035499982 | 0.194259243 |
| Col2a1 | 1450567_a_at | 0.516328675 | 0.036987644 | 0.198758455 |
| Cited2 | 1452207_at | 0.777201054 | 0.038182 | 0.202260558 |
| Pax1 | 1449359_at | 3.129371792 | 0.039117548 | 0.205001226 |
| Ski | 1426373_at | 1.208235773 | 0.039744837 | 0.206769456 |
| Rhoa | 1437628_s_at | −0.461425196 | 0.044691344 | 0.220310888 |
| Bnc2 | 1438861_at | 4.234307253 | 0.048503083 | 0.23058618 |
| Whsc1 | 1435136_at | −1.003323897 | 0.060212775 | 0.258609312 |
| Inppl1 | 1460394_a_at | 0.567599274 | 0.068322178 | 0.276571991 |
| Mcph1 | 1439115_at | −1.231750154 | 0.074267025 | 0.289484996 |
| Fgf18 | 1449545_at | 1.956305626 | 0.080130689 | 0.300802975 |
| Hoxa11 | 1420414_at | 0.511171629 | 0.134279 | 0.394218529 |
| Ctc1 | 1423656_x_at | −0.345446644 | 0.137792974 | 0.400270575 |
| Sh3pxd2b | 1442919_at | 0.783611603 | 0.137852296 | 0.40031788 |
| Evc | 1448876_at | 1.720368653 | 0.140736918 | 0.404315813 |
| Lrp6 | 1451022_at | 1.847234643 | 0.145204659 | 0.410548216 |
| Grem1 | 1425357_a_at | 2.037426007 | 0.154104522 | 0.422971522 |
| Amer1 | 1439565_at | −1.2063171 | 0.160046885 | 0.430901053 |
| Scx | 1456291_x_at | 0.275344353 | 0.169500763 | 0.442948625 |
| Ptger4 | 1424208_at | −0.972916857 | 0.178471738 | 0.455326048 |

TABLE 1K-continued

Osteoblast differentiation GO:0001649

| Symbol | probeid | logFC | P. Value | fdr |
|---|---|---|---|---|
| Ryr1 | 1427306_at | −0.295073248 | 0.191481139 | 0.471358493 |
| Rab23 | 1454876_at | 0.859713003 | 0.194017485 | 0.474398912 |
| Trim45 | 1441412_s_at | 0.203427908 | 0.202761269 | 0.484027734 |
| Axin2 | 1436845_at | 0.387992131 | 0.211247475 | 0.49331913 |
| Lrrc17 | 1429679_at | 0.233010363 | 0.235628038 | 0.520602564 |
| Pitx2 | 1424797_a_at | 1.070819666 | 0.236282353 | 0.521384139 |
| Carm1 | 1419743_s_at | 0.647225506 | 0.253119301 | 0.539097732 |
| Dym | 1423736_a_at | −0.915006359 | 0.271266186 | 0.55550201 |
| Sulf1 | 1436319_at | 1.195688044 | 0.274329539 | 0.558100796 |
| Smad9 | 1450265_at | 0.162215826 | 0.278961897 | 0.562412139 |
| Prpsap2 | 1452062_at | −0.314973589 | 0.28405301 | 0.566962065 |
| Msx2 | 1438351_at | 0.352902478 | 0.299225831 | 0.581271523 |
| Mef2d | 1421388_at | −0.186624593 | 0.317508841 | 0.598850338 |
| Nppc | 1422790_at | 0.160740904 | 0.318516161 | 0.599649792 |
| Fam73b | 1454621_s_at | 0.299423097 | 0.321171428 | 0.601935055 |
| Acp5 | 1431609_a_at | −0.930966065 | 0.331118878 | 0.610044038 |
| Fgf4 | 1420086_x_at | 0.182639322 | 0.356485355 | 0.632486284 |
| Cbs | 1423844_s_at | 0.200634176 | 0.366165065 | 0.640416125 |
| Wnt1 | 1425377_at | 0.369757817 | 0.379671843 | 0.650544352 |
| T | 1419304_at | 0.16388178 | 0.390584684 | 0.659124441 |
| Col1a1 | 1423669_at | −0.621264052 | 0.406590229 | 0.671883603 |
| Hoxb4 | 1451761_at | −0.127266076 | 0.462604836 | 0.716107186 |
| Sp5 | 1422914_at | −0.117409597 | 0.495346498 | 0.738630642 |
| Hoxd11 | 1450584_at | 0.09335222 | 0.516782714 | 0.752676029 |
| Bmp4 | 1422912_at | −0.151574562 | 0.528444464 | 0.760720517 |
| Fgf8 | 1451882_a_at | 0.082771762 | 0.563508165 | 0.784527913 |
| Rarb | 1454906_at | 0.132469624 | 0.580742851 | 0.795459147 |
| Msx1 | 1417127_at | −0.07927679 | 0.6088118 | 0.812199278 |
| Por | 1416933_at | −0.080981309 | 0.640208478 | 0.830405871 |
| Thbs1 | 1460302_at | −0.09408991 | 0.640329897 | 0.830419322 |
| Rara | 1450180_a_at | −0.145032547 | 0.656889118 | 0.839241871 |
| Lrp5 | 1449299_at | 0.120069936 | 0.667173815 | 0.845349241 |
| Tfap2a | 1421996_at | 0.048827656 | 0.730112475 | 0.878838306 |
| Lep | 1422582_at | −0.05140898 | 0.743335178 | 0.886299367 |
| Spns2 | 1451601_a_at | −0.093090513 | 0.750770457 | 0.890055922 |
| Nab2 | 1417930_at | −0.141428281 | 0.763601435 | 0.897204332 |
| Sfrp2 | 1448201_at | 0.267663483 | 0.765342683 | 0.898105369 |
| Dchs1 | 1429163_at | 0.034058005 | 0.851902726 | 0.938492662 |
| Sbds | 1426480_at | −0.065123897 | 0.882072035 | 0.950943967 |
| Bglap2 | 1449880_s_at | 0.030899771 | 0.961461518 | 0.983599805 |
| Cdx1 | 1449582_at | −0.001241112 | 0.992657152 | 0.997194845 |
| Frem1 | 1455280_at | 0.0010303 | 0.993945229 | 0.997823631 |

TABLE 1L

Chondrocyte differentiation GO:0002062

| Symbol | probeid | logFC | P. Value | globalfdr |
|---|---|---|---|---|
| Sox5 | 1452511_at | 7.227671317 | 7.96E−06 | 0.02471733 |
| Frzb | 1416658_at | 6.487492378 | 8.83E−06 | 0.02471733 |
| Shox2 | 1438042_at | 7.139693094 | 1.12E−05 | 0.02471733 |
| Trps1 | 1438214_at | 3.407552042 | 4.76E−05 | 0.02471733 |
| Cytl1 | 1456793_at | 6.874597272 | 5.09E−05 | 0.02471733 |
| Bmp2 | 1423635_at | 5.787265063 | 5.84E−05 | 0.02471733 |
| Col11a2 | 1423578_at | 4.142066889 | 6.46E−05 | 0.02471733 |
| Pkdcc | 1454838_s_at | 7.289629759 | 6.74E−05 | 0.02471733 |
| Col9a1 | 1421381_a_at | 5.143849185 | 7.20E−05 | 0.02471733 |
| Sox9 | 1424950_at | 6.90133905 | 0.000110199 | 0.02471733 |
| Tgfb2 | 1423250_a_at | 5.546499385 | 0.000122435 | 0.02520744 |
| Comp | 1419527_at | 3.999527882 | 0.00013709 | 0.02523526 |
| Col10a1 | 1422253_at | 4.649700769 | 0.000150964 | 0.02523526 |
| Matn1 | 1418477_at | 5.63933284 | 0.000191855 | 0.02642403 |
| Impad1 | 1437290_at | 4.000095671 | 0.000198075 | 0.02656323 |
| Sox6 | 1447655_x_at | 3.042240366 | 0.00020449 | 0.0267325 |
| Ltbp3 | 1437833_at | 2.966172299 | 0.000217433 | 0.02704011 |
| Nfib | 1434101_at | 2.200370996 | 0.000300679 | 0.02873843 |
| Chst11 | 1450509_at | 4.028847262 | 0.000322352 | 0.02907679 |
| Creb3l2 | 1452381_at | 4.852931274 | 0.00046023 | 0.03115804 |
| Bmp6 | 1450759_at | 2.177660599 | 0.000527626 | 0.03237488 |
| Col11a1 | 1418599_at | 2.341265056 | 0.000531438 | 0.03247748 |
| Thbs3 | 1416623_at | 4.56764372 | 0.000569659 | 0.03323698 |
| Mmp13 | 1417256_at | 4.244523746 | 0.000617022 | 0.03397116 |

TABLE 1L-continued

| Chondrocyte differentiation GO:0002062 | | | | |
|---|---|---|---|---|
| Symbol | probeid | logFC | P. Value | globalfdr |
| Cyr61 | 1438133_a_at | 5.691198456 | 0.00063681 | 0.03419138 |
| Mia3 | 1459984_at | 2.370589971 | 0.000658158 | 0.03447572 |
| Hif1a | 1448183_a_at | 1.72827087 | 0.000744244 | 0.03532241 |
| Bmp5 | 1455851_at | 4.361119404 | 0.000754542 | 0.03535411 |
| Mef2c | 1451506_at | 1.562297202 | 0.000772609 | 0.03552034 |
| Fgf2 | 1449826_a_at | 5.704557594 | 0.000783732 | 0.03566748 |
| Gli3 | 1456067_at | 2.454729863 | 0.000813139 | 0.0360597 |
| Pth1r | 1417092_at | 5.144468665 | 0.000813154 | 0.0360597 |
| Acan | 1449827_at | 3.418337262 | 0.000822404 | 0.03611613 |
| Fgfr1 | 1424050_s_at | 2.601293712 | 0.000865071 | 0.03646133 |
| Csgalnact1 | 1452365_at | 6.102113169 | 0.000870032 | 0.03646133 |
| Hspg2 | 1418670_s_at | 2.601492005 | 0.000988966 | 0.03770361 |
| Mgp | 1448416_at | 3.350708397 | 0.001161888 | 0.0404339 |
| Snai2 | 1418673_at | 5.037011523 | 0.001285815 | 0.04171829 |
| Fgfr3 | 1421841_at | 3.862610571 | 0.001486791 | 0.04425268 |
| Maf | 1437473_at | 3.769803046 | 0.001536869 | 0.04489271 |
| Ctgf | 1416953_at | 2.49942916 | 0.001724906 | 0.04701858 |
| Sulf2 | 1442408_at | 1.6036124 | 0.001818939 | 0.04807212 |
| Serpinh1 | 1450843_a_at | 1.296545474 | 0.00188638 | 0.04851906 |
| Thra | 1443952_at | 1.825949647 | 0.00237175 | 0.05300708 |
| Zbtb16 | 1419874_x_at | 3.803773056 | 0.002398106 | 0.05325226 |
| Bmp8a | 1449873_at | 2.201924918 | 0.003848633 | 0.06493723 |
| Smad1 | 1448208_at | 3.171019581 | 0.003939544 | 0.06521738 |
| Pkd1 | 1460210_at | 2.908566799 | 0.00405261 | 0.06613797 |
| Bmp7 | 1418910_at | 1.926967359 | 0.004189368 | 0.06714193 |
| Mex3c | 1444701_at | 2.842755288 | 0.004395625 | 0.06871649 |
| Bmpr1a | 1425492_at | 1.362007729 | 0.005169266 | 0.07349907 |
| Runx2 | 1424704_at | 2.887812904 | 0.005507695 | 0.0751405 |
| Rarg | 1419415_a_at | 1.550286712 | 0.005801297 | 0.07697684 |
| Barx2 | 1421761_a_at | 0.856240972 | 0.006409754 | 0.08068276 |
| Tgfb1 | 1445360_at | −1.853388092 | 0.006592491 | 0.08152761 |
| Lect1 | 1460258_at | 4.589863169 | 0.006972883 | 0.08388477 |
| Ctnnb1 | 1450008_a_at | 1.662619268 | 0.007200751 | 0.08544095 |
| Tgfbr2 | 1426397_at | 1.866595465 | 0.007508601 | 0.08755963 |
| Sik3 | 1460439_at | −1.085764805 | 0.007557193 | 0.08777671 |
| Hoxc4 | 1422870_at | 1.197960754 | 0.007610561 | 0.08803383 |
| Otor | 1425083_at | 4.223579518 | 0.008769642 | 0.09435106 |
| Ror2 | 1457128_at | 4.339094191 | 0.008963 | 0.09531397 |
| Glg1 | 1460554_s_at | 1.08231524 | 0.009548025 | 0.09811991 |
| Tgfbr1 | 1420893_a_at | −1.55359297 | 0.009766074 | 0.09956142 |
| Gnas | 1450186_s_at | 1.15793611 | 0.01017669 | 0.1019462 |
| Smad5 | 1433641_at | 1.326053173 | 0.011763418 | 0.10947625 |
| Prkca | 1427562_a_at | 2.106132835 | 0.013587175 | 0.11834592 |
| Hes5 | 1456010_x_at | −2.12314448 | 0.016556928 | 0.13093705 |
| Gli2 | 1459211_at | 1.040592945 | 0.017675299 | 0.13518291 |
| Mapk14 | 1426104_at | −1.553226091 | 0.020975461 | 0.14796945 |
| Lnp | 1453035_at | −2.975528114 | 0.023920912 | 0.15807429 |
| Osr2 | 1426155_a_at | 0.502214387 | 0.024820681 | 0.16093223 |
| Hmga2 | 1450781_at | 1.095868613 | 0.02694941 | 0.16831614 |
| Pthlh | 1422324_a_at | 2.22023888 | 0.027653676 | 0.17061675 |
| Wnt9a | 1436978_at | 0.87174088 | 0.027858165 | 0.17122255 |
| Bmpr1b | 1437312_at | 1.259734785 | 0.028010413 | 0.17173704 |
| Prrx1 | 1432129_a_at | 1.477735949 | 0.028062403 | 0.17191557 |
| Foxd1 | 1418876_at | 4.467305245 | 0.030439858 | 0.17907112 |
| Ift80 | 1427568_a_at | 2.136527636 | 0.035499982 | 0.19425924 |
| Col2a1 | 1450567_a_at | 0.516328675 | 0.036987644 | 0.19875846 |
| Thrb | 1422202_at | 2.480665058 | 0.043633913 | 0.21759789 |
| Atp7a | 1418774_a_at | −1.673902233 | 0.044739406 | 0.22045143 |
| Mapk3 | 1427060_at | −0.665697033 | 0.049130252 | 0.23233967 |
| Wnt5a | 1448818_at | 2.932630314 | 0.049273596 | 0.23264251 |
| Bmp1 | 1427457_a_at | 2.430286862 | 0.051273483 | 0.23736193 |
| Rela | 1419536_a_at | 1.047678744 | 0.057679732 | 0.25345212 |
| Hoxa5 | 1443803_x_at | 1.027593295 | 0.061492348 | 0.26170129 |
| Esrra | 1442864_at | −0.644689343 | 0.067250466 | 0.27435072 |
| Fgf18 | 1449545_at | 1.956305626 | 0.080130689 | 0.30080298 |
| Hoxa3 | 1427433_s_at | 0.507084998 | 0.08120338 | 0.30287153 |
| Zbtb7a | 1437255_at | −0.366464305 | 0.09699201 | 0.33330316 |
| Runx3 | 1440275_at | 0.967803284 | 0.097930192 | 0.33494632 |
| Hoxb3 | 1427605_at | 0.394183877 | 0.099739178 | 0.33804288 |
| Edn1 | 1451924_a_at | −0.298299622 | 0.101953846 | 0.34187512 |
| Eif2ak3 | 1430371_x_at | −1.422549648 | 0.119792665 | 0.37163913 |
| Satb2 | 1425904_at | 0.486466036 | 0.128215418 | 0.38470549 |
| Bbs1 | 1437310_at | 1.90386954 | 0.128294835 | 0.38470549 |
| Hoxa11 | 1420414_at | 0.511171629 | 0.134279 | 0.39421853 |
| Bmp8b | 1440706_at | 0.263087681 | 0.135557361 | 0.39655082 |
| Foxd2 | 1442315_at | 0.463202134 | 0.143844177 | 0.40876544 |

TABLE 1L-continued

Chondrocyte differentiation GO:0002062

| Symbol | probeid | logFC | P. Value | globalfdr |
| --- | --- | --- | --- | --- |
| Lrp6 | 1451022_at | 1.847234643 | 0.145204659 | 0.41054822 |
| Zeb1 | 1418926_at | 1.163547486 | 0.146603252 | 0.41268652 |
| Fgf9 | 1438718_at | −0.396660104 | 0.159287355 | 0.42979473 |
| Scx | 1456291_x_at | 0.275344353 | 0.169500763 | 0.44294863 |
| Wnt7a | 1458334_at | 0.230585657 | 0.178295657 | 0.45510852 |
| Mkks | 1422627_a_at | 0.629498974 | 0.204234917 | 0.48574462 |
| Bbs2 | 1424478_at | 1.188472075 | 0.204515227 | 0.48587449 |
| Axin2 | 1436845_at | 0.387992131 | 0.211247475 | 0.49331913 |
| Arid5a | 1451340_at | −0.312811068 | 0.211944957 | 0.49438477 |
| Hand1 | 1417525_at | 0.201272013 | 0.240887009 | 0.52659659 |
| Carm1 | 1419743_s_at | 0.647225506 | 0.253119301 | 0.53909773 |
| Sulf1 | 1436319_at | 1.195688044 | 0.274329539 | 0.5581008 |
| Smad9 | 1450265_at | 0.162215826 | 0.278961897 | 0.56241214 |
| Mycn | 1417155_at | 0.397691657 | 0.289395697 | 0.57218164 |
| Pitx1 | 1419514_at | 0.170296898 | 0.291463694 | 0.57395417 |
| Msx2 | 1438351_at | 0.352902478 | 0.299225831 | 0.58127152 |
| Prrx2 | 1432331_a_at | 0.731912166 | 0.300918486 | 0.58270253 |
| Wnt7b | 1420892_at | 0.157152661 | 0.314547758 | 0.59632366 |
| Mef2d | 1421388_at | −0.186624593 | 0.317508841 | 0.59885034 |
| Nppc | 1422790_at | 0.160740904 | 0.318516161 | 0.59964979 |
| Chrdl2 | 1420539_a_at | 0.203324878 | 0.341475431 | 0.61922033 |
| Uncx | 1419633_at | 0.148759176 | 0.353940851 | 0.62995605 |
| Fgf4 | 1420086_x_at | 0.182639322 | 0.356485355 | 0.63248628 |
| Cbs | 1423844_s_at | 0.200634176 | 0.366165065 | 0.64041613 |
| Cst10 | 1449447_at | 0.197121868 | 0.368427113 | 0.6420478 |
| Gdf5 | 1419139_at | 0.129088056 | 0.371305218 | 0.6441108 |
| Foxd4 | 1422318_at | −0.134476132 | 0.379737298 | 0.65058051 |
| Foxd3 | 1422210_at | 0.122987443 | 0.399274562 | 0.66574299 |
| Col1a1 | 1423669_at | −0.621264052 | 0.406590229 | 0.6718836 |
| Fgf6 | 1427582_at | 0.133060268 | 0.435640805 | 0.69508034 |
| Nog | 1422300_at | 0.153211198 | 0.443767114 | 0.70129789 |
| Smad3 | 1450472_s_at | 0.284666876 | 0.448289325 | 0.70498612 |
| Fbxw4 | 1417226_at | 0.154450778 | 0.489472582 | 0.73441242 |
| Six2 | 1427436_at | 0.117987176 | 0.493264422 | 0.73685768 |
| Dlx2 | 1448877_at | 0.179930447 | 0.501440307 | 0.74322059 |
| Hoxd11 | 1450584_at | 0.09335222 | 0.516782714 | 0.75267603 |
| Bmp4 | 1422912_at | −0.151574562 | 0.528444464 | 0.76072052 |
| Rarb | 1454906_at | 0.132469624 | 0.580742851 | 0.79545915 |
| Msx1 | 1417127_at | −0.07927679 | 0.6088118 | 0.81219928 |
| Pax7 | 1452510_at | −0.072603424 | 0.615871162 | 0.81680712 |
| Por | 1416933_at | −0.080981309 | 0.640208478 | 0.83040587 |
| Thbs1 | 1460302_at | −0.09408991 | 0.640329897 | 0.83041932 |
| Rara | 1450180_a_at | −0.145032547 | 0.656889118 | 0.83924187 |
| Osr1 | 1449350_at | 0.066742628 | 0.657967365 | 0.83979472 |
| Nkx3-2 | 1421464_at | 0.072593918 | 0.659884707 | 0.84131336 |
| Snai1 | 1448742_at | 0.051585999 | 0.712278255 | 0.86945623 |
| Hand2 | 1436041_at | 0.051832079 | 0.719149452 | 0.87278294 |
| Lep | 1422582_at | −0.05140898 | 0.743335178 | 0.88629937 |
| Sfrp2 | 1448201_at | 0.267663483 | 0.765342683 | 0.89810537 |
| Myf5 | 1420757_at | 0.036879133 | 0.798434878 | 0.91361693 |
| Ihh | 1450704_at | 0.030673687 | 0.821630534 | 0.9243161 |
| Efemp1 | 1427183_at | 0.226301546 | 0.846451572 | 0.93572931 |
| Hoxd3 | 1421537_at | −0.019430098 | 0.903327872 | 0.96012428 |
| Rspo2 | 1455893_at | −0.022960144 | 0.960848418 | 0.9833494 |

TABLE 1M

Adipocyte Differentiation GO:0045444

| Symbol | probeid | logFC | P. Value | fdr |
| --- | --- | --- | --- | --- |
| Frzb | 1416658_at | 6.487492378 | 8.83E−06 | 0.024717328 |
| Scd1 | 1415965_at | 6.929461289 | 2.02E−05 | 0.024717328 |
| Wif1 | 1425425_a_at | 5.61016474 | 2.97E−05 | 0.024717328 |
| Wwtr1 | 1417818_at | 4.269668342 | 4.04E−05 | 0.024717328 |
| Bmp2 | 1423635_at | 5.787265063 | 5.84E−05 | 0.024717328 |
| Medag | 1452244_at | 2.545095371 | 0.00012336 | 0.025207442 |
| Fndc3b | 1433833_at | 4.141051542 | 0.00016123 | 0.025235259 |
| Id2 | 1435176_a_at | 2.559804641 | 0.000172645 | 0.025235259 |
| Enpp1 | 1419276_at | 4.181038806 | 0.000180395 | 0.025504996 |
| Ccnd1 | 1448698_at | 4.352370653 | 0.000619696 | 0.033971157 |
| Selenbp1 | 1450699_at | −2.072635347 | 0.000691838 | 0.034716762 |
| Plcb1 | 1435043_at | 4.482106245 | 0.000692032 | 0.034716762 |

TABLE 1M-continued

Adipocyte Differentiation GO:0045444

| Symbol | probeid | logFC | P. Value | fdr |
|---|---|---|---|---|
| Igf1 | 1419519_at | 4.105829219 | 0.000766857 | 0.03552034 |
| 4932438A13Rik | 1444660_at | -1.721706348 | 0.000835528 | 0.036271815 |
| Insig1 | 1454671_at | 2.083603859 | 0.000857009 | 0.036461333 |
| Asxl2 | 1460597_at | -2.69793666 | 0.000925415 | 0.036876699 |
| Itga6 | 1422445_at | 2.165019349 | 0.000951619 | 0.037127119 |
| Ero1l | 1449324_at | -5.241542349 | 0.001097216 | 0.039747422 |
| Klf4 | 1417394_at | 2.491431313 | 0.00117445 | 0.040597548 |
| Snai2 | 1418673_at | 5.037011523 | 0.001285815 | 0.041718287 |
| Lama4 | 1424807_at | 1.798716009 | 0.001447975 | 0.043819119 |
| Plac8 | 1451335_at | -3.934376347 | 0.001976289 | 0.049100382 |
| Zbtb16 | 1419874_x_at | 3.803773056 | 0.002398106 | 0.053252258 |
| Rgs2 | 1419248_at | -2.06216508 | 0.003091707 | 0.059308851 |
| Id4 | 1423259_at | 3.91112981 | 0.003232534 | 0.060264862 |
| Egr2 | 1427683_at | 2.262049947 | 0.003343364 | 0.061201783 |
| Gpx1 | 1460671_at | -1.501819908 | 0.004191145 | 0.067141932 |
| 1100001G20Rik | 1434484_at | -2.836197894 | 0.004262215 | 0.067829984 |
| Zfpm2 | 1449314_at | 2.053382872 | 0.004319297 | 0.068075477 |
| Mex3c | 1444701_at | 2.842755288 | 0.004395625 | 0.068716491 |
| Lamb3 | 1417812_a_at | 1.656879301 | 0.004815257 | 0.071439951 |
| Osbpl8 | 1437069_at | -1.029145389 | 0.005234847 | 0.073806387 |
| Tcf7l2 | 1429428_at | 2.819792433 | 0.005265046 | 0.073875105 |
| Fcor | 1439834_at | -1.006061729 | 0.005906145 | 0.077727492 |
| Nipbl | 1442103_at | -1.251092678 | 0.006463627 | 0.080954194 |
| Tgfb1 | 1445360_at | -1.853388092 | 0.006592491 | 0.081527606 |
| Psmb8 | 1422962_a_at | -2.805817714 | 0.006746438 | 0.082498168 |
| Creb1 | 1428755_at | -2.709135357 | 0.00842715 | 0.092353841 |
| Bnip3 | 1422470_at | 4.08594527 | 0.009517431 | 0.097978919 |
| Creb5 | 1457222_at | 2.782121921 | 0.011615045 | 0.108908555 |
| Akt1 | 1425711_a_at | 0.643312065 | 0.013226622 | 0.116886603 |
| Pex11a | 1419365_at | 3.114987589 | 0.013427369 | 0.117743176 |
| Wnt5b | 1422602_a_at | 1.821566134 | 0.015112995 | 0.124997466 |
| Adrb2 | 1437302_at | -1.425485021 | 0.016312374 | 0.13005204 |
| Osbpl11 | 1436027_at | -1.513347684 | 0.016442532 | 0.130444086 |
| Bbs12 | 1447275_at | 2.085258954 | 0.016764282 | 0.131584735 |
| Dact1 | 1417937_at | 2.668260054 | 0.018729084 | 0.139389505 |
| Asxl1 | 1458380_at | -1.336329518 | 0.020033869 | 0.144567603 |
| Arl4a | 1425411_at | 1.291469422 | 0.020514069 | 0.146485916 |
| Sox8 | 1435438_at | 3.11014067 | 0.022232322 | 0.152924449 |
| Zc3h12a | 1443993_at | -1.394639385 | 0.023186221 | 0.156129026 |
| Zfp385a | 1418865_at | 0.542010075 | 0.023687294 | 0.157485763 |
| Hmga2 | 1450781_at | 1.095868613 | 0.02694941 | 0.168316138 |
| Alms1 | 1456950_at | -0.917436423 | 0.026999562 | 0.168445562 |
| Tgfb1i1 | 1418136_at | 2.245342116 | 0.03175692 | 0.182967407 |
| Jdp2 | 1450350_a_at | -1.716067966 | 0.038047468 | 0.201807159 |
| Crebbp | 1459804_at | -1.327455321 | 0.039460203 | 0.20599124 |
| Lrg1 | 1417290_at | -1.396551363 | 0.045891248 | 0.223712254 |
| Wnt5a | 1448818_at | 2.932630314 | 0.049273596 | 0.232642512 |
| Adipoq | 1422651_at | -0.967741253 | 0.04950593 | 0.233187147 |
| Sirt1 | 1418640_at | 0.664587861 | 0.049795512 | 0.233721239 |
| Jag1 | 1434070_at | 1.602428888 | 0.050991735 | 0.236724473 |
| Arid5b | 1458238_at | -0.685662171 | 0.051489457 | 0.237932994 |
| Ptgs2 | 1417263_at | 1.371927346 | 0.052627103 | 0.241065913 |
| Gata2 | 1450333_a_at | -0.420057378 | 0.056717396 | 0.251052809 |
| Med1 | 1450402_at | -1.571906461 | 0.059570019 | 0.257266033 |
| Dlk2 | 1420807_a_at | 0.373678953 | 0.068401715 | 0.276729974 |
| Axin1 | 1426966_at | 1.169289 | 0.069027484 | 0.27796505 |
| Ppard | 1425703_at | 0.434121886 | 0.076751272 | 0.294402282 |
| Retn | 1449182_at | -0.387213077 | 0.081515149 | 0.303534902 |
| Cebpa | 1418982_at | -0.634142288 | 0.082465927 | 0.305385975 |
| Tbl1x | 1455042_at | -0.543952328 | 0.085276819 | 0.31094428 |
| Cebpb | 1418901_at | -0.972281866 | 0.085444205 | 0.311252652 |
| Cby1 | 1451305_at | 0.673131945 | 0.087651962 | 0.315548462 |
| Mb | 1451203_at | -0.51130744 | 0.088606749 | 0.317238289 |
| Ncor2 | 1451841_a_at | 0.340384564 | 0.090456528 | 0.320981893 |
| Gsk3b | 1439931_at | 0.834614429 | 0.090614747 | 0.32122473 |
| Crebl2 | 1442738_at | -0.635267227 | 0.107915586 | 0.351948864 |
| Aldh6a1 | 1448104_at | 2.581164414 | 0.108694563 | 0.353034242 |
| Eif2ak3 | 1430371_x_at | -1.422549648 | 0.119792665 | 0.371639131 |
| Fabp4 | 1417023_a_at | -1.680412884 | 0.121138 | 0.373696644 |
| Ccdc85b | 1435589_at | 0.279290591 | 0.122081875 | 0.375133492 |
| Rarres2 | 1425091_at | 0.316286623 | 0.127825163 | 0.384259327 |
| Socs1 | 1450446_a_at | 0.28564968 | 0.129177821 | 0.386022436 |
| Sh3pxd2b | 1442919_at | 0.783611603 | 0.137852296 | 0.40031788 |
| Fam57b | 1454209_at | 0.247150807 | 0.143889355 | 0.408784179 |
| Taf8 | 1416450_at | 0.340135345 | 0.145111022 | 0.410548216 |
| Lrp6 | 1451022_at | 1.847234643 | 0.145204659 | 0.410548216 |

TABLE 1M-continued

Adipocyte Differentiation GO:0045444

| Symbol | probeid | logFC | P. Value | fdr |
|---|---|---|---|---|
| Runx1t1 | 1448785_at | 0.447542765 | 0.1596707 | 0.430417084 |
| Trib2 | 1426641_at | 0.891332721 | 0.183420649 | 0.461761357 |
| Ankrd26 | 1436071_at | 0.362057222 | 0.206617022 | 0.488193332 |
| Aamdc | 1451381_at | 1.068486032 | 0.218997978 | 0.501958012 |
| Trib3 | 1426065_a_at | 0.295148999 | 0.233681553 | 0.51862483 |
| Lpin1 | 1426516_a_at | 0.583917646 | 0.24135771 | 0.526996505 |
| Zfpm1 | 1451046_at | −0.189108731 | 0.250389917 | 0.536494732 |
| Noc3l | 1437500_at | 0.783741682 | 0.250779312 | 0.536893509 |
| Carm1 | 1419743_s_at | 0.647225506 | 0.253119301 | 0.539097732 |
| Ctbp2 | 1422887_a_at | −0.404782759 | 0.270763331 | 0.554900576 |
| Slc2a4 | 1415959_at | 0.176147069 | 0.27374878 | 0.557749536 |
| Msx2 | 1438351_at | 0.352902478 | 0.299225831 | 0.581271523 |
| Ctbp1 | 1415702_a_at | 0.63070087 | 0.307078777 | 0.58884036 |
| Bscl2 | 1420632_a_at | 0.208707574 | 0.319770256 | 0.600814793 |
| Socs7 | 1420766_at | 0.745400207 | 0.332937222 | 0.61166653 |
| Prdm16 | 1429309_at | 0.142308012 | 0.340168904 | 0.618323642 |
| Sfrp1 | 1428136_at | 0.163111293 | 0.344049035 | 0.62158781 |
| Mrap | 1451371_at | −0.159923525 | 0.354449217 | 0.630342999 |
| Mettl8 | 1451141_at | 0.661628871 | 0.377374795 | 0.648726201 |
| Wnt1 | 1425377_at | 0.369757817 | 0.379671843 | 0.650544352 |
| Gm6484 | 1427422_at | 0.125398475 | 0.407923447 | 0.673018565 |
| Adrb3 | 1421555_at | −0.101387422 | 0.481093024 | 0.728724651 |
| Aloxe3 | 1449237_at | 0.111671705 | 0.490075015 | 0.734658995 |
| Sod2 | 1454976_at | −0.464238608 | 0.498589239 | 0.741120235 |
| Sh2b2 | 1450718_at | 0.337876551 | 0.500932827 | 0.742889702 |
| Nudt7 | 1430896_s_at | −0.500929104 | 0.521799273 | 0.756028945 |
| Hes1 | 1418102_at | 0.121585835 | 0.55711349 | 0.780249527 |
| Gpr116 | 1440225_at | −0.647155618 | 0.579033461 | 0.794203154 |
| Dkkl1 | 1417787_at | 0.070573306 | 0.609619995 | 0.812529315 |
| Uchl1 | 1448260_at | 0.072150504 | 0.6101289 | 0.812826358 |
| Cebpd | 1456605_at | 0.188950666 | 0.638667475 | 0.829432786 |
| Gata3 | 1448886_at | −0.083381986 | 0.65162031 | 0.836542813 |
| Pparg | 1420715_a_at | −0.067019888 | 0.664841034 | 0.844180446 |
| Fndc5 | 1435115_at | 0.099988573 | 0.664919216 | 0.844180446 |
| Lrp5 | 1449299_at | 0.120069936 | 0.667173815 | 0.845349241 |
| Adig | 1424729_at | 0.059571714 | 0.676763232 | 0.850717398 |
| Mmp11 | 1417234_at | 0.084863835 | 0.717623641 | 0.872175047 |
| Lep | 1422582_at | −0.05140898 | 0.743335178 | 0.886299367 |
| Sfrp2 | 1448201_at | 0.267663483 | 0.765342683 | 0.898105369 |
| Wnt3a | 1422093_at | −0.038794612 | 0.81145358 | 0.919832305 |
| Adrb1 | 1423420_at | −0.021770889 | 0.873212928 | 0.947461132 |
| Wnt10b | 1426091_a_at | 0.026764532 | 0.926524869 | 0.96924821 |
| Fgf10 | 1420690_at | −0.003608569 | 0.986998638 | 0.99442913 |

Table 1N. Cellular differentiation GO categories represented at different stringencies in Grem1+ Grem1−

| Stringency and GO Category | Total Genes in Pathway | Number of Significant Genes in GO category significantly up in at stringency | Fraction of Significant Genes in GO category significantly up in at stringency |
|---|---|---|---|
| fdr < 0.025 | | | |
| Osteoblast differentiation; GO:0001649 | 118 | 5 | 0.04 |
| Chondrocyte Differentiation; GO:000164 | 154 | 10 | 0.06 |
| Adipocyte Differentiation; GO:0045444 | 131 | 5 | 0.04 |
| fdr < 0.05 | | | |
| Osteoblast differentiation; GO:0001649 | 118 | 29 | 0.25 |
| Chondrocyte Differentiation; GO:000164 | 154 | 43 | 0.28 |
| Adipocyte Differentiation; GO:0045444 | 131 | 17 | 0.13 |
| fdr < 0.1 | | | |
| Osteoblast differentiation; GO:0001649 | 118 | 38 | 0.32 |
| Chondrocyte Differentiation; GO:000164 | 154 | 61 | 0.40 |
| Adipocyte Differentiation; GO:0045444 | 131 | 24 | 0.18 |

TABLE 2

Primer sequences

| Gene | Purpose | Sequence (5'-3')/Sequence name (IDT descriptor) |
|---|---|---|
| F-Grem1 recombineering primer | Recombineering | GATTTTTACTAAATAACTTTCTTATTGTCTG TGTCCCCCTCTCTTTGTCCTTTGTCTAGAAT GTCCAATTTACTGACCGTACA (SEQ ID NO.: 1) |
| R-Grem1 recombineering primer | Recombineering | GTTGGCAGTAGGGTCCCCAGGAGGAGAAGC AACGCTCCCACAGTGTATGCGGTGCGATTA TTATGTACCTGACTGATGAAGTT (SEQ ID NO: 2) |
| F-Grem1-creERT | Genotyping | CTG TGT CGA ATT ACT CAG TTT GAT G (SEQ ID NO.: 3) |
| R-Grem1-creERT | Genotyping | AAT GTT GCT GGA TAG TTT TTA CTG C (SEQ ID NO: 4) |
| F-Grem1-LacZ | Genotyping | ATCCTCTGCATGGTCAGGTC (SEQ ID NO.: 5) |
| R-Grem1-LacZ | Genotyping | CGTGGCCTGATTCATTCC (SEQ ID NO.: 6) |
| F-R26-TdTomato or ZsGreen (the WPRE) | Genotyping | ACT GTG TTT GCT GAC GCA AC (SEQ ID NO: 7) |
| R-R26-TdTomato or ZsGreen (the WPRE) | Genotyping | CAA CAC CAC GGA ATT GTC AG (SEQ ID NO: 8) |
| F-Nes-GFP or 2.3Col-GFP or R26-Confetti (the GFP) | Genotyping | GAG CTG AAG GGC ATC GAC TTC AAG (SEQ ID NO.: 9) |
| R-Nes-GFP or 2.3Col-GFP or R26-Confetti (the GFP) | Genotyping | GGA CTG GGT GCT CAG GTA GTG G (SEQ ID NO.: 10) |
| F-Nes-CreERT | Genotyping | GCG GCA TGG TGC AAG TTG AAT (SEQ ID NO.: 11) |
| R-Nes-CreERT | Genotyping | CGT TCA CCG GCA TCA ACG TTT (SEQ ID NO.: 12) |
| F-R26-iDTA | Genotyping | ACC TGG TTA TGT AGA TTC CAT TCA A (SEQ ID NO.: 13) |
| R-R26-iDTA | Genotyping | CAG AAG TAA GGT TCC TTC ACA AAG A (SEQ ID NO.: 14) |
| Acan | qPCR | Mm.PT.56a.10174685 |
| Angpt2 | qPCR | Mm.PT.56a.29139310 |
| Bmp2 | qPCR | Mm.PT.58.10419414 |
| Cspg4 | qPCR | Mm.PT.56a.29461721 |
| Cxcl12 | qPCR | Mm.PT.56a.7098583.g |
| Fap | qPCR | Mm.PT.56a.31960536 |
| Gapdh | qPCR | Mm.PT.39a.1 |
| Grem1 | qPCR | Mm.PT.53a.31803129 |
| Id2 | qPCR | Mm.PT.58.13116812.g |
| Kitl | qPCR | Mm.PT.56a.6382703 |
| Klf4 | qPCR | Mm.PT.56a.10779296 |
| Lepr | qPCR | Mm.PT.56a.33275723 |
| Myod | qPCR | Mm.PT.56a.8193525 |

TABLE 2-continued

Primer sequences

| Gene | Purpose | Sequence (5'-3')/Sequence name (IDT descriptor) |
| --- | --- | --- |
| Nes | qPCR | Mm.PT.56a.5953887 |
| Pparg | qPCR | Mm.PT.56a.31161924 |
| Runx2 | qPCR | Mm.PT.56a.31234632.g |
| Sox9 | qPCR | Mm.PT.56a.42739087 |
| Sp7 (Osterix) | qPCR | Mm.PT.56a.10898265 |
| Wnt4 | qPCR | Mm.PT.56a.8723468 |
| GAPDH (human) | qPCR | Hs.PT.39a.22214836 |
| GREM1 (human) | qPCR | Hs.PT.53a.26917089.g |
| Acta2-RFP and R26-mT/mG | Phenotyping | Carriers were detected by red fluorescence of the tail |

TABLE 3A

Mice used in our study

| Mouse line used | Reference | Received from | Description |
| --- | --- | --- | --- |
| Grem1-creER$^T$ | Published here | Generated in the Wang lab. | A BAC transgenic in which the regulatory elements of Grem1 drive expression of a tamoxifen inducible Cre recombinase. Grem1 expressing cells express Cre recombinase that can, following binding of tamoxifen, translocate to the nucleus to recombine and thus activate fluorescent reporters or the diphtheria toxin subunit A lines described below. |
| Grem1-LacZ | Khokha et al, 2003 | investigator | A LacZ reporter is knocked in to the endogenous Grem1 locus. Cells that express Grem1 can be detected by LacZ activity. |
| Nes-creER$^T$ | Dranovsky et al., 2011 | investigator | A transgenic line in which a short regulatory sequence of Nes drives expression of a tamoxifen inducible Cre recombinase. Following administration of tamoxifen, Nes expressing cells express Cre recombinase that can translocate to the nucleus to recombine and thus activate fluorescent reporters. In this line a 5.3 kb region drives the CreERT2 upstream of the transcriptional start site of the Nestin gene. This fragment is fused to the CreERT2 followed by a polyA tail and then a 653 bp region of the 2nd intron (corresponding to base pare positions 2880–>3533 downstream of the start site). |
| Nes-GFP | Mignone et al., 2004 | investigator | A transgenic line in which a short regulatory sequence of Nes drives GFP expression. |
| 2.3ColGFP | Kalajzic et al., 2002 | JAX stock no. 13134 | A transgenic line in which a short (2.3 kb) regulatory sequence of rat Col1a1 drives GFP expression. This line is used to identify committed osteoblasts in mice. |
| Acta2-RFP | Magness et al., 2004 | investigator | A transgenic line in which a short regulatory sequence of Acta2 drives RFP expression. |
| R26-LSL-TdTomato | Madisen et al., 2010 | JAX stock no. 7909 | A cre recombinase activated red fluorescent reporter knocked into the Rosa26 locus. |
| R26-LSL-ZsGreen | Madisen et al., 2010 | JAX stock no. 7906 | A cre recombinase activated green fluorescent reporter knocked into the Rosa26 locus. |
| R26-LSL-mT/mG | Muzumdar et al., 2007 | JAX stock no. 7676 | A cre recombinase activated green fluorescent reporter knocked into the Rosa26 locus. Prior to recombination all cells express a red fluorescent protein, which allows easier appreciation of tissue architecture on fluorescent microscopy. |
| R26-LSL-Confetti | Snippert et al., 2010 | JAX stock no. 17492 | A cre recombinase activated fluorescent reporter knocked into the Rosa26 locus. The value of this reporter is that one of 4 fluorescent tags is expressed randomly following recombination, either, YFP, RFP, mCFP or nGFP. This allows clones to be mapped in vivo. |

TABLE 3A-continued

Mice used in our study

| Mouse line used | Reference | Received from | Description |
|---|---|---|---|
| R26-LSL-DTA | Voehringer et al., 2008 | JAX stock no. 9669 | A cre recombinase activated diphtheria toxin subunit A expressing construct knocked into the Rosa26 locus. This allowed cell specific programmed cell death. |

TABLE 3B

Other mice previously reported as marking mesenchymal stem/progenitor cells, not included in our study

| Mouse line used | Reported in | Description |
|---|---|---|
| Lepr-cre | Ding et al, 2012; Zhou et al 2014, Mizoguchi et al, 2014. | Lepr-cre is a knock-in, constitutive Cre line that primarily identifies perisinusoidal mesenchymal cells in the bone marrow. Across 3 papers the perisinusoidal cells it marks have been shown to not generate bone or cartilage in early post-natal life, but that in later life beginning around 2 months, Lepr+ perisinusoidal cells begin to differentiate into bone and adipocytes and, in fracture callus, chondrocytes. |
| Nes-Cre | Mendez-Ferrer, et al, 2010- first published in Tronche et al, 1999 | Lineage tracing of bone and cartilage has been reported from this line, albeit that the recombination may not perfectly mimic the perisinusoidal distribution of Nes-GFP. |
| Nes-CreERT | Mendez-Ferrer, et al, 2010-first published in Balordi & Fishell, 2007. | Lineage tracing of bone and cartilage has been reported from this line, albeit that the recombination may again not perfectly mimic the perisinusoidal distribution of Nes-GFP. |
| Osx-Cre | Mizoguchi et al, 2014. Maes et al, 2010, Park, et al 2012. | Osterix (Sp7) is a broad mesenchymal marker, but in adulthood is recognized as an early, but non-self-renewing, osteolineage marker. However, Osx is expressed in cell populations of varying potential throughout development and it was recently shown that perinatal Osx expressing cells (P5) are long-lived with bone and stromal potential. |
| Ng2-CreERT | Kunisaki et al, 2013; Feng, et al, 2011. | In the adult murine bone marrow Ng2-CreER$^T$ identifies periarteriolar cells, important for the HSC niche. In the tooth Ng2+ cells are mesenchymal stem/progenitor cells generating odontoblasts. |
| Acta2-CreER | Grcevic et al, 2012. | Acta2 expressing cells act as in vitro and in vivo mesenchymal stem/progenitor cells. Acta2 is also expressed in smooth muscle and thus is probably expressed in both differentiated and less differentiated mesenchymal populations. |
| Prx1-Cre | Logan et al, 2002. | Prx1 is expressed in early limb bud mesoderm and as a constitutive Cre will thus trace all lineages derived from limb bud mesoderm including bone, stroma and cartilage. It has been used in studies requiring broad mesodermal tracing and conditional knockouts. |

TABLE 4

Bmp2 pathway Genes, Grem1+VsGrem1− fdr < .05

| Symbol | Description | Log$_2$ FC |
|---|---|---|
| Acvrl | activin A receptor, type 1 | 6.94 |
| Bmp2 | bone morphogenetic protein 2 | 5.79 |
| Bmp5 | bone morphogenetic protein 5 | 4.36 |
| Bmp6 | bone morphogenetic protein 6 | 2.18 |
| Id2 | inhibitor of DNA binding 2 | 2.56 |

TABLE 5

Grem1+ vs Grem1 - Signficant KEGG Pathways

| Rank | Name | ID | pSize | onArray |
|---|---|---|---|---|
| 1 | ECM-receptor interaction | 4512 | 87 | 85 |
| 2 | PI3K-Akt signaling pathway | 4151 | 356 | 333 |
| 3 | Focal adhesion | 4510 | 205 | 203 |
| 4 | Fc gamma R-mediated phagocytosis | 4666 | 89 | 87 |
| 5 | Natural killer cell mediated cytotoxicity | 4650 | 125 | 112 |
| 6 | Osteoclast differentiation | 4380 | 127 | 118 |

TABLE 5-continued

| | Grem1+ vs Grem1 - Signficant KEGG Pathways | | | |
|---|---|---|---|---|
| 7 | Amoebiasis | 5146 | 120 | 113 |
| 8 | Proteoglycans in cancer | 5205 | 230 | 222 |
| 9 | Cytokine-cytokine receptor interaction | 4060 | 266 | 227 |
| 10 | B cell receptor signaling pathway | 4662 | 78 | 77 |
| 11 | Regulation of actin cytoskeleton | 4810 | 217 | 210 |
| 12 | Aldosterone-regulated sodium reabsorption | 4960 | 40 | 40 |
| 13 | Fc epsilon RI signaling pathway | 4664 | 71 | 70 |
| 14 | MAPK signaling pathway | 4010 | 259 | 253 |
| 15 | HIF-1 signaling pathway | 4066 | 113 | 104 |
| 16 | VEGF signaling pathway | 4370 | 66 | 66 |
| 17 | Leishmaniasis | 5140 | 66 | 66 |
| 18 | Jak-STAT signaling pathway | 4630 | 156 | 136 |
| 19 | Transcriptional misregulation in cancer | 5202 | 181 | 164 |
| 20 | Axon guidance | 4360 | 133 | 133 |
| 21 | Phosphatidylinositol signaling system | 4070 | 81 | 79 |
| 22 | Long-term depression | 4730 | 61 | 59 |
| 23 | Tuberculosis | 5152 | 179 | 170 |
| 24 | Bacterial invasion of epithelial cells | 5100 | 77 | 76 |
| 25 | Salivary secretion | 4970 | 77 | 73 |
| 26 | Pancreatic secretion | 4972 | 103 | 99 |
| 27 | Leukocyte transendothelial migration | 4670 | 121 | 116 |
| 28 | Rheumatoid arthritis | 5323 | 84 | 81 |
| 29 | Viral myocarditis | 5416 | 94 | 74 |
| 30 | Renal cell carcinoma | 5211 | 69 | 68 |
| 31 | Staphylococcus aureus infection | 5150 | 52 | 49 |
| 32 | Glioma | 5214 | 66 | 64 |
| 33 | Hepatitis B | 5161 | 149 | 140 |
| 34 | Small cell lung cancer | 5222 | 86 | 85 |
| 35 | HTLV-I infection | 5166 | 290 | 266 |
| 36 | Salmonella infection | 5132 | 79 | 77 |
| 37 | Amphetamine addiction | 5031 | 70 | 68 |
| 38 | Viral carcinogenesis | 5203 | 236 | 191 |
| 39 | GnRH signaling pathway | 4912 | 89 | 87 |

| NDE | tA | pNDE | pPERT | pG | pG FDR | Status |
|---|---|---|---|---|---|---|
| 26 | 4.91 | 4.E−12 | 0.00 | 1.E−08 | 2.E−06 | Activated |
| 48 | 2.53 | 3.E−08 | 0.02 | 3.E−07 | 2.E−05 | Activated |
| 49 | 2.36 | 6.E−17 | 0.02 | 4.E−07 | 2.E−05 | Activated |
| 27 | 1.53 | 1.E−12 | 0.12 | 2.E−06 | 7.E−05 | Not Applicable |
| 21 | 2.12 | 4.E−06 | 0.04 | 2.E−06 | 7.E−05 | Activated |
| 23 | 0.94 | 7.E−07 | 0.34 | 5.E−06 | 1.E−04 | Not Applicable |
| 25 | 0.65 | 2.E−08 | 0.52 | 8.E−06 | 2.E−04 | Not Applicable |
| 36 | 0.44 | 9.E−08 | 0.66 | 1.E−05 | 2.E−04 | Not Applicable |
| 32 | −1.70 | 1.E−05 | 0.08 | 1.E−05 | 2.E−04 | Not Applicable |
| 18 | 0.13 | 7.E−07 | 0.89 | 1.E−05 | 2.E−04 | Not Applicable |
| 34 | −0.10 | 2.E−07 | 0.92 | 1.E−05 | 2.E−04 | Not Applicable |
| 11 | −0.46 | 2.E−05 | 0.67 | 2.E−04 | 2.E−03 | Not Applicable |
| 14 | 1.00 | 8.E−05 | 0.30 | 3.E−04 | 3.E−03 | Not Applicable |
| 33 | 0.07 | 4.E−05 | 0.94 | 4.E−04 | 4.E−03 | Not Applicable |
| 16 | 1.71 | 6.E−04 | 0.07 | 5.E−04 | 4.E−03 | Not Applicable |
| 13 | −1.06 | 2.E−04 | 0.28 | 5.E−04 | 4.E−03 | Not Applicable |
| 13 | 0.88 | 2.E−04 | 0.36 | 6.E−04 | 5.E−03 | Not Applicable |
| 20 | −0.76 | 2.E−04 | 0.46 | 1.E−03 | 9.E−03 | Not Applicable |
| 22 | −0.47 | 5.E−04 | 0.34 | 2.E−03 | 0.01 | Not Applicable |
| 19 | −0.83 | 5.E−04 | 0.40 | 2.E−03 | 0.01 | Not Applicable |
| 13 | −0.73 | 1.E−03 | 0.30 | 3.E−03 | 0.02 | Not Applicable |
| 9 | 2.11 | 9.E−03 | 0.04 | 3.E−03 | 0.02 | Activated |
| 22 | 0.67 | 8.E−04 | 0.49 | 3.E−03 | 0.02 | Not Applicable |
| 13 | −0.36 | 7.E−04 | 0.72 | 4.E−03 | 0.02 | Not Applicable |
| 12 | −0.68 | 2.E−03 | 0.50 | 6.E−03 | 0.03 | Not Applicable |
| 15 | −0.24 | 1.E−03 | 0.82 | 7.E−03 | 0.04 | Not Applicable |
| 16 | 0.71 | 2.E−03 | 0.46 | 7.E−03 | 0.04 | Not Applicable |
| 11 | 1.53 | 1.E−02 | 0.09 | 7.E−03 | 0.04 | Not Applicable |
| 12 | −0.61 | 2.E−03 | 0.54 | 8.E−03 | 0.04 | Not Applicable |
| 11 | −0.88 | 3.E−03 | 0.39 | 8.E−03 | 0.04 | Not Applicable |
| 8 | −1.43 | 9.E−03 | 0.12 | 9.E−03 | 0.04 | Not Applicable |
| 10 | −1.11 | 5.E−03 | 0.22 | 9.E−03 | 0.04 | Not Applicable |
| 18 | −0.62 | 2.E−03 | 0.53 | 1.E−02 | 0.04 | Not Applicable |
| 12 | 1.19 | 6.E−03 | 0.23 | 1.E−02 | 0.04 | Not Applicable |
| 29 | 0.41 | 2.E−03 | 0.68 | 1.03E−02 | 0.040327256 | Not Applicable |
| 12 | 0.44 | 2.E−03 | 0.65 | 1.20E−02 | 0.045777725 | Not Applicable |
| 11 | 0.49 | 3.E−03 | 0.63 | 1.26E−02 | 0.0467475 | Not Applicable |
| 22 | −0.70 | 3.E−03 | 0.57 | 1.41E−02 | 0.049467655 | Not Applicable |
| 12 | 0.98 | 7.E−03 | 0.29 | 1.41E−02 | 0.049467655 | Not Applicable |

TABLE 6

Grem1+ vs Grem1 - Signficant Reactome Pathways

| Rank | Name |
|---|---|
| 1 | Collagen biosynthesis and modifying enzymes |
| 2 | MPS IIIC - Sanfilippo syndrome C |
| 3 | MPS IV - Morquio syndrome B |
| 4 | MPS VI - Maroteaux-Lamy syndrome |
| 5 | MPS II - Hunter syndrome |
| 6 | Glycosaminoglycan metabolism |
| 7 | MPS IX - Natowicz syndrome |
| 8 | MPS VII - Sly syndrome |
| 9 | MPS I - Hurler syndrome |
| 10 | MPS IIIB - Sanfilippo syndrome B |
| 11 | MPS IIIA - Sanfilippo syndrome A |
| 12 | MPS IIID - Sanfilippo syndrome D |
| 13 | MPS IV - Morquio syndrome A |
| 14 | Fcgamma receptor (FCGR) dependent phagocytosis |
| 15 | Cell surface interactions at the vascular wall |
| 16 | Collagen degradation |
| 17 | Integrin cell surface interactions |
| 18 | Assembly of collagen fibrils and other multimeric structures |
| 19 | Degradation of the extracellular matrix |
| 20 | Signaling by Rho GTPases |
| 21 | GPVI-mediated activation cascade |
| 22 | Response to elevated platelet cytosolic Ca2+ |
| 23 | Syndecan interactions |
| 24 | Elastic fibre formation |
| 25 | Signaling by Hippo |
| 26 | Activation of Matrix Metalloproteinases |
| 27 | Immunoregulatory interactions between a Lymphoid and a non-Lymphoid cell |
| 28 | Regulation of lipid metabolism by Peroxisome proliferator-activated receptor alpha (PPARalpha) |

| ID | pSize | onArray | NDE | tA | pNDE | pPERT | pG | pG FDR | Status |
|---|---|---|---|---|---|---|---|---|---|
| 5605856 | 52 | 50 | 20 | 1.96 | 0.E+00 | 0.05 | 0.00 | 7.E−05 | Activated |
| 5605255 | 110 | 108 | 25 | −0.98 | 0.E+00 | 0.32 | 0.00 | 7.E−05 | Not Applicable |
| 5605261 | 110 | 108 | 25 | −0.96 | 0.E+00 | 0.33 | 0.00 | 7.E−05 | Not Applicable |
| 5605253 | 110 | 108 | 25 | −0.96 | 0.E+00 | 0.34 | 0.00 | 7.E−05 | Not Applicable |
| 5605257 | 110 | 108 | 25 | −0.95 | 0.E+00 | 0.34 | 0.00 | 7.E−05 | Not Applicable |
| 5605249 | 110 | 108 | 25 | −0.96 | 0.E+00 | 0.35 | 0.00 | 7.E−05 | Not Applicable |
| 5605250 | 110 | 108 | 25 | −0.95 | 0.E+00 | 0.35 | 0.00 | 7.E−05 | Not Applicable |
| 5605256 | 110 | 108 | 25 | −0.94 | 0.E+00 | 0.35 | 0.00 | 7.E−05 | Not Applicable |
| 5605258 | 110 | 108 | 25 | −0.94 | 0.E+00 | 0.35 | 0.00 | 7.E−05 | Not Applicable |
| 5605252 | 110 | 108 | 25 | −0.94 | 0.E+00 | 0.35 | 0.00 | 7.E−05 | Not Applicable |
| 5605260 | 110 | 108 | 25 | −0.94 | 0.E+00 | 0.35 | 0.00 | 7.E−05 | Not Applicable |
| 5605259 | 110 | 108 | 25 | −0.93 | 0.E+00 | 0.35 | 0.00 | 7.E−05 | Not Applicable |
| 5605254 | 110 | 108 | 25 | −0.95 | 0.E+00 | 0.37 | 0.00 | 7.E−05 | Not Applicable |
| 5605170 | 72 | 71 | 17 | −0.53 | 1.E−06 | 0.61 | 0.00 | 1.E−04 | Not Applicable |
| 5605041 | 83 | 81 | 17 | 1.45 | 7.E−06 | 0.13 | 0.00 | 1.E−04 | Not Applicable |
| 5605823 | 31 | 31 | 10 | 1.47 | 1.E−05 | 0.13 | 0.00 | 2.E−04 | Not Applicable |
| 5605038 | 60 | 58 | 14 | 1.00 | 8.E−06 | 0.34 | 0.00 | 3.E−04 | Not Applicable |
| 5605828 | 27 | 27 | 9 | −0.91 | 2.E−05 | 0.56 | 0.00 | 1.E−03 | Not Applicable |
| 5605824 | 94 | 87 | 16 | −1.05 | 7.E−05 | 0.28 | 0.00 | 2.E−03 | Not Applicable |
| 5605351 | 100 | 97 | 15 | 1.77 | 8.E−04 | 0.06 | 0.00 | 4.E−03 | Not Applicable |
| 5605042 | 26 | 26 | 8 | 0.21 | 1.E−04 | 0.83 | 0.00 | 0.01 | Not Applicable |
| 5605037 | 86 | 81 | 14 | −0.17 | 4.E−04 | 0.93 | 0.00 | 0.02 | Not Applicable |
| 5605962 | 18 | 18 | 6 | 0.37 | 5.E−04 | 0.74 | 0.00 | 0.02 | Not Applicable |
| 5605850 | 36 | 36 | 7 | −1.32 | 6.E−03 | 0.12 | 0.01 | 0.03 | Not Applicable |
| 5605905 | 20 | 20 | 6 | 0.29 | 1.E−03 | 0.80 | 0.01 | 0.04 | Not Applicable |
| 5605848 | 45 | 39 | 8 | 0.93 | 2.E−03 | 0.36 | 0.01 | 0.04 | Not Applicable |
| 5605383 | 51 | 43 | 7 | 1.66 | 1.E−02 | 0.07 | 0.01 | 0.04 | Not Applicable |
| 5605592 | 73 | 73 | 11 | −1.10 | 5.E−03 | 0.23 | 0.01 | 0.04 | Not Applicable |

TABLE 7

ECM-Receptor Interaction Genes in Grem1+ Vs Grem1− (fdr < 0.05)

| Symbol | Description | Log$_2$ FC |
|---|---|---|
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |

TABLE 7-continued

ECM-Receptor Interaction Genes in Grem1+ Vs Grem1− (fdr < 0.05)

| Symbol | Description | Log₂ FC |
|---|---|---|
| Dag1 | dystroglycan 1 | 2.35 |
| Hspg2 | perlecan (heparan sulfate proteoglycan 2) | 2.60 |
| Ibsp | integrin binding sialoprotein | 3.26 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Lama4 | laminin, alpha 4 | 1.80 |
| Lamb2 | laminin, beta 2 | 2.50 |
| Npnt | nephronectin | 3.91 |
| Sdc1 | syndecan 1 | 2.76 |
| Sdc4 | syndecan 4 | 4.91 |
| Thbs3 | thrombospondin 3 | 4.57 |

TABLE 8

PI3K-Akt Signaling Genes in Grem1+ Vs Grem1− (fdr < 0.05)

| Symbol | Description | Log₂ FC |
|---|---|---|
| Ccnd1 | cyclin D1 | 4.35 |
| Ccnd3 | cyclin D3 | −2.04 |
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |
| Creb3l2 | cAMP responsive element binding protein 3-like 2 | 4.85 |
| Csf1r | colony stimulating factor 1 receptor | −1.73 |
| Fgf2 | fibroblast growth factor 2 | 5.70 |
| Fgfr1 | fibroblast growth factor receptor 1 | 2.60 |
| Fgfr2 | fibroblast growth factor receptor 2 | 5.65 |
| Fgfr3 | fibroblast growth factor receptor 3 | 3.86 |
| Ibsp | integrin binding sialoprotein | 3.26 |
| Igf1 | insulin-like growth factor 1 | 4.11 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Lama4 | laminin, alpha 4 | 1.80 |
| Lamb2 | laminin, beta 2 | 2.50 |
| Lpar1 | lysophosphatidic acid receptor 1 | 3.03 |
| Lpar4 | lysophosphatidic acid receptor 4 | 4.46 |
| Lpar6 | lysophosphatidic acid receptor 6 | −3.83 |
| Mapk1 | mitogen-activated protein kinase 1 | −3.32 |
| Myb | myeloblastosis oncogene | −5.06 |
| Ngf | nerve growth factor | 5.93 |
| Osmr | oncostatin M receptor | 5.40 |
| Pdgfa | platelet derived growth factor, alpha | 1.50 |
| Pik3cd | phosphatidylinositol 3-kinase catalytic delta polypeptide | −2.58 |
| Pten | phosphatase and tensin homolog | −3.97 |
| Ptk2 | PTK2 protein tyrosine kinase 2 | 2.83 |
| Rheb | Ras homolog enriched in brain | 1.33 |
| Sgk1 | serum/glucocorticoid regulated kinase 1 | 2.45 |
| Sos2 | son of sevenless homolog 2 (Drosophila) | −2.70 |
| Syk | spleen tyrosine kinase | −4.15 |
| Thbs3 | thrombospondin 3 | 4.57 |
| Tlr4 | toll-like receptor 4 | −2.88 |
| Vegfa | vascular endothelial growth factor A | 1.87 |
| Ywhaq | tyrosine 3-monooxygenase/tryptophan 5-monooxygenase activation protein, theta polypeptide | 1.77 |

TABLE 9

Focal Adhesion Genes in Grem1+ Vs Grem1− (fdr < 0.05)

| Symbol | Description | Log₂ FC |
|---|---|---|
| Actn4 | actinin alpha 4 | 1.47 |
| Capn2 | calpain 2 | 3.45 |
| Cav1 | caveolin 1, caveolae protein | 3.07 |
| Cav2 | caveolin 2 | 3.08 |
| Ccnd1 | cyclin D1 | 4.35 |
| Ccnd3 | cyclin D3 | −2.04 |
| Chad | chondroadherin | 5.39 |
| Col11a1 | collagen, type XI, alpha 1 | 3.77 |
| Col11a2 | collagen, type XI, alpha 2 | 4.14 |
| Col27a1 | collagen, type XXVII, alpha 1 | 2.88 |
| Col4a2 | collagen, type IV, alpha 2 | 1.49 |
| Col4a5 | collagen, type IV, alpha 5 | 4.27 |
| Col5a1 | collagen, type V, alpha 1 | 3.09 |
| Col5a2 | collagen, type V, alpha 2 | 2.49 |
| Col6a1 | collagen, type VI, alpha 1 | 5.01 |
| Col6a2 | collagen, type VI, alpha 2 | 4.00 |
| Col6a3 | collagen, type VI, alpha 3 | 4.66 |
| Comp | cartilage oligomeric matrix protein | 4.00 |
| Flnb | filamin, beta | 2.89 |
| Flnc | filamin C, gamma | 3.35 |
| Ibsp | integrin binding sialoprotein | 3.26 |
| Igf1 | insulin-like growth factor 1 | 4.11 |
| Itga4 | integrin alpha 4 | −4.24 |
| Itga5 | integrin alpha 5 (fibronectin receptor alpha) | 3.73 |
| Itga6 | integrin alpha 6 | 2.17 |
| Itgav | integrin alpha V | 2.81 |
| Itgb3 | integrin beta 3 | −1.62 |
| Jun | jun proto-oncogene | 1.98 |
| Lama4 | laminin, alpha 4 | 1.80 |
| Lamb2 | laminin, beta 2 | 2.50 |
| Mapk1 | mitogen-activated protein kinase 1 | −3.32 |
| Mylk | myosin, light polypeptide kinase | 2.14 |
| Pak3 | p21 protein (Cdc42/Rac)-activated kinase 3 | 5.49 |
| Parvg | parvin, gamma | −3.07 |
| Pdgfa | platelet derived growth factor, alpha | 1.50 |
| Pik3cd | phosphatidylinositol 3-kinase catalytic delta polypeptide | −2.58 |
| Prkcb | protein kinase C, beta | −3.85 |
| Prkcg | protein kinase C, gamma | 2.75 |
| Pten | phosphatase and tensin homolog | −3.97 |
| Ptk2 | PTK2 protein tyrosine kinase 2 | 2.83 |
| Rac2 | RAS-related C3 botulinum substrate 2 | −3.03 |
| Sos2 | son of sevenless homolog 2 (Drosophila) | −2.70 |
| Thbs3 | thrombospondin 3 | 4.57 |
| Vasp | vasodilator-stimulated phosphoprotein | −1.39 |
| Vav1 | vav 1 oncogene | −4.46 |
| Vav2 | vav 2 oncogene | 2.38 |
| Vav3 | vav 3 oncogene | −2.01 |
| Vegfa | vascular endothelial growth factor A | 1.87 |
| Xiap | X-linked inhibitor of apoptosis | −2.45 |

TABLE 10

| Osteoblast differentiation GO:0001649 | | | | |
|---|---|---|---|---|
| Symbol | probeid | logFC | P. Value | fdr |
| Shox2 | 1438042_at | 7.13969309 | 1.12E−05 | 0.02471733 |
| Fgfr2 | 1433489_s_at | 5.65231788 | 1.51E−05 | 0.02471733 |
| Bmp2 | 1423635_at | 5.78726506 | 5.84E−05 | 0.02471733 |
| Col9a1 | 1421381_a_at | 5.14384919 | 7.20E−05 | 0.02471733 |
| Sox9 | 1424950_at | 6.90133905 | 0.0001102 | 0.02471733 |
| Comp | 1419527_at | 3.99952788 | 0.00013709 | 0.02523526 |
| Papss2 | 1421987_at | 5.85768973 | 0.00013725 | 0.02523526 |
| Col10a1 | 1422253_at | 4.64970077 | 0.00015096 | 0.02523526 |
| Matn1 | 1418477_at | 5.63933284 | 0.00019186 | 0.02642403 |
| Impad1 | 1437290_at | 4.00009567 | 0.00019808 | 0.02656323 |
| Ltbp3 | 1437833_at | 2.9661723 | 0.00021743 | 0.02704011 |
| Sp7 | 1418425_at | 3.10351174 | 0.00026166 | 0.02862484 |
| Ddr2 | 1422738_at | 3.89722768 | 0.00026991 | 0.02873843 |
| Ankrd11 | 1458452_at | −1.7496439 | 0.00042781 | 0.03083902 |
| Bmp6 | 1450759_at | 2.1776606 | 0.00052763 | 0.03237488 |
| Thbs3 | 1416623_at | 4.56764372 | 0.00056966 | 0.03323698 |
| Ptprc | 1440165_at | −5.6734651 | 0.00064536 | 0.03437141 |
| Igf1 | 1419519_at | 4.10582922 | 0.00076686 | 0.03552034 |
| Mef2c | 1451506_at | 1.5622972 | 0.00077261 | 0.03552034 |
| Gli3 | 1456067_at | 2.45472986 | 0.00081314 | 0.0360597 |
| Insig1 | 1454671_at | 2.08360386 | 0.00085701 | 0.03646133 |
| Csgalnact1 | 1452365_at | 6.10211317 | 0.00087003 | 0.03646133 |
| Asxl2 | 1460597_at | −2.6979367 | 0.00092542 | 0.0368767 |
| Hspg2 | 1418670_s_at | 2.60149201 | 0.00098897 | 0.03770361 |
| Dlx5 | 1449863_a_at | 3.7588245 | 0.00106207 | 0.03918556 |
| Sparc | 1416589_at | 1.60412839 | 0.00113447 | 0.04021149 |
| Slc38a10 | 1427295_at | 1.83634246 | 0.0012518 | 0.04142547 |
| Has2 | 1449169_at | 4.99235834 | 0.00126234 | 0.04164276 |
| Fgfr3 | 1421841_at | 3.86261057 | 0.00148679 | 0.04425268 |
| Npr2 | 1427191_at | 3.46860457 | 0.00168539 | 0.04660501 |
| Sulf2 | 1442408_at | 1.6036124 | 0.00181894 | 0.04807212 |
| Serpinh1 | 1450843_a_at | 1.29654547 | 0.00188638 | 0.04851906 |
| Sema4d | 1420824_at | −1.8029043 | 0.00194795 | 0.04888768 |
| Phospho2 | 1425190_a_at | −2.8140356 | 0.00197866 | 0.04910038 |
| Alpl | 1423611_at | 2.96345394 | 0.00315219 | 0.05979792 |
| Cadm1 | 1417376_a_at | 4.10590728 | 0.00374974 | 0.06413052 |
| Smad1 | 1448208_at | 3.17101958 | 0.00393954 | 0.06521738 |
| Fat4 | 1459749_s_at | 3.23899393 | 0.00402532 | 0.06597077 |
| Runx2 | 1424704_at | 2.8878129 | 0.0055077 | 0.0751405 |
| Rarg | 1419415_a_at | 1.55028671 | 0.0058013 | 0.07697684 |
| Insig2 | 1417980_a_at | 2.44324681 | 0.00584458 | 0.07727179 |
| Sik3 | 1460439_at | −1.0857648 | 0.00755719 | 0.08777671 |
| Cyp26b1 | 1460011_at | 2.41494558 | 0.0078034 | 0.0892175 |
| Glg1 | 1460554_s_a | 1.08231524 | 0.00954803 | 0.09811991 |
| Pex7 | 1418988_at | −1.5114512 | 0.01007962 | 0.1014008 |
| Gnas | 1450186_s_a | 1.15793611 | 0.01017669 | 0.1019462 |
| Smad5 | 1433641_at | 1.32605317 | 0.01176342 | 0.10947652 |
| Ostc | 1449139_at | 1.47773534 | 0.01312531 | 0.1164395 |
| Plxnb1 | 1435254_at | 2.94240991 | 0.01342921 | 0.11774318 |
| Bbx | 1425835_a_at | 2.44695116 | 0.01448366 | 0.12264883 |
| Twist1 | 1418733_at | 1.38261178 | 0.01576956 | 0.1278689 |
| Nab1 | 1438819_at | −2.9216854 | 0.01616797 | 0.1294138 |
| Asxl1 | 1458380_at | −1.3363295 | 0.02003387 | 0.1445676 |
| Osr2 | 1426155_a_at | 0.50221439 | 0.02482068 | 0.16093223 |
| Setdb1 | 1451833_a_at | −0.705544 | 0.02602998 | 0.16493091 |
| Pthlh | 1422324_a_at | 2.22023888 | 0.02765368 | 0.17061675 |
| Ift80 | 1427568_a_at | 2.13652764 | 0.03549998 | 0.19425924 |
| Col2a1 | 1450567_a_at | 0.51632868 | 0.03698764 | 0.19875846 |
| Cited2 | 1452207_at | 0.77720105 | 0.038182 | 0.20226056 |
| Pax1 | 1449359_at | 3.12937179 | 0.03911755 | 0.20500123 |
| Ski | 1426373_at | 1.20823577 | 0.03974484 | 0.20676946 |
| Rhoa | 1437628_s_a | −0.4614252 | 0.04469134 | 0.22031089 |
| Bnc2 | 1438861_at | 4.23430725 | 0.04850308 | 0.23058618 |
| Whsc1 | 1435136_at | −1.0033239 | 0.06021278 | 0.25860931 |
| Inppl1 | 1460394_a_at | 0.56759927 | 0.06832218 | 0.27657199 |
| Mcph1 | 1439115_at | −1.2317502 | 0.07426703 | 0.289485 |
| Fgf18 | 1449545_at | 1.95630563 | 0.08013069 | 0.30080298 |
| Hoxa11 | 1420414_at | 0.51117163 | 0.134279 | 0.39421853 |
| Ctc1 | 1423656_x_a | −0.3454466 | 0.13779297 | 0.40027058 |
| Sh3pxd2b | 1442919_at | 0.7836116 | 0.1378523 | 0.40031788 |
| Evc | 1448876_at | 1.72036865 | 0.14073692 | 0.40431581 |
| Lrp6 | 1451022_at | 1.84723464 | 0.14520466 | 0.41054822 |
| Grem1 | 1425357_a_at | 2.03742601 | 0.15410452 | 0.42297152 |
| Amer1 | 1439565_at | −1.2063171 | 0.16004689 | 0.43090105 |
| Scx | 1456291_x_a | 0.27534435 | 0.16950076 | 0.44294863 |
| Ptger4 | 1424208_at | −0.9729169 | 0.17847174 | 0.45532605 |

TABLE 10-continued

Osteoblast differentiation GO:0001649

| Symbol | probeid | logFC | P. Value | fdr |
|---|---|---|---|---|
| Ryr1 | 1427306_at | −0.2950732 | 0.19148114 | 0.47135849 |
| Rab23 | 1454876_at | 0.859713 | 0.19401749 | 0.47439891 |
| Trim45 | 1441412_s_at | 0.20342791 | 0.20276127 | 0.48402773 |
| Axin2 | 1436845_at | 0.38799213 | 0.21124748 | 0.49331913 |
| Lrrc17 | 1429679_at | 0.23301036 | 0.23562804 | 0.52060256 |
| Pitx2 | 1424797_a_at | 1.07081967 | 0.23628235 | 0.52138414 |
| Carm1 | 1419743_s_a | 0.64722551 | 0.2531193 | 0.53909773 |
| Dym | 1423736_a_at | −0.9150064 | 0.27126619 | 0.55550201 |
| Sulf1 | 1436319_at | 1.19568804 | 0.27432954 | 0.5581008 |
| Smad9 | 1450265_at | 0.16221583 | 0.2789619 | 0.56241214 |
| Prpsap2 | 1452062_at | −0.3149736 | 0.28405301 | 0.56696207 |
| Msx2 | 1438351_at | 0.35290248 | 0.29922583 | 0.58127152 |
| Mef2d | 1421388_at | −0.1866246 | 0.31750884 | 0.59885034 |
| Nppc | 1422790_at | 0.1607409 | 0.31851616 | 0.59964979 |
| Fam73b | 1454621_s_at | 0.2994231 | 0.32117143 | 0.60193506 |
| Acp5 | 1431609_a_at | −0.9309661 | 0.33111888 | 0.61004404 |
| Fgf4 | 1420086_x_a | 0.18263932 | 0.35648536 | 0.63248628 |
| Cbs | 1423844_s_a | 0.20063418 | 0.36616507 | 0.64041613 |
| Wnt1 | 1425377_at | 0.36975782 | 0.37967184 | 0.65054435 |
| T | 1419304_at | 0.16388178 | 0.39058468 | 0.65912444 |
| Col1a1 | 1423669_at | −0.6212641 | 0.40659023 | 0.6718836 |
| Hoxb4 | 1451761_at | −0.1272661 | 0.46260484 | 0.71610719 |
| Sp5 | 1422914_at | −0.1174096 | 0.4953465 | 0.73863064 |
| Hoxd11 | 1450584_at | 0.09335222 | 0.51678271 | 0.75267603 |
| Bmp4 | 1422912_at | −0.1515746 | 0.52844446 | 0.76072052 |
| Fgf8 | 1451882_a_at | 0.08277176 | 0.56350817 | 0.78452791 |
| Rarb | 1454906_at | 0.13246962 | 0.58074285 | 0.79545915 |
| Msx1 | 1417127_at | −0.0792768 | 0.6088118 | 0.81219928 |
| Por | 1416933_at | −0.0809813 | 0.64020848 | 0.83040587 |
| Thbs1 | 1460302_at | −0.0940899 | 0.6403299 | 0.83041932 |
| Rara | 1450180_a_at | −0.1450325 | 0.65688912 | 0.83924187 |
| Lrp5 | 1449299_at | 0.12006994 | 0.66717382 | 0.84534924 |
| Tfap2a | 1421996_at | 0.04882766 | 0.73011248 | 0.87883831 |
| Lep | 1422582_at | −0.051409 | 0.74333518 | 0.88629937 |
| Spns2 | 1451601_a_at | −0.0930905 | 0.75077046 | 0.89005592 |
| Nab2 | 1417930_at | −0.1414283 | 0.76360144 | 0.89720433 |
| Sfrp2 | 1448201_at | 0.26766348 | 0.76534268 | 0.89810537 |
| Dchs1 | 1429163_at | 0.03405801 | 0.85190273 | 0.93849266 |
| Sbds | 1426480_at | −0.0651239 | 0.88207204 | 0.95094397 |
| Bglap2 | 1449880_s_at | 0.03089077 | 0.96146152 | 0.98359981 |
| Cdx1 | 1449582_at | −0.0012411 | 0.99265715 | 0.99719485 |
| Frem1 | 1455280_at | 0.0010303 | 0.99394523 | 0.99782363 |

TABLE 11

Chondrocyte differentiation GO:0002062

| Symbol | probeid | logFC | P. Value | globalfdr |
|---|---|---|---|---|
| Sox5 | 1452511_at | 7.22767132 | 7.96E−06 | 0.02471733 |
| Frzb | 1416658_at | 6.48749238 | 8.83E−06 | 0.02471733 |
| Shox2 | 1438042_at | 7.13969309 | 1.12E−05 | 0.02471733 |
| Trps1 | 1438214_at | 3.40755204 | 4.76E−05 | 0.02471733 |
| Cytl1 | 1456793_at | 6.87459727 | 5.09E−05 | 0.02471733 |
| Bmp2 | 1423635_at | 5.78726506 | 5.84E−05 | 0.02471733 |
| Col11a2 | 1423578_at | 4.14206689 | 6.46E−05 | 0.02471733 |
| Pkdcc | 1454838_s_at | 7.28962976 | 6.74E−05 | 0.02471733 |
| Col9a1 | 1421381_a_at | 5.14384919 | 7.20E−05 | 0.02471733 |
| Sox9 | 1424950_at | 6.90133905 | 0.0001102 | 0.02471733 |
| Tgfb2 | 1423250_a_at | 5.54649939 | 0.00012244 | 0.02520744 |
| Comp | 1419527_at | 3.99952788 | 0.00013709 | 0.02523526 |
| Col10a1 | 1422253_at | 4.64970077 | 0.00015096 | 0.02523526 |
| Matn1 | 1418477_at | 5.63933284 | 0.00019186 | 0.02642403 |
| Impad1 | 1437290_at | 4.00009567 | 0.00019808 | 0.02656323 |
| Sox6 | 1447655_x_at | 3.04224037 | 0.00020449 | 0.0267325 |
| Ltbp3 | 1437833_at | 2.9661723 | 0.00021743 | 0.02704011 |
| Nfib | 1434101_at | 2.200371 | 0.00030068 | 0.02873843 |
| Chst11 | 1450509_at | 4.02884726 | 0.00032235 | 0.02907679 |
| Creb3l2 | 1452381_at | 4.85293127 | 0.00046023 | 0.03115804 |
| Bmp6 | 1450759_at | 2.1776606 | 0.00052763 | 0.03237488 |
| Col11a1 | 1418599_at | 2.34126506 | 0.00053144 | 0.03247748 |
| Thbs3 | 1416623_at | 4.56764372 | 0.00056966 | 0.03323698 |
| Mmp13 | 1417256_at | 4.24452375 | 0.00061702 | 0.03397116 |

TABLE 11-continued

| Chondrocyte differentiation GO:0002062 | | | | |
|---|---|---|---|---|
| Symbol | probeid | logFC | P. Value | globalfdr |
| Cyr61 | 1438133_a_at | 5.69119846 | 0.00063681 | 0.03419138 |
| Mia3 | 1459984_at | 2.37058997 | 0.00065816 | 0.03447572 |
| Hif1a | 1448183_a_at | 1.72827087 | 0.00074424 | 0.03532241 |
| Bmp5 | 1455851_at | 4.3611194 | 0.00075454 | 0.03535411 |
| Mef2c | 1451506_at | 1.5622972 | 0.00077261 | 0.03552034 |
| Fgf2 | 1449826_a_at | 5.70455759 | 0.00078373 | 0.03566748 |
| Gli3 | 1456067_at | 2.45472986 | 0.00081314 | 0.0360597 |
| Pth1r | 1417092_at | 5.14446867 | 0.00081315 | 0.0360597 |
| Acan | 1449827_at | 3.41833726 | 0.0008224 | 0.03611613 |
| Fgfr1 | 1424050_s_a | 2.60129371 | 0.00086507 | 0.03646133 |
| Csgalnact1 | 1452365_at | 6.10211317 | 0.00087003 | 0.03646133 |
| Hspg2 | 1418670_s_a | 2.60149201 | 0.00098897 | 0.03770361 |
| Mgp | 1448416_at | 3.3507084 | 0.00116189 | 0.04404339 |
| Snai2 | 1418673_at | 5.03701152 | 0.00128582 | 0.04171829 |
| Fgfr3 | 1421841_at | 3.86261057 | 0.00148679 | 0.04425268 |
| Maf | 1437473_at | 3.76980305 | 0.00153687 | 0.04489271 |
| Ctgf | 1416953_at | 2.49942916 | 0.00172491 | 0.04701858 |
| Sulf2 | 1442408_at | 1.6036124 | 0.00181894 | 0.04807212 |
| Serpinh1 | 1450843_a_at | 1.29654547 | 0.00188638 | 0.04851906 |
| Thra | 1443952_at | 1.82594965 | 0.00237175 | 0.05300708 |
| Zbtb16 | 1419874_x_at | 3.80377306 | 0.00239811 | 0.05325226 |
| Bmp8a | 1449873_at | 2.20192492 | 0.00384863 | 0.06493723 |
| Smad1 | 1448208_at | 3.17101958 | 0.00393954 | 0.06521738 |
| Pkd1 | 1460210_at | 2.9085668 | 0.00405261 | 0.06613797 |
| Bmp7 | 1418910_at | 1.92696736 | 0.00418937 | 0.06714193 |
| Mex3c | 1444701_at | 2.84275529 | 0.00439563 | 0.06871649 |
| Bmpr1a | 1425492_at | 1.36200773 | 0.00516927 | 0.07349907 |
| Runx2 | 1424704_at | 2.8878129 | 0.0055077 | 0.0751405 |
| Rarg | 1419415_a_at | 1.55028671 | 0.0058013 | 0.07697684 |
| Barx2 | 1421761_a_at | 0.85624097 | 0.00640975 | 0.08068276 |
| Tgfb1 | 1445360_at | −1.8533881 | 0.00659249 | 0.08152761 |
| Lect1 | 1460258_at | 4.58986317 | 0.00697288 | 0.08388477 |
| Ctnnb1 | 1450008_a_at | 1.66261927 | 0.00720075 | 0.08544095 |
| Tgfbr2 | 1426397_at | 1.86659547 | 0.0075086 | 0.08755963 |
| Sik3 | 1460439_at | −1.0857648 | 0.00755719 | 0.08777671 |
| Hoxc4 | 1422870_at | 1.19796075 | 0.00761056 | 0.08803383 |
| Otor | 1425083_at | 4.22357952 | 0.00876964 | 0.09435106 |
| Ror2 | 1457128_at | 4.33909419 | 0.008963 | 0.09531397 |
| Glg1 | 1460554_s_a | 1.08231524 | 0.00954803 | 0.09811991 |
| Tgfbr1 | 1420893_a_at | −1.553593 | 0.00976607 | 0.09956142 |
| Gnas | 1450186_s_a | 1.15793611 | 0.01017669 | 0.1019462 |
| Smad5 | 1433641_at | 1.32605317 | 0.01176342 | 0.10947652 |
| Prkca | 1427562_a_at | 2.10613284 | 0.01358718 | 0.11834592 |
| Hes5 | 1456010_x_at | −2.1231445 | 0.01655693 | 0.13093705 |
| Gli2 | 1459211_at | 1.04059295 | 0.0176753 | 0.13518291 |
| Mapk14 | 1426104_at | −1.5532261 | 0.02097546 | 0.14796945 |
| Lnp | 1453035_at | −2.9755281 | 0.02392091 | 0.15807429 |
| Osr2 | 1426155_a_at | 0.50221439 | 0.02482068 | 0.16093223 |
| Hmga2 | 1450781_at | 1.09586861 | 0.02694941 | 0.16831614 |
| Pthlh | 1422324_a_at | 2.22023888 | 0.02765368 | 0.17061675 |
| Wnt9a | 1436978_at | 0.87174088 | 0.02785817 | 0.17122255 |
| Bmpr1b | 1437312_at | 1.25973479 | 0.02801041 | 0.17173704 |
| Prrx1 | 1432129_a_at | 1.47773595 | 0.0280624 | 0.17191557 |
| Foxd1 | 1418876_at | 4.46730525 | 0.03043986 | 0.17907112 |
| Ift80 | 1427568_a_at | 2.13652764 | 0.03549998 | 0.19425924 |
| Col2a1 | 1450567_a_at | 0.51632868 | 0.03698764 | 0.19875846 |
| Thrb | 1422202_at | 2.48066506 | 0.04363391 | 0.21759789 |
| Atp7a | 1418774_a_at | −1.6739022 | 0.04473941 | 0.22045143 |
| Mapk3 | 1427060_at | −0.665697 | 0.04913025 | 0.23233967 |
| Wnt5a | 1448818_at | 2.93263031 | 0.0492736 | 0.23264251 |
| Bmp1 | 1427457_a_at | 2.43028686 | 0.05127348 | 0.23736193 |
| Rela | 1419536_a_at | 1.04767874 | 0.05767973 | 0.25345212 |
| Hoxa5 | 1443803_x_at | 1.0275933 | 0.06149235 | 0.26170129 |
| Esrra | 1442864_at | −0.6446893 | 0.06725047 | 0.27435072 |
| Fgf18 | 1449545_at | 1.95630563 | 0.08013069 | 0.30080298 |
| Hoxa3 | 1427433_s_at | 0.507085 | 0.08120338 | 0.30287153 |
| Zbtb7a | 1437255_at | −0.3664643 | 0.09699201 | 0.33330316 |
| Runx3 | 1440275_at | 0.96780328 | 0.09793019 | 0.33494632 |
| Hoxb3 | 1427605_at | 0.39418388 | 0.09973918 | 0.33804288 |
| Edn1 | 1451924_a_at | −0.2982996 | 0.10195385 | 0.34187512 |
| Eif2ak3 | 1430371_x_at | −1.4225496 | 0.11979267 | 0.37163913 |
| Satb2 | 1425904_at | 0.48646604 | 0.12821542 | 0.38470549 |
| Bbs1 | 1437310_at | 1.90386954 | 0.12829484 | 0.38470549 |
| Hoxa11 | 1420414_at | 0.51117163 | 0.134279 | 0.39421853 |
| Bmp8b | 1440706_at | 0.26308768 | 0.13555736 | 0.39655082 |
| Foxd2 | 1442315_at | 0.46320213 | 0.14384418 | 0.40876544 |

TABLE 11-continued

Chondrocyte differentiation GO:0002062

| Symbol | probeid | logFC | P. Value | globalfdr |
|---|---|---|---|---|
| Lrp6 | 1451022_at | 1.84723464 | 0.14520466 | 0.41054822 |
| Zeb1 | 1418926_at | 1.16354749 | 0.14660325 | 0.41268652 |
| Fgf9 | 1438718_at | −0.3966601 | 0.15928736 | 0.42979473 |
| Scx | 1456291_x_at | 0.27534435 | 0.16950076 | 0.44294863 |
| Wnt7a | 1458334_at | 0.23058566 | 0.17829566 | 0.45510852 |
| Mkks | 1422627_a_at | 0.62949897 | 0.20423492 | 0.48574462 |
| Bbs2 | 1424478_at | 1.18847208 | 0.20451523 | 0.48587449 |
| Axin2 | 1436845_at | 0.38799213 | 0.21124748 | 0.49331913 |
| Arid5a | 1451340_at | −0.3128111 | 0.21194496 | 0.49438477 |
| Hand1 | 1417525_at | 0.20127201 | 0.24088701 | 0.52659659 |
| Carm1 | 1419743_s_a | 0.64722551 | 0.2531193 | 0.53909773 |
| Sulf1 | 1436319_at | 1.19568804 | 0.27432954 | 0.5581008 |
| Smad9 | 1450265_at | 0.16221583 | 0.2789619 | 0.56241214 |
| Mycn | 1417155_at | 0.39769166 | 0.2893957 | 0.57218164 |
| Pitx1 | 1419514_at | 0.1702969 | 0.29146369 | 0.57395417 |
| Msx2 | 1438351_at | 0.35290248 | 0.29922583 | 0.58127152 |
| Prrx2 | 1432331_a_at | 0.73191217 | 0.30091849 | 0.58270253 |
| Wnt7b | 1420892_at | 0.15715266 | 0.31454776 | 0.59632366 |
| Mef2d | 1421388_at | −0.1866246 | 0.31750884 | 0.59885034 |
| Nppc | 1422790_at | 0.1607409 | 0.31851616 | 0.59964979 |
| Chrdl2 | 1420539_at | 0.20332488 | 0.34147543 | 0.61922033 |
| Uncx | 1419633_at | 0.14875918 | 0.35394085 | 0.62995605 |
| Fgf4 | 1420086_x_at | 0.18263932 | 0.35648536 | 0.63248628 |
| Cbs | 1423844_s_a | 0.20063418 | 0.36616507 | 0.64041613 |
| Cst10 | 1449447_at | 0.19712187 | 0.36842711 | 0.6420478 |
| Gdf5 | 1419139_at | 0.12908806 | 0.37130522 | 0.6441108 |
| Foxd4 | 1422318_at | −0.1344761 | 0.3797373 | 0.65058051 |
| Foxd3 | 1422210_at | 0.12298744 | 0.39927456 | 0.66574299 |
| Col1a1 | 1423669_at | −0.6212641 | 0.40659023 | 0.6718836 |
| Fgf6 | 1427582_at | 0.13306027 | 0.43564081 | 0.69508034 |
| Nog | 1422300_at | 0.1532112 | 0.44376711 | 0.70129789 |
| Smad3 | 1450472_s_at | 0.28466688 | 0.44828933 | 0.70498612 |
| Fbxw4 | 1417226_at | 0.15445078 | 0.48947258 | 0.73441242 |
| Six2 | 1427436_at | 0.11798718 | 0.49326442 | 0.73685768 |
| Dlx2 | 1448877_at | 0.17993045 | 0.50144031 | 0.74322059 |
| Hoxd11 | 1450584_at | 0.09335222 | 0.51678271 | 0.75267603 |
| Bmp4 | 1422912_at | −0.1515746 | 0.52844446 | 0.76072052 |
| Rarb | 1454906_at | 0.13246962 | 0.58074285 | 0.79545915 |
| Msx1 | 1417127_at | −0.0792768 | 0.6088118 | 0.81219928 |
| Pax7 | 1452510_at | −0.0726034 | 0.61587116 | 0.81680712 |
| Por | 1416933_at | −0.0809813 | 0.64020848 | 0.83040587 |
| Thbs1 | 1460302_at | −0.0940899 | 0.6403299 | 0.83041932 |
| Rara | 1450180_a_at | −0.1450325 | 0.65688912 | 0.83924187 |
| Osr1 | 1449350_at | 0.06674263 | 0.65796737 | 0.83979472 |
| Nkx3-2 | 1421464_at | 0.07259392 | 0.65988471 | 0.84131336 |
| Snai1 | 1448742_at | 0.051586 | 0.71227826 | 0.86945623 |
| Hand2 | 1436041_at | 0.05183208 | 0.71914945 | 0.87278294 |
| Lep | 1422582_at | −0.051409 | 0.74333518 | 0.88629937 |
| Sfrp2 | 1448201_at | 0.26766348 | 0.76534268 | 0.89810537 |
| Myf5 | 1420757_at | 0.03687913 | 0.79843488 | 0.91361693 |
| Ihh | 1450704_at | 0.03067369 | 0.82163053 | 0.9243161 |
| Efemp1 | 1427183_at | 0.22630155 | 0.84645157 | 0.93572931 |
| Hoxd3 | 1421537_at | −0.0194301 | 0.90332787 | 0.96012428 |
| Rspo2 | 1455893_at | −0.0229601 | 0.96084842 | 0.9833494 |

TABLE 12

Adipocyte Differentiation GO:0045444

| Symbol | probeid | logFC | P. Value | fdr |
|---|---|---|---|---|
| Frzb | 1416658_at | 6.48749238 | 8.83E−06 | 0.02471733 |
| Scd1 | 1415965_at | 6.92946129 | 2.02E−05 | 0.02471733 |
| Wif1 | 1425425_a_at | 5.61016474 | 2.97E−05 | 0.02471733 |
| Wwtr1 | 1417818_at | 4.26966834 | 4.04E−05 | 0.02471733 |
| Bmp2 | 1423635_at | 5.78726506 | 5.84E−05 | 0.02471733 |
| Medag | 1452244_at | 2.54509537 | 0.00012336 | 0.02520744 |
| Fndc3b | 1433833_at | 4.14105154 | 0.00016123 | 0.02523526 |
| Id2 | 1435176_a_at | 2.55980464 | 0.00017265 | 0.02523526 |
| Enpp1 | 1419276_at | 4.18103881 | 0.0001804 | 0.025505 |
| Ccnd1 | 1448698_at | 4.35237065 | 0.0006197 | 0.03397116 |
| Selenbp1 | 1450699_at | −2.0726353 | 0.00069184 | 0.03471676 |
| Plcb1 | 1435043_at | 4.48210625 | 0.00069203 | 0.03471676 |

TABLE 12-continued

| Adipocyte Differentiation GO:0045444 | | | | |
|---|---|---|---|---|
| Symbol | probeid | logFC | P. Value | fdr |
| Igf1 | 1419519_at | 4.10582922 | 0.00076686 | 0.03552034 |
| 4932438A13Rik | 1444660_at | −1.7217063 | 0.00083553 | 0.03627182 |
| Insig1 | 1454671_at | 2.08360386 | 0.00085701 | 0.03646133 |
| Asxl2 | 1460597_at | −2.6979367 | 0.00092542 | 0.0368767 |
| Itga6 | 1422445_at | 2.16501935 | 0.00095162 | 0.03712712 |
| Ero1l | 1449324_at | −5.2415423 | 0.00109722 | 0.03974742 |
| Klf4 | 1417394_at | 2.49143131 | 0.00117445 | 0.04059755 |
| Snai2 | 1418673_at | 5.03701152 | 0.00128582 | 0.04171829 |
| Lama4 | 1424807_at | 1.79871601 | 0.00144798 | 0.04381912 |
| Plac8 | 1451335_at | −3.9343763 | 0.00197629 | 0.04910038 |
| Zbtb16 | 1419874_x_at | 3.80377306 | 0.00239811 | 0.05325226 |
| Rgs2 | 1419248_at | −2.0621651 | 0.00309171 | 0.05930885 |
| Id4 | 1423259_at | 3.91112981 | 0.00323253 | 0.06026486 |
| Egr2 | 1427683_at | 2.26204995 | 0.00334336 | 0.06120178 |
| Gpx1 | 1460671_at | −1.5018199 | 0.00419115 | 0.06714193 |
| 1100001G20Rik | 1434484_at | −2.8361979 | 0.00426222 | 0.06782998 |
| Zfpm2 | 1449314_at | 2.05338287 | 0.0043193 | 0.06807548 |
| Mex3c | 1444701_at | 2.84275529 | 0.00439563 | 0.06871649 |
| Lamb3 | 1417812_a_at | 1.6568793 | 0.00481526 | 0.07143995 |
| Osbpl8 | 1437069_at | −1.0291454 | 0.00523485 | 0.07380639 |
| Tcf7l2 | 1429428_at | 2.81979243 | 0.00526505 | 0.07387511 |
| Fcor | 1439834_at | −1.0060617 | 0.00590615 | 0.07772749 |
| Nipbl | 1442103_at | −1.2510927 | 0.00646363 | 0.08095419 |
| Tgfb1 | 1445360_at | −1.8533881 | 0.00659249 | 0.08152761 |
| Psmb8 | 1422962_a_at | −2.8058177 | 0.00674644 | 0.08249817 |
| Creb1 | 1428755_at | −2.7091354 | 0.00842715 | 0.09235384 |
| Bnip3 | 1422470_at | 4.08594527 | 0.00951743 | 0.09797892 |
| Creb5 | 1457222_at | 2.78212192 | 0.01161505 | 0.10890856 |
| Akt1 | 1425711_a_at | 0.64331207 | 0.01322662 | 0.1168866 |
| Pex11a | 1419365_at | 3.11498759 | 0.01342737 | 0.11774318 |
| Wnt5b | 1422602_a_at | 1.82156613 | 0.015113 | 0.12499747 |
| Adrb2 | 1437302_at | −1.425485 | 0.01631237 | 0.13005204 |
| Osbpl11 | 1436027_at | −1.5133477 | 0.01644253 | 0.13044409 |
| Bbs12 | 1447275_at | 2.08525895 | 0.01676428 | 0.13158474 |
| Dact1 | 1417937_at | 2.66826005 | 0.01872908 | 0.13938951 |
| Asxl1 | 1458380_at | −1.3363295 | 0.02003387 | 0.1445676 |
| Arl4a | 1425411_at | 1.29146942 | 0.02051407 | 0.14648592 |
| Sox8 | 1435438_at | 3.11014067 | 0.02223232 | 0.15292445 |
| Zc3h12a | 1443993_at | −1.3946394 | 0.02318622 | 0.15612903 |
| Zfp385a | 1418865_at | 0.54201008 | 0.02368729 | 0.15748576 |
| Hmga2 | 1450781_at | 1.09586861 | 0.02694941 | 0.16831614 |
| Alms1 | 1456950_at | −0.9174364 | 0.02699956 | 0.16844556 |
| Tgfb1i1 | 1418136_at | 2.24534212 | 0.03175692 | 0.18296741 |
| Jdp2 | 1450350_a_at | −1.716068 | 0.03804747 | 0.20180716 |
| Crebbp | 1459804_at | −1.3274553 | 0.0394602 | 0.20599124 |
| Lrg1 | 1417290_at | −1.3965514 | 0.04589125 | 0.22371225 |
| Wnt5a | 1448818_at | 2.93263031 | 0.0492736 | 0.23264251 |
| Adipoq | 1422651_at | −0.9677413 | 0.04950593 | 0.23318715 |
| Sirt1 | 1418640_at | 0.66458786 | 0.04979551 | 0.23372124 |
| Jag1 | 1434070_at | 1.60242889 | 0.05099174 | 0.23672447 |
| Arid5b | 1458238_at | −0.6856622 | 0.05148946 | 0.23793299 |
| Ptgs2 | 1417263_at | 1.37192735 | 0.0526271 | 0.24106591 |
| Gata2 | 1450333_a_at | −0.4200574 | 0.0567174 | 0.25105281 |
| Med1 | 1450402_at | −1.5719065 | 0.05957002 | 0.25726603 |
| Dlk2 | 1420807_a_at | 0.37367895 | 0.06840172 | 0.27672997 |
| Axin1 | 1426966_at | 1.169289 | 0.06902748 | 0.27796505 |
| Ppard | 1425703_at | 0.43412189 | 0.07675127 | 0.29440228 |
| Retn | 1449182_at | −0.3872131 | 0.08151515 | 0.3035349 |
| Cebpa | 1418982_at | −0.6341423 | 0.08246593 | 0.30538598 |
| Tbl1x | 1455042_at | −0.5439523 | 0.08527682 | 0.31094428 |
| Cebpb | 1418901_at | −0.9722819 | 0.08544421 | 0.31125265 |
| Cby1 | 1451305_at | 0.67313195 | 0.08765196 | 0.31554846 |
| Mb | 1451203_at | −0.5113074 | 0.08860675 | 0.31723829 |
| Ncor2 | 1451841_a_at | 0.34038456 | 0.09045653 | 0.32098189 |
| Gsk3b | 1439931_at | 0.83461443 | 0.09061475 | 0.32122473 |
| Crebl2 | 1442738_at | −0.6352672 | 0.10791559 | 0.35194886 |
| Aldh6a1 | 1448104_at | 2.58116441 | 0.10869456 | 0.35303424 |
| Eif2ak3 | 1430371_x_at | −1.4225496 | 0.11979267 | 0.37163913 |
| Fabp4 | 1417023_a_at | −1.6804129 | 0.121138 | 0.37369664 |
| Ccdc85b | 1435589_at | 0.27929059 | 0.12208188 | 0.37513349 |
| Rarres2 | 1425091_at | 0.31628662 | 0.12782516 | 0.38425933 |
| Socs1 | 1450446_a_at | 0.28564968 | 0.12917782 | 0.38602244 |
| Sh3pxd2b | 1442919_at | 0.7836116 | 0.1378523 | 0.40031788 |
| Fam57b | 1454209_at | 0.24715081 | 0.14388936 | 0.40878418 |
| Taf8 | 1416450_at | 0.34013535 | 0.14511102 | 0.41054822 |
| Lrp6 | 1451022_at | 1.84723464 | 0.14520466 | 0.41054822 |

TABLE 12-continued

Adipocyte Differentiation GO:0045444

| Symbol | probeid | logFC | P. Value | fdr |
|---|---|---|---|---|
| Runx1t1 | 1448785_at | 0.44754277 | 0.1596707 | 0.43041708 |
| Trib2 | 1426641_at | 0.89133272 | 0.18342065 | 0.46176136 |
| Ankrd26 | 1436071_at | 0.36205722 | 0.20661702 | 0.48819333 |
| Aamdc | 1451381_at | 1.06848603 | 0.21899798 | 0.50195801 |
| Trib3 | 1426065_a_at | 0.295149 | 0.23368155 | 0.51862483 |
| Lpin1 | 1426516_a_at | 0.58391765 | 0.24135771 | 0.52699651 |
| Zfpm1 | 1451046_at | −0.1891087 | 0.25038992 | 0.53649473 |
| Noc3l | 1437500_at | 0.78374168 | 0.25077931 | 0.53689351 |
| Carm1 | 1419743_s_at | 0.64722551 | 0.2531193 | 0.53909773 |
| Ctbp2 | 1422887_a_at | −0.4047828 | 0.27076333 | 0.55490058 |
| Slc2a4 | 1415959_at | 0.17614707 | 0.27374878 | 0.55774954 |
| Msx2 | 1438351_at | 0.35290248 | 0.29922583 | 0.58127152 |
| Ctbp1 | 1415702_a_at | 0.63070087 | 0.30707878 | 0.58884036 |
| Bscl2 | 1420632_a_at | 0.20870757 | 0.31977026 | 0.60081479 |
| Socs7 | 1420766_at | 0.74540021 | 0.33293722 | 0.61166653 |
| Prdm16 | 1429309_at | 0.14230801 | 0.3401689 | 0.61832364 |
| Sfrp1 | 1428136_at | 0.16311129 | 0.34404904 | 0.62158781 |
| Mrap | 1451371_at | −0.1599235 | 0.35444922 | 0.630343 |
| Mettl8 | 1451141_at | 0.66162887 | 0.3773748 | 0.6487262 |
| Wnt1 | 1425377_at | 0.36975782 | 0.37967184 | 0.65054435 |
| Gm6484 | 1427422_at | 0.12539848 | 0.40792345 | 0.67301857 |
| Adrb3 | 1421555_at | −0.1013874 | 0.48109302 | 0.72872465 |
| Aloxe3 | 1449237_at | 0.11167171 | 0.49007502 | 0.734659 |
| Sod2 | 1454976_at | −0.4642386 | 0.49858924 | 0.74112024 |
| Sh2b2 | 1450718_at | 0.33787655 | 0.50093283 | 0.7428897 |
| Nudt7 | 1430896_s_at | −0.5009291 | 0.52179927 | 0.75602895 |
| Hes1 | 1418102_at | 0.12158584 | 0.55711349 | 0.78024953 |
| Gpr116 | 1440225_at | −0.6471556 | 0.57903346 | 0.79420315 |
| Dkkl1 | 1417787_at | 0.07057331 | 0.60962 | 0.81252932 |
| Uchl1 | 1448260_at | 0.0721505 | 0.6101289 | 0.81282636 |
| Cebpd | 1456605_at | 0.18895067 | 0.63866748 | 0.82943279 |
| Gata3 | 1448886_at | −0.083382 | 0.65162031 | 0.83654281 |
| Pparg | 1420715_a_at | −0.0670199 | 0.66484103 | 0.84418045 |
| Fndc5 | 1435115_at | 0.09998857 | 0.66491922 | 0.84418045 |
| Lrp5 | 1449299_at | 0.12006994 | 0.66717382 | 0.84534924 |
| Adig | 1424729_at | 0.05957171 | 0.67676323 | 0.8507174 |
| Mmp11 | 1417234_at | 0.08486384 | 0.71762364 | 0.87217505 |
| Lep | 1422582_at | −0.051409 | 0.74333518 | 0.88629937 |
| Sfrp2 | 1448201_at | 0.26766348 | 0.76534268 | 0.89810537 |
| Wnt3a | 1422093_at | −0.0387946 | 0.81145358 | 0.91983231 |
| Adrb1 | 1423420_at | −0.0217709 | 0.87321293 | 0.94746113 |
| Wnt10b | 1426091_a_at | 0.02676453 | 0.92652487 | 0.96924821 |
| Fgf10 | 1420690_at | −0.0036086 | 0.98699864 | 0.99442913 |

REFERENCES

All references cited herein are hereby incorporated by reference in their entirety.

Ashburner, M., Ball, C. A., Blake, J. A., Botstein, D., Butler, H., Cherry, J. M., Davis, A. P., Dolinski, K., Dwight, S. S., Eppig, J. T., et al. (2000). Gene ontology: tool for the unification of biology. The Gene Ontology Consortium. Nat Genet 25, 25-29.

Barker, N., van Es, J. H., Kuipers, J., Kujala, P., van den Born, M., Cozijnsen, M., Haegebarth, A., Korving, J., Begthel, H., Peters, P. ., et al. (2007). Identification of stem cells in small intestine and colon by marker gene Lgr5. Nature 449, 1003-1007.

Barrett, T., Suzek, T. O., Troup, D. B., Wilhite, S. E., Ngau, W. C., Ledoux, P., Rudnev, D., Lash, A. E., Fujibuchi, W., and Edgar, R. (2005). NCBI GEO: mining millions of expression profiles—database and tools. Nucleic Acids Res 33, D562-566.

Belkind-Gerson, J., Carreon-Rodriguez, A., Benedict, L. A., Steiger, C., Pieretti, A., Nagy, N., Dietrich, J., and Goldstein, A. M. (2013). Nestin-expressing cells in the gut give rise to enteric neurons and glial cells. Neurogastroenterology and motility : the official journal of the European Gastrointestinal Motility Society 25, 61-69 e67.

Bénazet, J.-D., Bischofberger, M., Tiecke, E., Gonsalves, A., Martin, J. F., Zuniga, A., Naef, F., and Zeller, R. (2009). A Self-Regulatory System of Interlinked Signaling Feedback Loops Controls Mouse Limb Patterning. Science 323, 1050-1053.

Benjamini, Y., and Hochberg, Y. (1995). Controlling the false discovery rate; A practical and powerful approach to multiple testing. J Roy Stat Soc Ser B 57, 289-300.

Bianco, P., Cao, X., Frenette, P. S., Mao, J. J., Robey, P.G., Simmons, P. J., and Wang, C. Y. (2013). The meaning, the sense and the significance: translating the science of mesenchymal stem cells into medicine. Nature medicine 19, 35-42.

Bolstad, B. M., Collin, F., Bretttscneider, J., Simpson, K., Cope, L. M., Irizarry, R., and Speed, T. P. (2005). Quality Assesment of Affymetrix GeneChip Data. In Bioinformatics and Computaional Biology Solutions Using R and Bioconductor, R. Gentleman, V. Carey, W. Huber, I. R A, and S. Dudoit, eds. (New York: Springer).

Canalis, E., Parker, K., and Zanotti, S. (2011). Gremlin1 is required for skeletal development and postnatal skeletal homeostasis. J Cell Physiol.

Clevers, H., and Batlle, E. SnapShot: The Intestinal Crypt. Cell 152, 1198-1198.e1192.

Crisan, M., Yap, S., Casteilla, L., Chen, C.-W., Corselli, M., Park, T. S., Andriolo, G., Sun, B., Zheng, B., Zhang, L., et al. (2008). A Perivascular Origin for Mesenchymal Stem Cells in Multiple Human Organs. Cell stem cell 3, 301-313.

Delorme, B., Ringe, J., Pontikoglou, C., Gaillard, J., Langonne, A., Sensebe, L., Noel, D., Jorgensen, C., Haupl, T., and Charbord, P. (2009). Specific lineage-priming of bone marrow mesenchymal stem cells provides the molecular framework for their plasticity. Stem cells 27, 1142-1151.

Ding, L., Saunders, T. L., Enikolopov, G., and Morrison, S. J. (2012). Endothelial and perivascular cells maintain haematopoietic stem cells. Nature 481, 457-462.

Dominici, M., Le Blanc, K., Mueller, I., Slaper-Cortenbach, I., Marini, F., Krause, D., Deans, R., Keating, A., Prockop, D., and Horwitz, E. (2006). Minimal criteria for defining multipotent mesenchymal stromal cells. The International Society for Cellular Therapy position statement. Cytotherapy 8, 315-317.

Dranovsky, A., Picchini, A. M., Moadel, T., Sisti, A. C., Yamada, A., Kimura, S., Leonardo, E. D., and Hen, R. (2011). Experience dictates stem cell fate in the adult hippocampus. Neuron 70, 908-923.

Ducy, P., Zhang, R., Geoffroy, V., Ridall, A.L., and Karsenty, G. (1997). Osf2/Cbfa1: a transcriptional activator of osteoblast differentiation. Cell 89, 747-754.

Friedenstein, A. J., Chailakhyan, R. K., Latsinik, N. V., Panasyuk, A. F., and Keiliss-Borok, I. V. (1974a). Stromal cells responsible for transferring the microenvironment of the hemopoietic tissues. Cloning in vitro and retransplantation in vivo. Transplantation 17, 331-340.

Friedenstein, A. J., Deriglasova, U. F., Kulagina, N. N., Panasuk, A. F., Rudakowa, S. F., Luria, E.A., and Ruadkow, I.A. (1974b). Precursors for fibroblasts in different populations of hematopoietic cells as detected by the in vitro colony assay method. Exp Hematol 2, 83-92.

Gentleman, R. C., Carey, V.J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol 5, R80.

Gerber, H. P., Vu, T. H., Ryan, A. M., Kowalski, J., Werb, Z., and Ferrara, N. (1999). VEGF couples hypertrophic cartilage remodeling, ossification and angiogenesis during endochondral bone formation. Nature medicine 5, 623-628.

Grcevic, D., Pejda, S., Matthews, B. G., Repic, D., Wang, L., Li, H., Kronenberg, M. S., Jiang, X., Maye, P., Adams, D. J., et al. (2012). In vivo fate mapping identifies mesenchymal progenitor cells. Stem cells 30, 187-196.

Hsu, D. R., Economides, A. N., Wang, X., Eimon, P. M., and Harland, R. M. (1998). The Xenopus dorsalizing factor Gremlin identifies a novel family of secreted proteins that antagonize BMP activities. Molecular cell 1, 673-683.

Ihaka, R., and Gentleman, R. (1996). R: A language for data analysis and graphics. Journal of Computational and Graphical Statistics 5, 299-314.

Jaeger, E., Leedham, S., Lewis, A., Segditsas, S., Becker, M., Cuadrado, P. R., Davis, H., Kaur, K., Heinimann, K., Howarth, K., et al. (2012). Hereditary mixed polyposis syndrome is caused by a 40-kb upstream duplication that leads to increased and ectopic expression of the BMP antagonist GREM1. Nat Genet 44, 699-703.

Kalajzic, I., Kalajzic, Z., Kaliterna, M., Gronowicz, G., Clark, S. H., Lichtler, A.C., and Rowe, D. (2002). Use of type I collagen green fluorescent protein transgenes to identify subpopulations of cells at different stages of the osteoblast lineage. J Bone Miner Res 17, 15-25.

Khokha, M. K., Hsu, D., Brunet, L. J., Dionne, M. S., and Harland, R. M. (2003). Gremlin is the BMP antagonist required for maintenance of Shh and Fgf signals during limb patterning. Nat Genet 34, 303-307.

Kosinski, C., Li, V. S. W., Chan, A. S. Y., Zhang, J., Ho, C., Tsui, W. Y., Chan, T. L., Mifflin, R. C., Powell, D. W., Yuen, S. T., et al. (2007). Gene expression patterns of human colon tops and basal crypts and BMP antagonists as intestinal stem cell niche factors. Proceedings of the National Academy of Sciences 104, 15418-15423.

Kronenberg, H. M. (2003). Developmental regulation of the growth plate. Nature 423, 332-336.

Levin, D. E., Sala, F. G., Barthel, E. R., Speer, A.L., Hou, X., Torashima, Y., and Grikscheit, T. C. (2013). A "living bioreactor" for the production of tissue-engineered small intestine. Methods in molecular biology 1001, 299-309.

Liu, Y., Strecker, S., Wang, L., Kronenberg, M. S., Wang, W., Rowe, D. W., and Maye, P. (2013). Osterix-cre labeled progenitor cells contribute to the formation and maintenance of the bone marrow stroma. PloS one 8, e71318.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nature neuroscience 13, 133-140.

Magness, S. T., Bataller, R., Yang, L., and Brenner, D. A. (2004). A dual reporter gene transgenic mouse demonstrates heterogeneity in hepatic fibrogenic cell populations. Hepatology 40, 1151-1159.

Manieri, N. A., Drylewicz, M. R., Miyoshi, H., and Stappenbeck, T. S. (2012). Igf2bp1 is required for full induction of Ptgs2 mRNA in colonic mesenchymal stem cells in mice. Gastroenterology 143, 110-121 e110.

Marsh, M. N., and Trier, J. S. (1974). Morphology and cell proliferation of subepithelial fibroblasts in adult mouse jejunum. II. Radioautographic studies. Gastroenterology 67, 636-645.

Mendez-Ferrer, S., Michurina, T. V., Ferraro, F., Mazloom, A. R., Macarthur, B. D., Lira, S. A., Scadden, D. T., Ma'ayan, A., Enikolopov, G. N., and Frenette, P. S. (2010). Mesenchymal and haematopoietic stem cells form a unique bone marrow niche. Nature 466, 829-834.

Michos, O., Panman, L., Vintersten, K., Beier, K., Zeller, R., and Zuniga, A. (2004). Gremlin-mediated BMP antagonism induces the epithelial-mesenchymal feedback signaling controlling metanephric kidney and limb organogenesis. Development 131, 3401-3410.

Mignone, J. L. J., Kukekov, V. V., Chiang, A.-S. A., Steindler, D. D., and Enikolopov, G. G. (2004). Neural stem and progenitor cells in nestin-GFP transgenic mice. Journal of Comparative Neurology 469, 311-324.

Mitola, S., Ravelli, C., Moroni, E., Salvi, V., Leali, D., Ballmer-Hofer, K., Zammataro, L., and Presta, M. (2010). Gremlin is a novel agonist of the major proangiogenic receptor VEGFR2. Blood 116, 3677-3680.

Mizoguchi, T., Pinho, S., Ahmed, J., Kunisaki, Y., Hanoun, M., Mendelson, A., Ono, N., Kronenberg, Henry M., and Frenette, Paul S. (2014). Osterix Marks Distinct Waves of Primitive and Definitive Stromal Progenitors during Bone Marrow Development. Developmental Cell 29, 340-349.

Morikawa, S., Mabuchi, Y., Kubota, Y., Nagai, Y., Niibe, K., Hiratsu, E., Suzuki, S., Miyauchi-Hara, C., Nagoshi, N., Sunabori, T., et al. (2009). Prospective identification, isolation, and systemic transplantation of multipotent mesenchymal stem cells in murine bone marrow. The Journal of experimental medicine 206, 2483-2496.

Muzumdar, M. D., Tasic, B., Miyamichi, K., Li, L., and Luo, L. (2007). A global double-fluorescent Cre reporter mouse. Genesis 45, 593-605.

Neal, J. V., and Potten, C. S. (1981). Description and basic cell kinetics of the murine pericryptal fibroblast sheath. Gut 22, 19-24.

Newberry, R. D., Stenson, W. F., and Lorenz, R. G. (1999). Cyclooxygenase-2-dependent arachidonic acid metabolites are essential modulators of the intestinal immune response to dietary antigen. Nature medicine 5, 900-906.

Ng, F., Boucher, S., Koh, S., Sastry, K.S., Chase, L., Lakshmipathy, U., Choong, C., Yang, Z., Vemuri, M. C., Rao, M. S., et al. (2008). PDGF, TGF-beta, and FGF signaling is important for differentiation and growth of mesenchymal stem cells (MSCs): transcriptional profiling can identify markers and signaling pathways important in differentiation of MSCs into adipogenic, chondrogenic, and osteogenic lineages. Blood 112, 295-307.

Ono, N., Ono, W., Mizoguchi, T., Nagasawa, T., Frenette, Paul S., and Kronenberg, Henry M. (2014). Vasculature-Associated Cells Expressing Nestin in Developing Bones Encompass Early Cells in the Osteoblast and Endothelial Lineage. Developmental Cell 29, 330-339.

Park, D., Spencer, J. A., Koh, B. I., Kobayashi, T., Fujisaki, J., Clemens, T. L., Lin, C. P., Kronenberg, H. M., and Scadden, D. T. (2012). Endogenous bone marrow MSCs are dynamic, fate-restricted participants in bone maintenance and regeneration. Cell stem cell 10, 259-272.

Powell, D. W., Pinchuk, I. V., Saada, J. I., Chen, X., and Mifflin, R. C. (2011). Mesenchymal cells of the intestinal lamina propria. Annual review of physiology 73, 213-237.

Powell, D. W., and Saada, J. I. (2012). Mesenchymal stem cells and prostaglandins may be critical for intestinal wound repair. Gastroenterology 143, 19-22.

Quante, M., Tu, S. P., Tomita, H., Gonda, T., Wang, S. S. W., Takashi, S., Baik, G. H., Shibata, W., DiPrete, B., Betz, K. S., et al. (2011). Bone Marrow-Derived Myofibroblasts Contribute to the Mesenchymal Stem Cell Niche and Promote Tumor Growth. Cancer Cell 19, 257-272.

Sacchetti, B., Funari, A., Michienzi, S., Di Cesare, S., Piersanti, S., Saggio, I., Tagliafico, E., Ferrari, S., Robey, P.G., Riminucci, M., et al. (2007). Self-Renewing Osteoprogenitors in Bone Marrow Sinusoids Can Organize a Hematopoietic Microenvironment. Cell 131, 324-336.

Sharan, S. K., Thomason, L. C., Kuznetsov, S. G., and Court, D. L. (2009). Recombineering: a homologous recombination-based method of genetic engineering. Nat Protocols 4, 206-223.

Smyth, G. K. (2004). Linear Models and Empirical Bayes Methods for Assessing Differential Expression in Microarray Experiments. Statistical Applications in Genetics and Molecular Biology 3, Article 3, http://www.bepress.com/sagmb/vol3/iss1/art3/.

Sneddon, J. B., Zhen, H. H., Montgomery, K., van de Rijn, M., Tward, A. D., West, R., Gladstone, H., Chang, H. Y., Morganroth, G. S., Oro, A. E., et al. (2006). Bone morphogenetic protein antagonist gremlin 1 is widely expressed by cancer-associated stromal cells and can promote tumor cell proliferation. Proceedings of the National Academy of Sciences 103, 14842-14847.

Snippert, H. J., van der Flier, L. G., Sato, T., van Es, J. H., van den Born, M., Kroon-Veenboer, C., Barker, N., Klein, A. M., van Rheenen, J., Simons, B. D., et al. (2010). Intestinal Crypt Homeostasis Results from Neutral Competition between Symmetrically Dividing Lgr5 Stem Cells. Cell 143, 134-144.

Takashima, Y., Era, T., Nakao, K., Kondo, S., Kasuga, M., Smith, A.G., and Nishikawa, S. (2007). Neuroepithelial cells supply an initial transient wave of MSC differentiation. Cell 129, 1377-1388.

Tang, W., Zeve, D., Suh, J. M., Bosnakovski, D., Kyba, M., Hammer, R. E., Tallquist, M. D., and Graff, J. M. (2008). White Fat Progenitor Cells Reside in the Adipose Vasculature. Science 322, 583-586.

Voehringer, D., Liang, H. E., and Locksley, R. M. (2008). Homeostasis and effector function of lymphopenia-induced "memory-like" T cells in constitutively T cell-depleted mice. Journal of immunology 180, 4742-4753.

Walker, M. R., Brown, S. L., Riehl, T. E., Stenson, W. F., and Stappenbeck, T. S. (2010). Growth Factor Regulation of Prostaglandin-Endoperoxide Synthase 2 (Ptgs2) Expression in Colonic Mesenchymal Stem Cells. Journal of Biological Chemistry 285, 5026-5039.

Wilm, B., Ipenberg, A., Hastie, N. D., Burch, J. B., and Bader, D. M. (2005). The serosal mesothelium is a major source of smooth muscle cells of the gut vasculature. Development 132, 5317-5328.

Wu, Z., and Irizarry, R. A. (2005). Stochastic models inspired by hybridization theory for short oligonucleotide arrays. J Comput Biol 12, 882-893.

Wu, Z., Irizarry, R. A., Gentleman, R., Murillo, F. M., and Spencer, F. (2004). A model based background adjustment for oligonucleotide expression. J Am Stat Assoc 99, 909-917.

Xu, Z., Yu, S., Hsu, C.H., Eguchi, J., and Rosen, E. D. (2008). The orphan nuclear receptor chicken ovalbumin upstream promoter-transcription factor II is a critical regulator of adipogenesis. Proceedings of the National Academy of Sciences of the United States of America 105, 2421-2426.

Zajicek, G. (1982). The intestinal proliferon hypothesis. J Theor Biol 97, 337-340.

Zhou, B. O., Yue, R., Murphy, M. M., Peyer, J. G., and Morrison, S. J. (2014). Leptin-Receptor-Expressing Mesenchymal Stromal Cells Represent the Main Source of Bone Formed by Adult Bone Marrow. Cell stem cell.

Tronche F, Kellendonk C, Kretz O, Gass P, Anlag K, Orban P C, Bock R, Klein R, Schutz G. Disruption of the glucocorticoid receptor gene in the nervous system results in reduced anxiety. Nat Genet. 1999 September; 23(1): 99-103

Balordi F, Fishell G. Mosaic Removal of Hedgehog Signaling in the Adult SVZ Reveals That the Residual Wild-Type Stem Cells Have a Limited Capacity for Self-Renewal. J Neurosci. 2007; 27:14248-14259.

Maes C, Kobayashi T, Selig M K, Torrekens S, Roth S I, Mackem S, Carmeliet G, Kronenberg HM. Osteoblast precursors, but not mature osteoblasts, move into developing and fractured bones along with invading blood vessels. Dev Cell. 2010 Aug 17;19(2):329-44.

Feng J, Mantesso A, De Bari C, Nishiyama A, Sharpe P T. Dual origin of mesenchymal stem cells contributing to organ growth and repair. Proc Natl Acad Sci USA. 2011 Apr. 19; 108(16):6503-8.

Logan M, Martin J F, Nagy A, Lobe C, Olson E N, Tabin C J. Expression of Cre Recombinase in the developing mouse limb bud driven by a Prx1 enhancer. Genesis. 2002 June; 33(2):77-80.

What is claimed is:

1. A method of treating a disease, degeneration, or injury of bone, or cartilage, or both, in a subject comprising administering a therapeutically effective amount of a composition comprising an acceptable carrier and isolated osteochondroreticular (OCR) stem cells that express Grem1 to a site in need thereof in the subject, wherein the isolated OCR stem cells are at least about 70% pure.

2. The method of claim 1 wherein the site in need thereof is a joint and the therapeutically effective amount of the composition is administered into a space of the joint or into articular tissue of the joint.

3. The method of claim 2, wherein the disease treated is osteoarthritis.

4. The method of claim 1, wherein the site in need thereof is a fracture, and the therapeutically effective amount of the composition is administered into the fracture or tissue surrounding the fracture, or both.

* * * * *

SEQUENCE LISTING

<160> NUMBER OF SEQ ID NOS: 14

<210> SEQ ID NO 1
<211> LENGTH: 83
<212> TYPE: DNA
<213> ORGANISM: Artificial Sequence
<220> FEATURE:
<223> OTHER INFORMATION: Synthetic oligonucleotide: F-Grem1
      recombineering primer

<400> SEQUENCE: 1 gattttact aaataacttt cttattgtct gtgtccccct ctctttgtcc tttgtctaga    60
atgtccaatt tactgaccgt aca                                          83

<210> SEQ ID NO 2
<211> LENGTH: 83
<212> TYPE: DNA
<213> ORGANISM: Artificial Sequence
<220> FEATURE:
<223> OTHER INFORMATION: Synthetic oligonucleotide: R-Grem1
      recombineering primer

<400> SEQUENCE: 2
gttggcagta gggtccccag gaggagaagc aacgctccca cagtgtatgc ggtgcgatta   60
ttatgtacct gactgatgaa gtt                                          83

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide: F- Grem1-creERT

<400> SEQUENCE: 3
ctgtgtcgaa ttactcagtt tgatg                                        25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide: R- Grem1-creERT

<400> SEQUENCE: 4
aatgttgctg gatagttttt actgc                                        25

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide: F- Grem1-LacZ

<400> SEQUENCE: 5
atcctctgca tggtcaggtc                                              20

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide: R- Grem1-LacZ

<400> SEQUENCE: 6
cgtggcctga ttcattcc                                                18

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide: F- R26-TdTomato or
      ZsGreen (the WPRE)

<400> SEQUENCE: 7
actgtgtttg ctgacgcaac                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide: R- R26-TdTomato or
      ZsGreen (the WPRE)

<400> SEQUENCE: 8
caacaccacg gaattgtcag                                                 20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide: F- Nes-GFP or
      2.3ColGFP or R26-Confetti (the GFP)

<400> SEQUENCE: 9
gagctgaagg gcatcgactt caag                                            24

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide: R- Nes-GFP or
      2.3ColGFP or R26-Confetti (the GFP)

<400> SEQUENCE: 10
ggactgggtg ctcaggtagt gg                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide: F- Nes-CreERT

<400> SEQUENCE: 11
gcggcatggt gcaagttgaa t                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide: R- Nes-CreERT

<400> SEQUENCE: 12
cgttcaccgg catcaacgtt t                                               21

<210> SEQ ID NO 13

```
<211> LENGTH: 25
<212> TYPE: DNA
<213> ORGANISM: Artificial Sequence
<220> FEATURE:
<223> OTHER INFORMATION: Synthetic oligonucleotide:  F- R26-iDTA

<400> SEQUENCE: 13
acctggttat gtagattcca ttcaa                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide:  R- R26-iDTA

<400> SEQUENCE: 14
cagaagtaag gttccttcac aaaga                                              25
```